United States Patent
Pierce et al.

(10) Patent No.: US 8,921,555 B2
(45) Date of Patent: Dec. 30, 2014

(54) SUBSTITUTED-1,3,8-TRIAZASPIRO[4.5] DECANE-2,4-DIONES

(75) Inventors: Joan M. Pierce, LaJolla, CA (US); Jeffrey J. Hale, Westfield, NJ (US); Shouwu Miao, Edison, NJ (US); Petr Vachal, Summit, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/378,237

(22) PCT Filed: Jun. 7, 2010

(86) PCT No.: PCT/US2010/037566
§ 371 (c)(1),
(2), (4) Date: Dec. 14, 2011

(87) PCT Pub. No.: WO2010/147776
PCT Pub. Date: Dec. 23, 2010

(65) Prior Publication Data
US 2012/0095001 A1    Apr. 19, 2012

Related U.S. Application Data

(60) Provisional application No. 61/187,320, filed on Jun. 16, 2009.

(51) Int. Cl.
C07D 471/10    (2006.01)
A61K 31/438    (2006.01)
A61K 31/506    (2006.01)
A61K 31/501    (2006.01)
A61K 31/44     (2006.01)

(52) U.S. Cl.
CPC .............. A61K 31/44 (2013.01); C07D 471/10 (2013.01)
USPC ............ 546/20; 546/230; 514/278; 514/256; 514/275; 514/255.05; 514/252.04

(58) Field of Classification Search
USPC .................... 546/20, 230; 514/278, 256, 275, 514/255.05, 252.04
See application file for complete search history.

(56) References Cited

U.S. PATENT DOCUMENTS

| 4,241,208 A * | 12/1980 | Murayama et al. ............. 546/20 |
| 6,043,366 A | 3/2000 | Adam et al. |
| 6,482,829 B2 | 11/2002 | Galley et al. |
| 2006/0014769 A1 | 1/2006 | Kong et al. |
| 2006/0229301 A1 | 10/2006 | Nishizawa |
| 2008/0124740 A1 | 5/2008 | Evdokimov et al. |

FOREIGN PATENT DOCUMENTS

| WO | WO0194346 A1 | 12/2001 |
| WO | WO2006081327 A2 | 3/2006 |
| WO | WO2008030412 A2 | 3/2008 |
| WO | WO 2008030412 A2 * | 3/2008 |
| WO | WO2008144266 A1 | 11/2008 |

OTHER PUBLICATIONS

Vachal et al.; "1,3,8-Triazaspiro[4.5]decane-2,4-diones as Efficacious Pan-Inhibitors of Hypoxia-Inducible Factor Prolyl Hydroxylase 1-3 (HIF PHD1-3) for the Treatment of Anemia"; 2012; J. Med. Chem.; 55:2945-2956.*
Nieto et al., "Solution-Phase Parallel Synthesis of Spirohydantoins", Journal of Combinatorial Chemistry, vol. 7, p. 258-263 (2005).
Rowbottom et al., "Synthesis and structure-activity relationships of spirohydantoin-derived small-molecule antagonists of the melanin-concentrating hormone receptor-1 (MCH-R1)", ScienceDirect, Bioorganic & Medicinal Chemistry Letters 17, p. 2171-2178 (2007).

* cited by examiner

*Primary Examiner* — Timothy Thomas
(74) *Attorney, Agent, or Firm* — Matthew A. Leff; John C. Todaro

(57) ABSTRACT

The present invention relates to substituted 1,3,8-triazaspiro [4.5]decame-2,4-diones useful as HIF prolyl hydroxylase inhibitors to treat anemia and like conditions.

4 Claims, No Drawings

SUBSTITUTED-1,3,8-TRIAZASPIRO[4.5]DECANE-2,4-DIONES

CROSS REFERENCE TO RELATED APPLICATIONS

This application is a U.S. National Phase application under 35 U.S.C. §371 of PCT Application No. PCT/US2010/037566, filed Jun. 7, 2010, which claims priority under 35 U.S.C. §119(e) from U.S. Provisional Application Ser. No. 61/187,320, filed Jun. 16, 2009.

BACKGROUND OF THE INVENTION

The insufficient delivery of oxygen to cells and tissues is associated with anemia, which is defined as a deficiency in the blood's oxygen-carrying capacity, and ischemia, in which restrictions in blood supply are caused by a constriction or blockage of blood vessels. Anemia can be caused by the loss of red blood cells (hemorrhage), excessive red blood cell destruction (hemolysis) or deficiencies in erythropoiesis (production of red blood cells from precursors found in the bone marrow). The symptoms of anemia can include weakness, dizziness, fatigue, pallor, impairment of cognitive function and a general reduction in quality of life. Chronic and/or severe anemia can lead to the exacerbation of myocardial, cerebral or peripheral ischemia and to heart failure. Ischemia is defined as an absolute or relative shortage of oxygen to a tissue or organ and can result from disorders such as atherosclerosis, diabetes, thromboembolisms, hypotension, etc. The heart, brain and kidney are especially sensitive to ischemic stress caused by low blood supply.

The primary pharmacological treatment for anemia is administration of some variant of recombinant human erythropoietin (EPO). For anemias associated with kidney disease, chemotherapy-induced anemia, anemia from HIV-therapy or anemia due to blood loss, recombinant EPO is administered to enhance the supply of the hormone, correct the shortage of red blood cells and increase the blood's oxygen-carrying capacity. EPO replacement is not always sufficient to stimulate optimal erythropoiesis (e.g., in patients with iron processing deficiencies) and has associated risks.

Hypoxia-inducible factor (HIF) has been identified as a primary regulator of the cellular response to low oxygen. HIF is a heterodimeric gene transcription factor consisting of a highly regulated α-subunit (HIF-α) and a constitutively expressed β-subunit (HIF-β, also known as ARNT, or aryl hydrocarbon receptor nuclear transporter). HIF target genes are reported to be associated with various aspects of erythropoiesis (e.g., erythropoietin (EPO) and EPO receptor), glycolysis and angiogenesis (e.g., vascular endothelial growth factor (VEGF)). Genes for proteins involved in iron absorption, transport and utilization as well as heme synthesis are also targets of HIF.

Under normal oxygenation, HIF-α is a substrate in a reaction with molecular oxygen, which is catalyzed by a family of iron(II)-, 2-ketoglutarate- and ascorbate-dependent dioxygenase enzymes called PHD-1 (EGLN2, or egg laying abnormal 9 homolog 2, PHD2 (EGLN1), and PHD3 (EGLN3). Proline residues of HIF-α are hydroxylated (e.g., Pro-402 and Pro-564 of HIF-1α) and the resulting product is a target of the tumor suppressor protein von-Hippel Lindau, a component of an E3 ubiquitin ligase multiprotein complex involved in protein ubiquitination. Under low oxygenation, the HIF-α hydroxylation reaction is less efficient and HIF-α is available to dimerize with HIF-β. HIF dimers are translocated to the cell nucleus where they bind to a hypoxia-responsive enhancer element of HIF target genes.

Cellular levels of HIF are known to increase under conditions of hypoxia and after exposure to hypoxia mimetic agents. The latter includes, but is not limited to, specific metal ions (e.g., cobalt, nickel, manganese), iron chelators (e.g., desferrioxamine) and analogs of 2-ketoglurate (e.g., N-oxalyl glycine). The compounds of the present invention inhibit the HIF prolyl hydroxylases (PHD-1, PHD-2, PHD-3) and can also serve to modulate HIF levels. These compounds therefore have utility for the treatment and/or prevention of disorders or conditions where HIF modulation is desirable, such as anemia and ischemia. As an alternative to recombinant erythropoietin therapy, the compounds of the present invention provide a simpler and broader method for the management of anemia.

International Patent Publication No. WO 2008/030412 (international filing date of Sep. 4, 2007), exemplifies hydantoin spiropiperidine compounds useful as spiropiperidine beta-secretase inhibitors for the treatemtent of Alzheimer's disease.

SUMMARY OF THE INVENTION

The present invention concerns compounds of formula IA compound or a pharmaceutically acceptable salt thereof, or a stereoisomer thereof, or a pharmaceutically acceptable salt of the stereoisomer thereof:

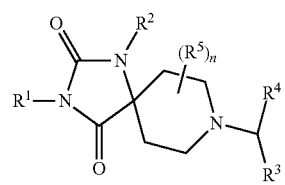

I which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

DETAILED DESCRIPTION OF THE INVENTION

The present invention provides compounds of formula I or a pharmaceutically acceptable salt thereof, or a stereoisomer thereof, or a pharmaceutically acceptable salt of the stereoisomer thereof:

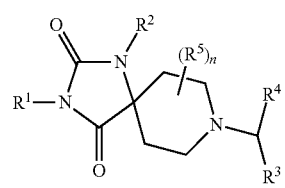

I wherein
n is 0, 1, 2, 3 or 4;
$R^1$ is aryl or heterocyclyl;
$R^2$ is selected from:
  hydrogen,
  aryl($C_0$-$C_6$)alkyl, heterocyclyl($C_0$-$C_6$)alkyl;
$C_{0-10}$ alkyl(oxy)$_{0-1}$ carbonyl$C_{0-10}$ alkyl,
$C_{0-10}$ alkylamino carbonyl$C_{0-10}$ alkyl,
arylamino carbonyl$C_{0-10}$ alkyl,
$C_{3-8}$ cycloalkyl amino carbonyl$C_{0-10}$ alkyl,
($C_{3-8}$)heterocyclyl amino carbonyl$C_{0-10}$ alkyl,
($C_{3-8}$ heterocycloalkyl amino carbonyl $C_{0-10}$ alkyl, and
$C_{0-10}$ alkyloxycarbonylamino carbonyl$C_{0-10}$ alkyl;
$R^3$ is —($C_0$-$C_6$ alkyl)C(O)O($C_0$-$C_{10}$ alkyl), or —($C_0$-$C_6$ alkyl)heterocyclyl;
optionally, $R^1$, $R^2$ and $R^3$ are each independently substituted by 1, 2, 3, or 4 $R^6$;
$R^4$ is selected from hydrogen, $C_1$-$C_3$ alkyl, and oxo;
$R^5$ is selected from hydrogen, —$C_1$-$C_{10}$ alkyl, —O$C_1$-$C_{10}$ alkyl, —($C_0$-$C_6$ alkyl)C(O)O($C_0$-$C_6$ alkyl), OH, —$C_1$-$C_4$ haloalkyl optionally substituted with one to five fluorine, halogen, $NH_2$, $N(C_1$-$C_6$ alkyl)$_2$, $NO_2$, CN, and —$S(O)_{1-2}$;
$R^6$ is chosen from:
halogen,
(carbonyl)$_{0-1}C_{1-10}$ alkyl,
(carbonyl)$_{0-1}C_{2-10}$ alkenyl,
(carbonyl)$_{0-1}C_{2-10}$ alkynyl,
$C_{1-10}$ alkenylamino,
$C_{1-10}$ alkyl(carbonyl)$_{0-1}C_{0-10}$ alkyl,
$C_{0-10}$ alkyl(carbonyl)$_{0-1}$aryl $C_{0-10}$ alkyl,
$C_{0-10}$ alkyl(carbonyl)$_{0-1}C_{3-8}$ cycloalkyl $C_{0-10}$ alkyl,
$C_{0-10}$ alkyl(carbonyl)$_{0-1}$($C_{3-8}$)heterocyclyl $C_{0-10}$ alkyl,
$C_{0-10}$ alkyl(carbonyl)$_{0-1}$($C_{3-8}$ heterocycloalkyl $C_{0-10}$ alkyl,
$C_{1-4}$acylamino $C_{0-10}$ alkyl,
di-($C_{1-10}$ alkyl)amino $C_{0-10}$ alkyl,
aryl$C_{0-10}$ alkylamino $C_{0-10}$ alkyl,
(aryl$C_{0-10}$ alkyl)$_2$amino $C_{0-10}$ alkyl,
$C_{3-8}$ cycloalkyl $C_{0-10}$ alkylamino $C_{0-10}$ alkyl,
$C_{3-8}$ heterocyclyl $C_{0-10}$ alkylamino $C_{0-10}$ alkyl,
$C_{3-8}$ heterocycloalkyl $C_{0-10}$ alkylamino $C_{0-10}$ alkyl,
($C_{3-8}$ cycloalkyl $C_{0-10}$ alkyl)$_2$amino $C_{0-10}$ alkyl,
($C_{3-8}$ heterocyclyl $C_{0-10}$ alkyl)$_2$amino $C_{0-10}$ alkyl,
($C_{3-8}$ heterocycloalkyl $C_{0-10}$ alkyl)$_2$amino $C_{0-10}$ alkyl,
($C_{0-10}$ alkyl)$_2$aminocarbonyl $C_{0-10}$ alkyl,
(aryl $C_{0-10}$ alkyl)$_{1-2}$aminocarbonyl $C_{0-10}$ alkyl,
$C_{0-10}$ alkyl amino(carbonyl)$_{0-1}$ $C_{0-10}$ alkyl,
$C_{3-8}$ cycloalkyl $C_{0-10}$ alkyl amino(carbonyl)$_{0-1}$ $C_{0-10}$ alkyl,
$C_{3-8}$ heterocyclyl $C_{0-10}$ alkyl amino(carbonyl)$_{0-1}$ $C_{0-10}$ alkyl,
$C_{3-8}$ heterocycloalkyl $C_{0-10}$ alkyl amino(carbonyl)$_{0-1}$ $C_{0-10}$ alkyl,
aryl $C_{0-10}$ alkyl amino(carbonyl)$_{0-1}$ $C_{0-10}$ alkyl,
$C_{3-8}$ cycloalkyl $C_{0-10}$ alkyl carbonylamino $C_{0-10}$ alkyl,
$C_{3-8}$ heterocyclyl $C_{0-10}$ alkyl carbonylamino $C_{0-10}$ alkyl,
$C_{3-8}$ heterocycloalkyl $C_{0-10}$ alkyl carbonylamino $C_{0-10}$ alkyl,
aryl $C_{0-10}$ alkyl carbonylamino $C_{0-10}$ alkyl,
$C_{1-10}$ alkoxy (carbonyl)$_{0-1}C_{0-10}$ alkyl,
$C_{0-10}$ alkylcarboxy $C_{0-10}$ alkylamino,
carboxyl $C_{0-10}$ alkyl,
carboxyl aryl,
carboxyl $C_{3-8}$ cycloalkyl,
carboxyl $C_{3-8}$ heterocyclyl,
carboxyl $C_{3-8}$ heterocycloalkyl,
$C_{1-10}$ alkoxy,
$C_{1-10}$alkyloxy $C_{0-10}$alkyl,
$C_{1-10}$ alkyl(carbonyl)$_{0-1}$ oxy,
$C_{3-8}$ heterocyclyl $C_{0-10}$ alkyl(carbonyl)$_{0-1}$oxy,
$C_{3-8}$ heterocycloalkyl $C_{0-10}$ alkyl(carbonyl)$_{0-1}$oxy,
$C_{3-8}$ cycloalkyl $C_{0-10}$ alkyl(carbonyl)$_{0-1}$oxy,
aryl $C_{0-10}$ alkyl(carbonyl)$_{0-1}$oxy,
hydroxy $C_{0-10}$alkyl,
hydroxycarbonyl$C_{0-1}$alkoxy,
hydroxycarbonyl$C_{0-10}$alkyloxy,
$C_{1-10}$ alkylthio,
oxo,
cyano,
nitro,
perfluoro$C_{1-6}$alkyl, and
perfluoro$C_{1-6}$alkoxy, and
wherein $R^6$ is optionally substituted with 1, 2, 3, or 4 substituents, $R^7$, chosen from:
halogen,
(carbonyl)$_{0-1}C_{1-10}$ alkyl,
(carbonyl)$_{0-1}C_{2-10}$ alkenyl,
(carbonyl)$_{0-1}C_{2-10}$ alkynyl,
$C_{1-10}$ alkylcarbonyl,
$C_{2-10}$ alkenylcarbonyl,
$C_{2-10}$ alkynylcarbonyl,
(carbonyl)$_{0-1}$aryl $C_{0-10}$ alkyl,
(carbonyl)$_{0-1}$($C_{3-8}$)heterocyclyl $C_{0-10}$ alkyl,
aryl $C_{0-10}$ alkylcarbonyl,
($C_{3-8}$)heterocyclylcarbonyl,
($C_{3-8}$) heterocycloalkylcarbonyl;
$C_{3-8}$ cycloalkyl $C_{0-10}$ alkyl,
(carbonyl)$_{0-1}$($C_{3-8}$)heterocycloalkyl $C_{0-10}$ alkyl,
$C_{1-4}$acylamino $C_{0-10}$ alkyl,
$CO_{0-1}$alkylamino $C_{0-10}$ alkyl,
di-($C_{1-10}$ alkyl)amino $C_{0-10}$ alkyl,
aryl$C_{0-10}$ alkylamino $C_{0-10}$ alkyl,
(aryl$C_{0-10}$ alkyl)$_2$amino $C_{0-10}$ alkyl,
$C_{3-8}$ cycloalkyl $C_{0-10}$ alkylamino $C_{0-10}$ alkyl,
$C_{3-8}$ heterocyclyl $C_{0-10}$ alkylamino $C_{0-10}$ alkyl,
$C_{3-8}$ heterocycloalkyl $C_{0-10}$ alkylamino $C_{0-10}$ alkyl,
($C_{1-10}$ alkyl)$_2$aminocarbonyl,
arylaminocarbonyl,
$C_{3-8}$ heterocyclylaminocarbonyl,
$C_{1-10}$ alkylaminocarbonyl
$C_{1-10}$ alkoxy (carbonyl)$_{0-1}C_{0-10}$ alkyl,
$C_{1-10}$alkyloxy $C_{0-10}$alkyl,
($C_{1-10}$ alkyl)$_2$aminocarbonyloxy,
hydroxycarbonyl$C_{0-10}$alkoxy,
($C_{1-10}$ alkyl)$_2$aminocarbonyloxy,
(aryl $C_{0-10}$ alkyl)$_{1-2}$aminocarbonyloxy,
hydroxy $C_{0-10}$alkyl,
carboxyl $C_{0-10}$ alkyl,
$C_{1-10}$ alkylsulfonyl,
$C_{1-10}$ alkylsulfonylamino,
aryl $C_{1-10}$ alkylsulfonylamino,
$C_{3-8}$ heterocyclyl $C_{1-10}$ alkylsulfonylamino,
$C_{3-8}$ heterocycloalkyl $C_{1-10}$ alkylsulfonylamino,
$C_{3-8}$ cycloalkyl $C_{1-10}$ alkylsulfonylamino,
cyano,
nitro,
oxo,
perfluoro$C_{1-6}$alkyl, and
perfluoro$C_{1-6}$alkoxy,
wherein $R^7$ is optionally substituted with one or more groups chosen from hydrogen, OH, ($C_{1-6}$)alkoxy, halogen, $CO_2H$, CN, O(C=O)$C_1$-$C_6$ alkyl, $NO_2$, trifluoromethoxy, trifluoroethoxy, —$O_{(0-1)}(C_{1-10})$perfluoroalkyl, and $NH_2$; and
provided that when $R^2$ is phenyl and $R^3$ is furyl or pyridinyl, then $R^5$ is other than methyl.
Illustrative but nonlimiting examples of compounds of the invention are the following:
3-biphenyl-4-yl-1-(4-hydroxypyrimidin-2-yl)-8-[(3-methylpyridin-2-yl)methyl]-1,3,8-triazaspiro[4.5]decane-2,4-dione;

3-biphenyl-4-yl-8-[(3-methylpyridin-2-yl)methyl]-1-pyridin-2-yl-1,3,8-triazaspiro[4.5]decane-2,4-dione;

1-(4-hydroxypyrimidin-2-yl)-8-[(3-methylpyridin-2-yl)methyl]-3-phenyl-1,3,8-triazaspiro[4.5]decane-2,4-dione;

3-biphenyl-4-yl-8-[(3-methylpyridin-2-yl)methyl]-1-phenyl-1,3,8-triazaspiro[4.5]decane-2,4-dione;

2-{3-biphenyl-4-yl-8-[(3-methylpyridin-2-yl)methyl]-2,4-dioxo-1,3,8-triazaspiro[4.5]dec-1-yl}isonicotinic acid;

3-biphenyl-4-yl-1-(6-fluoropyridin-2-yl)-8-[(3-methylpyridin-2-yl)methyl]-1,3,8-triazaspiro[4.5]decane-2,4-dione;

6-{3-biphenyl-4-yl-8-[(3-methylpyridin-2-yl)methyl]-2,4-dioxo-1,3,8-triazaspiro[4.5]dec-1-yl}nicotinonitrile;

3-biphenyl-4-yl-8-[(3-methylpyridin-2-yl)methyl]-1-pyridin-4-yl-1,3,8-triazaspiro[4.5]decane-2,4-dione;

3-biphenyl-4-yl-1-(6-hydroxypyridazin-3-yl)-8-[(3-methylpyridin-2-yl)methyl]-1,3,8-triazaspiro[4.5]decane-2,4-dione;

3-biphenyl-4-yl-1-(5-hydroxypyrimidin-2-yl)-8-[(3-methylpyridin-2-yl)methyl]-1,3,8-triazaspiro[4.5]decane-2,4-dione;

3-biphenyl-4-yl-1-(6-methoxypyridin-2-yl)-8-[(3-methylpyridin-2-yl)methyl]-1,3,8-triazaspiro[4.5]decane-2,4-dione;

3-biphenyl-4-yl-1-(6-hydroxypyridin-2-yl)-8-[(3-methylpyridin-2-yl)methyl]-1,3,8-triazaspiro[4.5]decane-2,4-dione;

methyl 6-{3-biphenyl-4-yl-8-[(3-methylpyridin-2-yl)methyl]-2,4-dioxo-1,3,8-triazaspiro[4.5]dec-1-yl}pyridine-2-carboxylate;

6-{3-biphenyl-4-yl-8-[(3-methylpyridin-2-methyl]-2,4-dioxo-,3,8-triazaspiro[4.5]dec-1-yl}pyridine-2-carboxylic acid;

1-(4-methoxypyrimidin-2-yl)-8-[(3-methylpyridin-2-yl)methyl]-3-[4-(1H-tetrazol-5-yl)phenyl]-1,3,8-triazaspiro[4.5]decane-2,4-dione;

1-(4-hydroxypyrimidin-2-yl)-8-[(3-methylpyridin-2-yl)methyl]-3-[4-(1H-tetrazol-5-yl)phenyl]-1,3,8-triazaspiro[4.5]decane-2,4-dione;

4-{1-(4-hydroxypyrimidin-2-yl)-8-[(3-methylpyridin-2-yl)methyl]-2,4-dioxo-1,3,8-triazaspiro[4.5]dec-3-yl}benzoic acid;

3-biphenyl-4-yl-8-[(3-methylpyridin-2-yl)methyl]-1pyridin-1-yl-pyridin-3-yl-1,3,8-triazaspiro[4.5]decane-2,4-dione;

tert-butyl (2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)acetate;

tert-butyl (2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)acetate;

(2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)acetic acid;

3-(2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)propanoic acid;

(2-{[3-biphenyl-4-yl-1-(4-hydroxypyrimidin-2-yl)-2,4-dioxo-1,3,8-triazaspiro[4.5]dec-8-yl]methyl}-1H-imidazol-1-yl)acetic acid;

3-(2-{[3-biphenyl-4-yl-1-(4-hydroxypyrimidin-2-yl)-2,4-dioxo-1,3,8-triazaspiro[4.5]dec-8-yl]methyl}-1H-imidazol-1-yl)propanoic acid;

4-{1-(4-methoxypyrimidin-2-yl)-8-[(3-methylpyridin-2-yl)methyl]-2,4-dioxo-1,3,8-triazaspiro[4.5]dec-3-yl}benzonitrile;

ethyl 4-{1-(4-methoxypyrimidin-2-yl)-8-[(3-methylpyridin-2-yl)methyl]-2,4-dioxo-1,3,8-triazaspiro[4.5]dec-3-yl}benzoate;

3-biphenyl-4-yl-8-[(3-methylpyridin-2-yl)methyl]-1-(2-thienyl)-1,3,8-triazaspiro[4.5]decane-2,4-dione;

3-biphenyl-4-yl-8-[(3-bromopyridin-2-yl)methyl]-1-(4-methoxypyrimidin-2-yl)-1,3,8-triazaspiro[4.5]decane-2,4-dione;

3-biphenyl-4-yl-1-(4-methoxypyrimidin-2-yl)-8-[(3-methylpyridin-2-yl)methyl]-1,3,8-triazaspiro[4.5]decane-2,4-dione;

1-(4-methoxypyrimidin-2-yl)-8-[(3-methylpyridin-2-yl)methyl]-3-phenyl-1,3,8-triazaspiro[4.5]decane-2,4-dione;

3-biphenyl-4-yl-8-[(3-bromopyridin-2-yl)methyl]-1-(4-hydroxypyrimidin-2-yl)-1,3,8-triazaspiro[4.5]decane-2,4-dione;

4-[8-[(3-bromopyridin-2-yl)methyl]-1-(4-hydroxypyrimidin-2-yl)-2,4-dioxo-1,3,8-triazaspiro[4.5]dec-3-yl]-N-phenylbenzamide;

3-biphenyl-4-yl-1-(4-hydroxypyrimidin-2-yl)-8-[(3-methylpyridin-2-yl)methyl]-1,3,8-triazaspiro[4.5]decane-2,4-dione;

4-[8-[(3-bromopyridin-2-yl)methyl]-1-(4-hydroxypyrimidin-2-yl)-2,4-dioxo-1,3,8-triazaspiro[4.5]dec-3-yl]-N-cyclopropylbenzamide;

3-biphenyl-4-yl-8-[(3-bromopyridin-2-yl)methyl]-1-pyrimidin-2-yl-1,3,8-triazaspiro[4.5]decane-2,4-dione;

3-biphenyl-4-yl-8-[(3-bromopyridin-2-yl)methyl]-1-(4-hydroxypyrimidin-2-yl)-1,3,8-triazaspiro[4.5]decane-2,4-dione;

tert-butyl 2-{[3-biphenyl-4-yl-1-(4-methoxypyrimidin-2-yl)-2,4-dioxo-1,3,8-triazaspiro[4.5]dec-8-yl]methyl}nicotinate;

2-{[3-biphenyl-4-yl-1-(4-hydroxypyrimidin-2-yl)-2,4-dioxo-1,3,8-triazaspiro[4.5]dec-8-yl]methyl}nicotinic acid;

3-biphenyl-4-yl-1-(4-methoxypyrimidin-2-yl)-8-(H-tetrazol-5-ylmethyl)-1,3,8-triazaspiro[4.5]decane-2,4-dione;

2-{[3-biphenyl-4-yl-1-(4-methoxypyrimidin-2-yl)-2,4-dioxo-1,3,8-triazaspiro[4.5]dec-8-yl]methyl}nicotinonitrile;

3-biphenyl-4-yl-1-(4-methoxypyrimidin-2-yl)-8-[{(3-(H-tetrazol-5-yl)pyridin-2-yl]methyl}-1,3,8-triazaspiro[4.5]decane-2,4-dione;

3-biphenyl-4-yl-1-(2-hydroxypyrimidin-4-yl)-8-[(3-methylpyridin-2-yl)methyl]-1,3,8-triazaspiro[4.5]decane-2,4-dione;

3-biphenyl-4-yl-1-(3-hydroxypyridin-2-yl)-8-[(3-methylpyridin-2-yl)methyl]-1,3,8-triazaspiro[4.5]decane-2,4-dione;

4'-{1-(6-hydroxypyrimidin-4-yl)-8-[(3-methylpyridin-2-yl)methyl]-2,4-dioxo-1,3,8-triazaspiro[4.5]dec-3-yl}biphenyl-4-carboxylic acid;

3-biphenyl-4-yl-1-(5-hydroxypyrazin-2-yl)-8-[(3-methylpyridin-2-yl)methyl]-1,3,8-triazaspiro[4.5]decane-2,4-dione;

Butyl 4-{[3-biphenyl-4-yl-1-(4-hydroxypyrimidin-2-yl)-2,4-dioxo-1,3,8-triazaspiro[4.5]dec-8-yl]methyl}-1-H-imidazole-5-carboxylate;

Butyl 4-{[3-biphenyl-4-yl-1-(4-methoxypyrimidin-2-yl)-2,4-dioxo-1,3,8-triazaspiro[4.5]dec-8-yl]methyl}-1-H-imidazole-5-carboxylate;

Butyl 4-{[3-biphenyl-4-yl-1-(6-methoxypyrimidin-4-yl)-2,4-dioxo-1,3,8-triazaspiro[4.5]dec-8-yl]methyl}-1-H-imidazole-5-carboxylate;

3-biphenyl-4-yl-1-(4-methoxypyrimidin-2-yl)-8-[(5-methyl-1-H-imidazol-4-yl)methyl]-1,3,8-triazaspiro[4.5]decane-2,4-dione;

4-{[3-biphenyl-4-yl-1-(4-methoxypyrimidin-2-yl)-2,4-dioxo-1,3,8-triazaspiro[4.5]dec-8-yl]methyl}-1-H-imidazole-5-carboxylic acid;

4-[(3-biphenyl-4-yl-2,4-dioxo-1,3,8-triazaspiro[4.5]dec-8-yl)methyl]-1-H-imidazole-5-carboxylic acid;
4-{[3-biphenyl-4-yl-1-(6-hydroxypyrimidin-4-yl)-2,4-dioxo-1,3,8-triazaspiro[4.5]dec-8-yl]methyl}-1-H-imidazole-5-carboxylic acid;
3-biphenyl-4-yl-1-(6-hydroxypyrimidin-4-yl)-8-[(5-methyl-1-H-imidazol-4-yl)methyl]-1,3,8-triazaspiro[4.5]decane-2,4-dione;
2-{[3-biphenyl-4-yl-1-(6-hydroxypyrimidin-4-yl)-2,4-dioxo-1,3,8-triazaspiro[4.5]dec-8-yl]methyl}nicotinic acid;
3-biphenyl-4-yl-1-(4,6-dihydroxypyrimidin-2-yl)-8-[(3-methylpyridin-2-yl)methyl]-1,3,8-triazaspiro[4.5]decane-2,4-dione;
3-biphenyl-4-yl-1-(4-hydroxy-6-methoxypyrimidin-2-yl)-8-[(3-methylpyridin-2-yl)methyl]-1,3,8-triazaspiro[4.5]decane-2,4-dione;
3-biphenyl-4-yl-1-(4,6-dimethoxypyrimidin-2-yl)-8-[(3-methylpyridin-2-yl)methyl]-1,3,8-triazaspiro[4.5]decane-2,4-dione;
3-biphenyl-4-yl-1-(2-hydroxypyridin-4-yl)-8-[(3-methylpyridin-2-yl)methyl]-1,3,8-triazaspiro[4.5]decane-2,4-dione;
2-{3-biphenyl-4-yl-8-[(3-methylpyridin-2-yl)methyl]-2,4-dioxo-1,3,8-triazaspiro[4.5]dec-1-yl}pyrimidine-4-carboxylic acid;
6-{3-biphenyl-4-yl-8-[(3-methylpyridin-2-yl)methyl]-2,4-dioxo-1,3,8-triazaspiro[4.5]dec-1-yl}nicotinic acid;
Methyl 4'-{8-[(3-methylpyridin-2-yl)methyl]-2,4-dioxo-1-pyrimidin-2-yl-1,3,8-triazaspiro[4.5]dec-3-yl}biphenyl-4-carboxylate;
Methyl 4-[(3-biphenyl-4-yl-2,4-dioxo-1-pyrimidin-2-yl-1,3,8-triazaspiro[4.5]dec-8-yl)methyl]-1-H-imidazole-5-carboxylate;
4'-{8-[(3-methylpyridin-2-yl)methyl]-2,4-dioxo-1-pyrimidin-2-yl-1,3,8-triazaspiro[4.5]dec-3-yl}biphenyl-4-carboxylic acid;
4-[(3-biphenyl-4-yl-2,4-dioxo-1-pyrimidin-2-yl-1,3,8-triazaspiro[4.5]dec-8-yl)methyl]-1-H-imidazole-5-carboxylic acid;
5-(4-{8-[(3-carboxypyridin-2-yl)methyl]-2,4-dioxo-1-pyrimidin-2-yl-1,3,8-triazaspiro[4.5]dec-3-yl}phenyl)pyridine-2-carboxylic acid;
4'-{8-[(3-methylpyridin-2-yl)methyl]-2,4-dioxo-1-pyrimidin-2-yl-1,3,8-triazaspiro[4.5]dec-3-yl}biphenyl-3-carboxylic acid;
(4'-{8-[(3-methylpyridin-2-yl)methyl]-2,4-dioxo-1-pyrimidin-2-yl-1,3,8-triazaspiro[4.5]dec-3-yl}biphenyl-4-yl)acetic acid;
3-biphenyl-4-yl-8-[(3-methylpyridin-2-yl)methyl]-1-pyrimidin-4-yl-1,3,8-triazaspiro[4.5]decane-2,4-dione;
2-(4-{8-[(3-methylpyridin-2-yl)methyl]-2,4-dioxo-1-pyrimidin-2-yl-1,3,8-triazaspiro[4.5]dec-3-yl}phenyl)cyclopropanecarboxylic acid;
8-[(3-methylpyridin-2-yl)methyl]-1-(6-methoxypyrimidin-4-yl)-3-(4'-propionylbiphenyl-4-yl)-1,3,8-triazaspiro[4.5]decane-2,4-dione;
1-(6-hydroxypyrimidin-4-yl)-8-[(3-methylpyridin-2yl)methyl]-3-(4'-propionylbiphenyl-4-yl)-1,3,8-triazaspiro[4.5]decane-2,4-dione;
3-biphenyl-4-yl-1-methyl-8-[(3-methylpyridin-2-yl)methyl]-1,3,8-triazaspiro[4.5]decane-2,4-dione;
tert-butyl (3-biphenyl-4-yl-2,4-dioxo-1-pyrazin-2-yl-1,3,8-triazaspiro[4.5]dec-8-yl)acetate;
(3-biphenyl-4-yl-2,4-dioxo-1-pyrazin-2-yl-1,3,8-triazaspiro[4.5]dec-8-yl)acetic acid;
(3-biphenyl-4-yl-2,4-dioxo-1-pyrimidin-5-yl-1,3,8-triazaspiro[4.5]dec-8-yl)acetic acid(3-biphenyl-4-yl-2,4-dioxo-1-pyrimidin-2-yl-1,3,8-triazaspiro[4.5]dec-8-yl)acetic acid;
[3-biphenyl-4-yl-1-(4-methoxypyrimidin-2-yl)-2,4-dioxo-1,3,8-triazaspiro[4.5]dec-8-yl]acetic acid;
2,2'-(3-biphenyl-4-yl-2,4-dioxo-1,3,8-triazaspiro[4.5]decane-1,8-diyl)diacetic acid;
[3-biphenyl-4-yl-1-(2-ethoxy-2-oxoethyl)-2,4-dioxo-1,3,8-triazaspiro[4.5]dec-8-yl]acetic acid;
3-biphenyl-4-yl-8-[(3-methylpyridin-2-yl)methyl]-1,3,8-triazaspiro[4.5]decane-2,4-dione;
(3-biphenyl-4-yl-2,4-dioxo-1,3,8-triazaspiro[4.5]dec-8-yl)acetic acid;
ethyl 3-biphenyl-4-yl-1-(4-methoxypyrimidin-2-yl)-8-[(3-methylpyridin-2-yl)methyl]-2,4-dioxo-1,3,8-triazaspiro[4.5]decane-6-carboxylate;
ethyl 3-biphenyl-4-yl-1-(4-hydroxypyrimidin-2-yl)-8-[(3-methylpyridin-2-yl)methyl]-2,4-dioxo-1,3,8-triazaspiro[4.5]decane-6-carboxylate;
3-biphenyl-4-yl-1-(4-hydroxypyrimidin-2-yl)-8-[(3-methylpyridin-2-yl)methyl]-2,4-dioxo-1,3,8-triazaspiro[4.5]decane-6-carboxylic acid;
3-biphenyl-4-yl-8-[(3-methylpyridin-2-yl)methyl]-2,4-dioxo-1,3,8-triazaspiro[4.5]decane-6-carboxylic acid;
Ethyl 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylate;
3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid;
3-biphenyl-4-yl-8-[(3-methylpyridin-2-yl)methyl]-2,4-dioxo-1-pyrimidin-2-yl-1,3,8-triazaspiro[4.5]decane-6-carboxylic acid;
Ethyl 3-biphenyl-4-yl-1-(6-methoxypyrimidin-4-yl)-8-[(3-methylpyridin-2-yl)methyl]-2,4-dioxo-1,3,8-triazaspiro[4.5]decane-6-carboxylate;
Ethyl 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylate;
3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid;
3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid;
ethyl [({3-biphenyl-4-yl-8-[(3-methylpyridin-2-yl)methyl]-2,4-dioxo-1,3,8-triazaspiro[4.5]dec-6-yl}carbonyl)amino]acetate;
tert-butyl [({3-biphenyl-4-yl-8-[(3-methylpyridin-2-yl)methyl]-2,4-dioxo-1,3,8-triazaspiro[4.5]dec-6-yl}carbonyl)amino]acetate;
[({3-biphenyl-4-yl-8-[(3-methylpyridin-2-yl)methyl]-2,4-dioxo-1,3,8-triazaspiro[4.5]dec-6-yl}carbonyl)amino]acetic acid;
2-[({3-biphenyl-4-yl-8-[(3-methylpyridin-2-yl)methyl]-2,4-dioxo-1,3,8-triazaspiro[4.5]dec-1-yl}carbonyl)amino]-2-methylpropanoic acid;
(2R)-2-[({3-biphenyl-4-yl-8-[(3-methylpyridin-2-yl)methyl]-2,4-dioxo-1,3,8-triazaspiro[4.5]dec-1-yl}carbonyl)amino]propanoic acid;
(2S)-2-[({3-biphenyl-4-yl-8-[(3-methylpyridin-2-yl)methyl]-2,4-dioxo-1,3,8-triazaspiro[4.5]dec-1-yl}carbonyl)amino]propanoic acid;
N-({3-biphenyl-4-yl-8-[(3-methylpyridin-2-yl)methyl]-2,4-dioxo-1,3,8-triazaspiro[4.5]dec-1-yl}carbonyl)-L-serine;

4-{3-biphenyl-4-yl-8-[(3-methylpyridin-2-yl)methyl]-2,4-dioxo-1,3,8-triazaspiro[4.5]dec-1-yl}-4-oxobutanoic acid;

4'-{1-(6-methoxypyrimidin-4-yl)-8-[(3-methylpyridin-2-yl)methyl]-2,4-dioxo-1,3,8-triazaspiro[4.5]dec-3-yl}biphenyl-4-carboxylic acid;

4'-{1-(6-methoxypyrimidin-4-yl)-8-[(3-methylpyridin-2-yl)methyl]-2,4-dioxo-1,3,8-triazaspiro[4.5]dec-3-yl}-2-methylbiphenyl-4-carboxylic acid;

4'-{1-(6-methoxypyrimidin-4-yl)-8-[(3-methylpyridin-2-yl)methyl]-2,4-dioxo-1,3,8-triazaspiro[4.5]dec-3-yl}-3-methylbiphenyl-4-carboxylic acid;

2-fluoro-4'-{1-(6-methoxypyrimidin-4-yl)-8-[(3-methylpyridin-2-yl)methyl]-2,4-dioxo-1,3,8-triazaspiro[4.5]dec-3-yl}biphenyl-4-carboxylic acid;

2-methyl-4'-{8-[(3-methylpyridin-2-yl)methyl]-2,4-dioxo-1-pyrazin-2-yl-1,3,8-triazaspiro[4.5]dec-3-yl}biphenyl-4-carboxylic acid;

2-methyl-4'-{1-(6-methylpyrazin-2-yl)-8-[(3-methylpyridin-2-yl)methyl]-2,4-dioxo-1,3,8-triazaspiro[4.5]dec-3-yl}biphenyl-4-carboxylic acid;

4'-{1-(6-methylpyrazin-2-yl)-8-[(3-methylpyridin-2-yl)methyl]-2,4-dioxo-1,3,8-triazaspiro[4.5]dec-3-yl}biphenyl-4-carboxylic acid;

2-methyl-4'-[8-[(3-methylpyridin-2-yl)methyl]-1-(6-methylpyrimidin-4-yl)-2,4-dioxo-1,3,8-triazaspiro[4.5]dec-3-yl]biphenyl-4-carboxylic acid;

4'-[8-[(3-methylpyridin-2-yl)methyl]-1-(6-methylpyrimidin-4-yl)-2,4-dioxo-1,3,8-triazaspiro[4.5]dec-3-yl]biphenyl-4-carboxylic acid;

2-methyl-4'-{8-[(3-methylpyridin-2-yl)methyl]-2,4-dioxo-1-[6-(trifluoromethyl)pyrimidin-4-yl]-1,3,8-triazaspiro[4.5]dec-3-yl}biphenyl-4-carboxylic acid;

1-(6-methoxypyrimidin-4-yl)-8-[(3-methylpyridin-2-yl)methyl]-3-[4'-(1H-pyrazol-5-yl) biphenyl-4-yl]-1,3,8-triazaspiro[4.5]decane-2,4-dione;

1-(6-hydroxypyrimidin-4-yl)-8-[(3-methylpyridin-2-yl)methyl]-3-[4'-(1H-pyrazol-5-yl) biphenyl-4-yl]-1,3,8-triazaspiro[4.5]decane-2,4-dione;

1-(6-methoxypyrimidin-4-yl)-8-[(3-methylpyridin-2-yl)methyl]-3-[4'-(5-oxopyrazolidin-3-yl) biphenyl-4-yl]-1,3,8-triazaspiro[4.5]decane-2,4-dione;

1-(6-hydroxypyrimidin-4-yl)-8-[(3-methylpyridin-2-yl)methyl]-3-[4'-(1 morpholin-4-yl) biphenyl-4-yl]-1,3,8-triazaspiro[4.5]decane-2,4-dione;

4-(6-{3-(4-bromophenyl)-8-[(3-methylpyridin-2-yl)methyl]-2,4-dioxo-1,3,8-triazaspiro[4.5]dec-1-yl}pyrimidin-4-yl)benzoic acid;

4'-{8-[(3-methylpyridin-2-yl)methyl]-2,4-dioxo-1-pyrimidin-4-yl-1,3,8-triazaspiro[4.5]dec-3-yl}biphenyl-4-carboxylic acid;

methyl 2-methyl-4'-{8-[(3-methylpyridin-2-yl)methyl]-2,4-dioxo-1-pyrimidin-4-yl-1,3,8-triazaspiro[4.5]dec-3-yl}biphenyl-4-carboxylate;

2-methyl-4'-{8-[(3-methylpyridin-2-yl)methyl]-2,4-dioxo-1-pyrimidin-4-yl-1,3,8-triazaspiro[4.5]dec-3-yl}biphenyl-4-carboxylic acid;

2-methyl-4'-[8-[(3-methylpyridin-2-yl)methyl]-1-(2-methylpyrimidin-4-yl)-2,4-dioxo-1,3,8-triazaspiro[4.5]dec-3-yl]biphenyl-4-carboxylic acid;

2-methyl-4'-{8-[(3-methylpyridin-2-yl)methyl]-2,4-dioxo-1-pyridazin-3-yl-1,3,8-triazaspiro[4.5]dec-3-yl}biphenyl-4-carboxylic acid;

4-(5-{1-(6-methoxypyrimidin-4-yl)-8-[(3-methylpyridin-2-yl)methyl]-2,4-dioxo-1,3,8-triazaspiro[4.5]dec-3-yl}-pyridin-2-yl)benzoic acid;

4-(5-{1-(4-methoxypyrimidin-2-yl)-8-[(3-methylpyridin-2-yl)methyl]-2,4-dioxo-1,3,8-triazaspiro[4.5]dec-3-yl}-pyridin-2-yl)benzoic acid;

4-(5-{8-[(4-methoxypyridin-2-yl)methyl]-1-(6-methoxypyrimidin-4-yl)-2,4-dioxo-1,3,8-triazaspiro[4.5]dec-3-yl}-pyridin-2-yl)benzoic acid;

4-(5-{8-[(4-hydroxypyridin-2-yl)methyl]-1-(6-methoxypyrimidin-4-yl)-2,4-dioxo-1,3,8-triazaspiro[4.5]dec-3-yl}-pyridin-2-yl)benzoic acid;

4-(5-{1-(6-methoxypyrimidin-4-yl)-8-[(3-methylpyridin-2-yl)methyl]-2,4-dioxo-1,3,8-triazaspiro[4.5]dec-3-yl}-pyridin-2-yl)-3-methylbenzoic acid;

4-(5-{1-(4-methoxypyrimidin-2-yl)-8-[(3-methylpyridin-2-yl)methyl]-2,4-dioxo-1,3,8-triazaspiro[4.5]dec-3-yl}-pyridin-2-yl)-3-methylbenzoic acid;

3-methyl-4-(5-{8-[(3-methylpyridin-2-yl)methyl]-2,4-dioxo-1-(2,2,2-trifluoroethyl)-1,3,8-triazaspiro[4.5]dec-3-yl}-pyridin-2-yl)benzoic acid;

3-fluoro-4-(5-{1-(6-methoxypyrimidine-4-yl)-8-[(3-methylpyridin-2-yl)methyl]-2,4-dioxo-1,3,8-triazaspiro[4.5]dec-3-yl}pyridin-2-yl)-3-benzoic acid;

or a pharmaceutically acceptable salt thereof, or a stereoisomer thereof, or a pharmaceutically acceptable salt of the stereoisomer thereof.

One embodiment of the invention provides compounds of formula II or a pharmaceutically acceptable salt thereof, or a stereoisomer thereof, or a pharmaceutically acceptable salt of the stereoisomer thereof:

II wherein
n is 0, 1, 2, 3 or 4;
$R^2$ is selected from:
  hydrogen,
  aryl($C_0$-$C_6$)alkyl,
  heterocyclyl($C_0$-$C_6$)alkyl;
  $C_{0-10}$ alkyl(oxy)$_{0-1}$carbonyl$C_{1-10}$ alkyl;
  $C_{0-10}$ alkylamino carbonyl$C_{1-10}$ alkyl,
  arylamino carbonyl$C_{1-10}$ alkyl,
  $C_{3-8}$ cycloalkyl amino carbonyl$C_{0-10}$ alkyl,
  ($C_{3-8}$)heterocyclyl amino carbonyl$C_{1-10}$ alkyl,
  ($C_{3-8}$heterocycloalkyl amino carbonyl $C_{0-10}$ alkyl, and
  $C_{0-10}$ alkyloxycarbonylamino carbonyl$C_{0-10}$ alkyl;
$R^3$ is —($C_0$-$C_6$ alkyl)C(O)O($C_0$-$C_{10}$ alkyl), or —($C_0$-$C_6$ alkyl)heterocyclyl;
optionally, $R^2$ and $R^3$ are each independently substituted by 1, 2, 3, or 4 $R^6$;
$R^4$ is selected from hydrogen, $C_1$-$C_3$ alkyl, and oxo;
$R^5$ is selected from hydrogen, —$C_1$-$C_{10}$ alkyl, —O$C_1$-$C_{10}$ alkyl, —($C_0$-$C_6$ alkyl)C(O)O($C_0$-$C_6$ alkyl), OH, —$C_1$-$C_4$ haloalkyl optionally substituted with one to five fluorine, halogen, $NH_2$, $N(C_1$-$C_6$ alkyl)$_2$, $NO_2$, CN, and —$S(O)_{1-2}$;
$R^6$ is chosen from:
  halogen,
  (carbonyl)$_{0-1}C_{1-10}$ alkyl,
  (carbonyl)$_{0-1}C_{2-10}$ alkenyl,
  (carbonyl)$_{0-1}$ $C_{2-10}$ alkynyl,
  $C_{1-10}$ alkenylamino, $C_{1-10}$ alkyl(carbonyl)$_{0-1}$ $C_{0-10}$ alkyl,
$C_{0-10}$ alkyl(carbonyl)$_{0-1}$aryl $C_{0-10}$ alkyl,
$C_{0-10}$ alkyl(carbonyl)$_{0-1}$$C_{3-8}$ cycloalkyl $CO_{0-10}$ alkyl,
$C_{0-10}$ alkyl(carbonyl)$_{0-1}$($C_{3-8}$)heterocyclyl $C_{0-10}$ alkyl,
$C_{0-10}$ alkyl(carbonyl)$_{0-1}$($C_{3-8}$ heterocycloalkyl $C_{0-10}$ alkyl,
$C_{1-4}$acylamino $C_{0-10}$ alkyl,
di-($C_{1-10}$ alkyl)amino $C_{0-10}$ alkyl,
aryl$C_{0-10}$ alkylamino $C_{0-10}$ alkyl,
(aryl$C_{0-10}$ alkyl)$_2$amino $C_{0-10}$ alkyl,
$C_{3-8}$ cycloalkyl $CO_{0-10}$ alkylamino $C_{0-10}$ alkyl,
$C_{3-8}$ heterocyclyl $C_{0-10}$ alkylamino $C_{0-10}$ alkyl,
$C_{3-8}$ heterocycloalkyl $CO_{0-10}$ alkylamino $C_{0-10}$ alkyl,
($C_{3-8}$ cycloalkyl $C_{0-10}$ alkyl)$_2$amino $C_{0-10}$ alkyl,
($C_{3-8}$ heterocyclyl $C_{0-10}$ alkyl)$_2$amino $C_{0-10}$ alkyl,
($C_{3-8}$ heterocycloalkyl $C_{0-10}$ alkyl)$_2$amino $C_{0-10}$ alkyl,
($C_{0-10}$ alkyl)$_2$aminocarbonyl $C_{0-10}$ alkyl,
(aryl $C_{0-10}$ alkyl)$_{1-2}$-aminocarbonyl $C_{0-10}$ alkyl,
$C_{0-10}$ alkyl amino(carbonyl)$_{0-1}$ $C_{0-10}$ alkyl,
$C_{3-8}$ cycloalkyl $C_{0-10}$ alkyl amino(carbonyl)$_{0-1}$$C_{0-10}$ alkyl,
$C_{3-8}$ heterocyclyl $C_{0-10}$ alkyl amino(carbonyl)$_{0-1}$$C_{0-10}$ alkyl,
$C_{3-8}$ heterocycloalkyl $C_{0-10}$ alkyl amino(carbonyl)$_{0-1}$ $C_{0-10}$ alkyl,
aryl $C_{0-10}$ alkyl amino(carbonyl)$_{0-1}$$C_{0-10}$ alkyl,
$C_{3-8}$ cycloalkyl $C_{0-10}$ alkyl carbonylamino $C_{0-10}$ alkyl,
$C_{3-8}$ heterocyclyl $C_{0-10}$ alkyl carbonylamino $C_{0-10}$ alkyl,
$C_{3-8}$ heterocycloalkyl $C_{0-10}$ alkyl carbonylamino $C_{0-10}$ alkyl,
aryl $C_{0-10}$ alkyl carbonylamino $C_{0-10}$ alkyl,
$C_{1-10}$ alkoxy (carbonyl)$_{0-1}$$C_{0-10}$ alkyl,
$C_{0-10}$ alkylcarboxy $C_{0-10}$ alkylamino,
carboxyl $C_{0-10}$ alkyl,
carboxyl aryl,
carboxyl $C_{3-8}$ cycloalkyl,
carboxyl $C_{3-8}$ heterocyclyl,
carboxyl $C_{3-8}$ heterocycloalkyl,
$C_{1-10}$ alkoxy,
$C_{1-10}$alkyloxy $C_{0-10}$alkyl,
$C_{1-10}$ alkyl(carbonyl)$_{0-1}$oxy,
$C_{3-8}$ heterocyclyl $C_{0-10}$ alkyl(carbonyl)$_{0-1}$oxy,
$C_{3-8}$ heterocycloalkyl $C_{0-10}$ alkyl(carbonyl)$_{0-1}$oxy,
$C_{3-8}$ cycloalkyl $C_{0-10}$ alkyl(carbonyl)$_{0-1}$oxy,
aryl $C_{0-10}$ alkyl(carbonyl)$_{0-1}$oxy,
hydroxy $C_{0-1}$alkyl,
hydroxycarbonyl$C_{0-10}$alkoxy,
hydroxycarbonyl$C_{0-10}$alkyloxy,
$C_{1-10}$ alkylthio,
cyano,
Oxo,
nitro,
perfluoro$C_{1-6}$alkyl, and
perfluoro$C_{1-6}$alkoxy, and
wherein $R^6$ is optionally substituted with 1, 2, 3, or 4 substituents, $R^7$, chosen from:
halogen,
(carbonyl)$_{0-1}$$C_{1-10}$ alkyl,
(carbonyl)$_{0-1}$$C_{2-10}$ alkenyl,
(carbonyl)$_{0-1}$$C_{2-10}$ alkynyl,
$C_{1-10}$ alkylcarbonyl,
$C_{2-10}$ alkenylcarbonyl,
$C_{2-10}$ alkynylcarbonyl,
(carbonyl)$_{0-1}$aryl $C_{0-10}$ alkyl,
(carbonyl)$_{0-1}$($C_{3-8}$)heterocyclyl $C_{0-10}$ alkyl,
aryl $C_{0-10}$ alkylcarbonyl,
($C_{3-8}$)heterocyclylcarbonyl,
($C_{3-8}$) heterocycloalkylcarbonyl;
$C_{3-8}$ cycloalkyl $C_{0-10}$ alkyl,
(carbonyl)$_{0-1}$($C_{3-8}$)heterocycloalkyl $C_{0-10}$ alkyl,
$C_{1-4}$acylamino $C_{0-10}$ alkyl,
$C_{0-10}$ alkylamino $C_{0-10}$ alkyl,
di-($C_{1-10}$ alkyl)amino $C_{0-10}$alkyl,
aryl$C_{0-10}$ alkylamino $C_{0-10}$ alkyl,
(aryl$C_{0-10}$ alkyl)$_2$amino $C_{0-10}$ alkyl,
$C_{3-8}$ cycloalkyl $C_{0-10}$ alkylamino $C_{0-10}$ alkyl,
$C_{3-8}$ heterocyclyl $C_{0-10}$ alkylamino $C_{0-10}$ alkyl,
$C_{3-8}$ heterocycloalkyl $C_{0-10}$ alkylamino $C_{0-10}$ alkyl,
($C_{1-10}$ alkyl)$_2$aminocarbonyl,
arylaminocarbonyl,
$C_{3-8}$ heterocyclylaminocarbonyl,
$C_{1-10}$ alkylaminocarbonyl
$C_{1-10}$ alkoxy (carbonyl)$_{0-1}$$C_{0-10}$ alkyl,
$C_{1-10}$ alkyloxy $C_{0-10}$alkyl,
($C_{1-10}$ alkyl)$_2$aminocarbonyloxy,
hydroxycarbonyl$C_{0-1}$alkoxy,
($C_{1-10}$ alkyl)$_2$aminocarbonyloxy,
(aryl $C_{0-10}$ alkyl)$_{1-2}$aminocarbonyloxy,
hydroxy $C_{0-10}$alkyl,
carboxyl $C_{0-10}$ alkyl,
$C_{1-10}$ alkylsulfonyl,
$C_{1-10}$ alkylsulfonylamino,
aryl $C_{1-10}$ alkylsulfonylamino,
$C_{3-8}$ heterocyclyl $C_{1-10}$ alkylsulfonylamino,
$C_{3-8}$ heterocycloalkyl $C_{1-10}$ alkylsulfonylamino,
$C_{3-8}$ cycloalkyl $C_{1-10}$ alkylsulfonylamino,
cyano,
nitro,
oxo,
perfluoro$C_{1-6}$alkyl, and
perfluoro$C_{1-6}$alkoxy,
wherein $R^7$ is optionally substituted with one or more groups chosen from hydrogen, OH, ($C_{1-6}$)alkoxy, halogen, $CO_2H$, CN, O(C=O)$C_1$-$C_6$ alkyl, $NO_2$, trifluoromethoxy, trifluoroethoxy, $—O_{(0-1)}(C_{1-10})$perfluoroalkyl, and $NH_2$; and
provided that when $R^2$ is phenyl and $R^3$ is furyl or pyridinyl, then $R^5$ is other than methyl.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2$ $CH_3$, butyl may be represented by "Bu" or $CH_2CH_2$ $CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

Unless otherwise specifically noted as only "unsubstituted" or only "substituted", or when substituents are enumerated, alkyl (either as a stand alone radical or as part of a radical such as alkoxy, alkylthio and aralkyl) groups are unsubstituted or substituted with 1 to 3 substituents on each carbon atom, with halo, $C_1$-$C_{20}$ alkyl, $CF_3$, $NH_2$, N($C_1$-$C_6$ alkyl)$_2$, NO$_2$, oxo, CN, N$_3$, —OH, —O(C$_1$-C$_6$ alkyl), C$_3$-C$_{10}$ cycloalkyl, C$_2$-C$_6$ alkenyl, C$_2$-C$_6$ alkynyl, (C$_0$-C$_6$ alkyl)S(O)$_{0-2}$—, (C$_0$-C$_6$ alkyl)S(O)$_{0-2}$(C$_0$-C$_6$ alkyl)-, (C$_0$-C$_6$ alkyl)C(O)NH—, H$_2$N—C(NH)—, —O(C$_1$-C$_6$ alkyl)CF$_3$, (C$_0$-C$_6$ alkyl)C(O)—, (C$_0$-C$_6$ alkyl)OC(O)—, (C$_0$-C$_6$ alkyl)O(C$_1$-C$_6$ alkyl)-, (C$_0$-C$_6$ alkyl)C(O)$_{1-2}$(C$_0$-C$_6$ alkyl)-, (C$_0$-C$_6$ alkyl)OC(O)NH—, —NH(C$_1$-C$_6$ alkyl)NHC(O)NH(C$_1$-C$_6$ alkyl), NHC(O)OC$_1$-C$_6$ alkyl, —NH(C$_1$-C$_6$ alkyl)NHSO$_2$(C$_1$-C$_6$ alkyl), —(C$_0$-C$_6$ alkyl)NHSO$_2$(C$_1$-C$_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "C$_0$" as employed in expressions such as "C$_{0-6}$ alkyl" means a direct covalent bond; or when the term appears at the terminus of a substituent, C$_{0-6}$ alkyl means hydrogen or C$_{1-6}$alkyl. Similarly, when an integer defining the presence of a certain number of atoms in a group is equal to zero, it means that the atoms adjacent thereto are connected directly by a bond. For example, in the structure

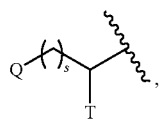

wherein s is an integer equal to zero, 1 or 2, the structure is

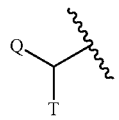

when s is zero.

The term "C$_{3-8}$ cycloalkyl" (or "C$_3$-C$_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "C$_{3-7}$ cycloalkyl", "C$_{3-6}$ cycloalkyl", "C$_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenyl.

The term "carbocycle" (and variations thereof such as "carbocyclic" or "carbocyclyl") as used herein, unless otherwise indicated, refers to (i) a C$_3$ to C$_8$ monocyclic, saturated or unsaturated ring or (ii) a C$_7$ to C$_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a C$_7$ to C$_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with C$_{1-6}$ alkyl, C$_{1-6}$ alkenyl, C$_{1-6}$ alkynyl, aryl, halogen, NH$_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

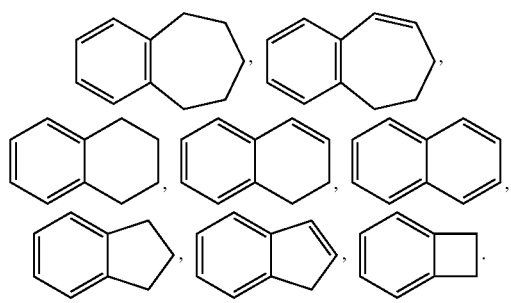

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Non limiting examples of heterocylylic moieties include, but are not limited to, the following: azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoauinlinvy, isoquinolinyl, 2,3-dihydrobezofuryl, 2,3-dihydrobenzo-1,4-dioxinyl (i.e.,

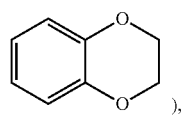

), imidazo(2,1-b)(1,3)thiazole, (i.e.,

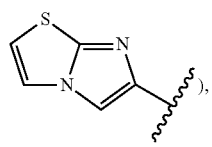

), and benzo-1,3-dioxolyl (i.e.,

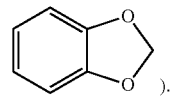

).

In certain contexts herein,

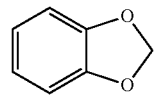

is alternatively referred to as phenyl having as a substituent methylenedioxy attached to two adjacent carbon atoms.

The terms "arylalkyl" and "alkylaryl" include an alkyl portion where alkyl is as defined above and include an aryl portion where aryl is as defined above. Examples of arylalkyl include, but are not limited to, benzyl, phenylethyl, phenylpropyl, naphthylmethyl, and naphthylethyl. Examples of alkylaryl include, but are not limited to, toluene, ethylbenzene, propylbenzene, methylpyridine, ethylpyridine, propylpyridine and butylpyridine.

Unless otherwise specifically noted as only "unsubstituted" or only "substituted", or when substituents are specifically enumerated, cycloalkyl, aryl (including phenyl) and heterocycle (including heteroaryl) groups are unsubstituted or substituted. As used herein, the terms "substituted $C_3$-$C_{10}$ cycloalkyl", "substituted aryl (including phenyl)" and "substituted heterocycle" are intended to include the cyclic group containing from 1 to 3 substituents in addition to the point of attachment to the rest of the compound. Preferably, the substituents are selected from the group which includes, but are not limited to, halo, $C_1$-$C_{20}$ alkyl, $CF_3$, $NH_2$, $N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)$_2$NC(O)—($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

When any variable (e.g., $R^2$, $R^3$, etc.) occurs more than one time in any substituent or in formulas I-III, its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

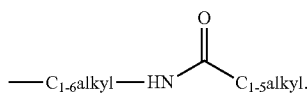

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

In one embodiment of the invention, $R^1$, is selected from, but is not limited to, the following: phenyl, naphthyl, tetrahydro-naphthyl, indanyl, 2,3-dihydro-1H-indenyl, biphenyl, azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl, wherein $R^1$ is optionally substituted with 1, 2, 3, or 4 $R^6$ substituents.

In one embodiment of the invention, $R^1$, is selected from: phenyl, naphthyl, tetrahydro-naphthyl, and biphenyl, wherein $R^1$ is optionally substituted with 1, 2, 3, or 4 $R^6$ substituents. In a variant of this embodiment, $R^1$, is phenyl, or biphenyl; and optionally substituted with 1, 2, 3, or 4 $R^6$.

In another embodiment, $R^1$ is selected from: benzofuryl, benzofurazanyl, benzothiazolyl, benzothienyl, benzotriazolyl, benzothiophenyl, benzoxazolyl, carbazolyl, furanyl, imidazolyl, indolinyl, indolyl, indolazinyl, indazolyl, isobenzofuryl, isoindolyl, isoquinolyl, isothiazolyl, isoxazolyl, oxadiazolyl, oxazolyl, pyranyl, pyrazinyl, pyrazolyl, pyridazinyl, pyridazinyl, pyridinyl, pyrimidyl, pyrrolyl, tetrazolyl, tetrazolopyridyl, thiadiazolyl, thiazolyl, thienyl, triazolyl, piperazinyl, piperidinyl, pyrrolidinyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydrotetrazolyl, dihydrothiadiazolyl, dihydrothiazolyl, dihydrothienyl, dihydrotriazolyl, dihydroazetidinyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl, wherein $R^1$ is optionally substituted with 1, 2, 3, or 4 $R^6$ substituents.

In one embodiment of the invention, $R^2$ is selected from hydrogen, aryl($C_0$-$C_6$)alkyl, heterocyclyl($C_0$-$C_6$)alkyl, $C_{0-10}$ alkyl(oxy)$_{0-10}$carbonyl$C_{0-10}$alkyl, $C_{3-8}$ cycloalkyl amino carbonyl$C_{0-10}$ alkyl, and $C_{0-10}$ alkyloxycarbonylamino carbonyl$C_{0-10}$ alkyl, wherein $R^2$ is optionally substituted with 1, 2, 3, or 4 $R^6$.

In a variant of this invention, heterocyclyl in $R^2$ is selected from, but is not limited to: azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl, wherein $R^2$ is optionally substituted with 1, 2, 3, or 4 $R^6$ substituents.

In another embodiment of the invention, heterocyclyl in $R^2$ is selected from: benzothienyl, benzotriazolyl, benzothiophenyl, benzoxazolyl, furanyl, imidazolyl, indolinyl, indolyl, indolazinyl, indazolyl, isobenzofuryl, isoindolyl, isoquinolyl, isothiazolyl, isoxazolyl, oxadiazolyl, oxazolyl, oxazoline, isoxazoline, pyranyl, pyrazinyl, pyrazolyl, pyridazinyl, pyridopyridinyl, pyridazinyl, pyridinyl, pyrimidyl, pyrrolyl, quinazolinyl, quinolyl, tetrazolyl, thiadiazolyl, thiazolyl, thienyl, triazolyl, piperazinyl, piperidinyl, pyrrolidinyl, tetrahydroquinolinyl, tetrahydroisoquinolinyl, tetrahydrothienyl, and benzo-1,3-dioxolyl, wherein $R^2$ is optionally substituted with 1, 2, 3, or 4 $R^6$ substituents.

In one embodiment of the invention, $R^3$, is selected from, but is not limited to, the following: phenyl, naphthyl, tetrahydro-naphthyl, indanyl, 2,3-dihydro-1H-indenyl, biphenyl, azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl, wherein $R^3$ is optionally substituted with 1, 2, 3, or 4 $R^6$ substituents.

In another embodiment of the invention, heterocyclyl in $R^3$ is selected from: benzothienyl, benzotriazolyl, benzothiophenyl, benzoxazolyl, furanyl, imidazolyl, indolinyl, indolyl, indolazinyl, indazolyl, isobenzofuryl, isoindolyl, isoquinolyl, isothiazolyl, isoxazolyl, oxadiazolyl, oxazolyl, oxazoline, isoxazoline, pyranyl, pyrazinyl, pyrazolyl, pyridazinyl, pyridopyridinyl, pyridazinyl, pyridinyl, pyrimidyl, pyrrolyl, quinazolinyl, quinolyl, tetrazolyl, thiadiazolyl, thiazolyl, thienyl, triazolyl, piperazinyl, piperidinyl, pyrrolidinyl, tetrahydroquinolinyl, tetrahydroisoquinolinyl, tetrahydrothienyl, and benzo-1,3-dioxolyl, wherein $R^3$ is optionally substituted with 1, 2, 3, or 4 $R^6$ substituents.

In one embodiment of the invention, $R^6$ is chosen from: halogen, (carbonyl)$_{0-1}$C$_{1-10}$ alkyl, C$_{1-10}$ alkyl (carbonyl)$_{0-1}$C$_{0-10}$ alkyl, C$_{0-10}$ alkyl(carbonyl)$_{0-1}$aryl C$_{0-10}$ alkyl, C$_{0-10}$ alkyl(carbonyl)$_{0-1}$ C$_{3-8}$ cycloalkyl C$_{0-10}$ alkyl, C$_{0-10}$ alkyl(carbonyl)$_{0-1}$(C$_{3-8}$)heterocyclyl C$_{0-10}$ alkyl, C$_{0-10}$ alkyl(carbonyl)$_{0-1}$(C$_{3-8}$ heterocycloalkyl C$_{0-10}$ alkyl, C$_{0-10}$ alkyl amino(carbonyl)$_{0-1}$ C$_{0-10}$ alkyl, C$_{3-8}$ cycloalkyl C$_{1-10}$ alkyl amino(carbonyl)$_{0-1}$C$_{0-10}$ alkyl, C$_{3-8}$ heterocyclyl C$_{0-10}$ alkyl amino(carbonyl)$_{0-1}$ C$_{0-10}$ alkyl, C$_{3-8}$ heterocycloalkyl C$_{0-10}$ alkyl amino(carbonyl)$_{0-1}$ C$_{0-10}$ alkyl, aryl C$_{0-10}$ alkyl amino(carbonyl)$_{0-1}$ C$_{0-10}$ alkyl, C$_{1-10}$ alkoxy (carbonyl)$_{0-1}$ C$_{0-10}$ alkyl, carboxyl C$_{0-10}$ alkyl, carboxyl aryl, carboxyl C$_{3-8}$ cycloalkyl, carboxyl C$_{3-8}$ heterocyclyl, carboxyl C$_{3-8}$ heterocycloalkyl, C$_{1-10}$ alkoxy, Cl$_{1-10}$alkyloxy C$_{0-10}$alkyl, hydroxy C$_{0-10}$alkyl, oxo, and cyano; wherein $R^6$ is optionally substituted with 1, 2, 3, or 4 substituents, $R^7$.

In a variant of this embodiment, $R^6$ is chosen from: halogen, (carbonyl)$_{0-1}$C$_{1-10}$ alkyl, C$_{1-10}$ alkyl(carbonyl)$_{0-1}$C$_{0-10}$ alkyl, C$_{0-10}$ alkyl(carbonyl)$_{0-1}$aryl C$_{0-10}$ alkyl, C$_{0-10}$ alkyl (carbonyl)$_{0-1}$C$_{3-8}$ cycloalkyl C$_{0-10}$ alkyl, C$_{0-10}$ alkyl(carbonyl)$_{0-1}$(C$_{3-8}$)heterocyclyl C$_{0-10}$ alkyl, C$_{0-10}$ alkyl (carbonyl)$_{0-1}$(C$_{3-8}$ heterocycloalkyl C$_{0-10}$ alkyl, C$_{0-10}$ alkyl amino(carbonyl)$_{0-1}$ C$_{0-10}$ alkyl, C$_{3-8}$ cycloalkyl C$_{0-10}$ alkyl amino(carbonyl)$_{0-1}$ C$_{0-10}$ alkyl, C$_{1-10}$ alkoxy (carbonyl)$_{0-1}$ C$_{0-10}$ alkyl, carboxyl C$_{0-10}$ alkyl, C$_{1-10}$ alkoxy, C$_{1-10}$alkyloxy C$_{0-10}$alkyl, hydroxy C$_{0-10}$alkyl, oxo, and cyano; wherein $R^6$ is optionally substituted with 1, 2, 3, or 4 substituents, $R^7$.

In one embodiment, the compounds of the invention include: 3-biphenyl-4-yl-1-(4-hydroxypyrimidin-2-yl)-8-[(3-methylpyridin-2-yl)methyl]-1,3,8-triazaspiro[4.5]decane-2,4-dione; 3-biphenyl-4-yl-8-[(3-methylpyridin-2-yl)methyl]-1-pyridin-2-yl-1,3,8-triazaspiro[4.5]decane-2,4-dione; 1-(4-hydroxypyrimidin-2-yl)-8-[(3-methylpyridin-2-yl)methyl]-3-phenyl-1,3,8-triazaspiro[4.5]decane-2,4-dione; 2-{3-biphenyl-4-yl-8-[(3-methylpyridin-2-yl)methyl]-2,4-dioxo-1,3,8-triazaspiro[4.5]dec-1-yl}isonicotinic acid; 3-biphenyl-4-yl-1-(6-hydroxypyridazin-3-yl)-8-[(3-methylpyridin-2-yl)methyl]-1,3,8-triazaspiro[4.5]decane-2,4-dione; 3-biphenyl-4-yl-1-(5-hydroxypyrimidin-2-yl)-8-[(3-methylpyridin-2-yl)methyl]-1,3,8-triazaspiro[4.5]decane-2,4-dione; 3-biphenyl-4-yl-1-(6-methoxypyridin-2-yl)-8-[(3-methylpyridin-2-yl)methyl]-1,3,8-triazaspiro[4.5]decane-2,4-dione; 1-(4-methoxypyrimidin-2-yl)-8-[(3-methylpyridin-2-yl)methyl]-3-[4-(1H-tetrazol-5-yl)phenyl]-1,3,8-triazaspiro[4.5]decane-2,4-dione; 3-biphenyl-4-yl-1-(4-hydroxypyrimidin-2-yl)-8-[(3-methylpyridin-2-yl)methyl]-1,3,8-triazaspiro[4.5]decane-2,4-dione; 3-biphenyl-4-yl-8-[(3-bromopyridin-2-yl)methyl]-1-pyrimidin-2-yl-1,3,8-triazaspiro[4.5]decane-2,4-dione; 3-biphenyl-4-yl-1-(2-hydroxypyrimidin-4-yl)-8-[(3-methylpyridin-2-yl)methyl]-1,3,8-triazaspiro[4.5]decane-2,4-dione; 4'-{1-(6-hydroxypyrimidin-4-yl)-8-[(3-methylpyridin-2-yl)methyl]-2,4-dioxo-1,3,8-triazaspiro[4.5]dec-3-yl}biphenyl-4-carboxylic acid; 3-biphenyl-4-yl-1-(5-hydroxypyrazin-2-yl)-8-[(3-methylpyridin-2-yl)methyl]-1,3,8-triazaspiro[4.5]decane-2,4-dione; 3-biphenyl-4-yl-1-(2-hydroxypyridin-4-yl)-8-[(3-methylpyridin-2-yl)methyl]-1,3,8-triazaspiro[4.5]decane-2,4-dione; 4'-{8-[(3-methylpyridin-2-yl)methyl]-2,4-dioxo-1-pyrimidin-2-yl-1,3,8-triazaspiro[4.5]dec-3-yl}biphenyl-4-carboxylic acid; 5-(4-{8-[(3-carboxypyridin-2-yl)methyl]-2,4-dioxo-1-pyrimidin-2-yl-1,3,8-triazaspiro[4.5]dec-3-yl}phenyl)pyridine-2-carboxylic acid; 4'-{8-[(3-methylpyridin-2-yl)methyl]-2,4-dioxo-1-pyrimidin-2-yl-1,3,8-triazaspiro[4.5]dec-3-yl}biphenyl-3-carboxylic acid; 3-biphenyl-4-yl-1-(4-hydroxypyrimidin-2-yl)-8-[(3-methylpyridin-2-yl)methyl]-2,4-dioxo-1,3,8-triazaspiro[4.5]decane-6-carboxylic acid; 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid; 3-biphenyl-4-yl-8-[(3-methylpyridin-2-yl)methyl]-2,4-dioxo-1-pyrimidin-2-yl-1,3,8-triazaspiro[4.5]decane-6-carboxylic acid; 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid; 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid; 4'-{1-(6-methoxypyrimidin-4-yl)-8-[(3-methylpyridin-2-yl)methyl]-2,4-dioxo-1,3,8-triazaspiro[4.5]dec-3-yl}biphenyl-4-carboxylic acid; or a pharmaceutically acceptable salt thereof, or a stereoisomer thereof, or a pharmaceutically acceptable salt of the stereoisomer thereof.

In another embodiment of the invention, compounds include: 3-biphenyl-4-yl-1-(4-hydroxypyrimidin-2-yl)-8-[(3-methylpyridin-2-yl)methyl]-1,3,8-triazaspiro[4.5]decane-2,4-dione; 1-(4-hydroxypyrimidin-2-yl)-8-[(3-methylpyridin-2-yl)methyl]-3-phenyl-3-phenyl-1,3,8-triazaspiro[4.5]decane-2,4-dione; 3-biphenyl-4-yl-1-(4-hydroxypyrimidin-2-yl)-8-[(3-methylpyridin-2-yl)methyl]-1,3,8-triazaspiro[4.5]decane-2,4-dione; 3-biphenyl-4-yl-8-[(3-bromopyridin-2-yl)methyl]-1-pyrimidin-2-yl-1,3,8-triazaspiro[4.5]decane-2,4-dione; 3-biphenyl-4-yl-1-(2-hydroxypyrimidin-4-yl)-8-[(3-methylpyridin-2-yl)methyl]-1,3,8-triazaspiro[4.5]decane-2,4-dione; 4'-{1-(6-hydroxypyrimidin-4-yl)-8-[(3-methylpyridin-2-yl)methyl]-2,4-dioxo-1,3,8-triazaspiro[4.5]dec-3-yl}biphenyl-4-carboxylic acid; 4'-{8-[(3-methylpyridin-2-yl)methyl]-2,4-dioxo-1-pyrimidin-2-yl-1,3,8-triazaspiro[4.5]dec-3-yl}biphenyl-4-carboxylic acid; 4'-{8-[(3-methylpyridin-2-yl)methyl]-2,4-dioxo-1-pyrimidin-2-yl-1,3,8-triazaspiro[4.5]dec-3-yl}biphenyl-3-carboxylic acid; and 4'-{1-(6-methoxypyrimidin-4-yl)-8-[(3-methylpyridin-2-yl)methyl]-2,4-dioxo-1,3,8-triazaspiro[4.5]dec-3-yl}biphenyl-4-carboxylic acid; or a pharmaceutically acceptable salt thereof, or a stereoisomer thereof, or a pharmaceutically acceptable salt of the stereoisomer thereof.

In another embodiment of the invention, the compounds of the invention include: 3-biphenyl-4-yl-8-[(3-methylpyridin-2-yl)methyl]-1-pyridin-2-yl-1,3,8-triazaspiro[4.5]decane-2,4-dione; 2-{3-biphenyl-4-yl-8-[(3-methylpyridin-2-yl)methyl]-2,4-dioxo-1,3,8-triazaspiro[4.5]dec-1-yl}isonicotinic acid; 3-biphenyl-4-yl-1-(6-hydroxypyridazin-3-yl)-8-[(3-methylpyridin-2-yl)methyl]-1,3,8-triazaspiro[4.5]decane-2,4-dione; 3-biphenyl-4-yl-1-(5-hydroxypyrimidin-2-yl)-8-[(3-methylpyridin-2-yl)methyl]-1,3,8-triazaspiro[4.5]decane-2,4-dione; 3-biphenyl-4-yl-1-(6-methoxypyrimidin-2-yl)-8-[(3-methylpyridin-2-yl)methyl]-1,3,8-triazaspiro[4.5]decane-2,4-dione; 1-(4-methoxypyrimidin-2-yl)-8-[(3-methylpyridin-2-yl)methyl]-3-[4-(H-tetrazol-5-yl)phenyl]-1,3,8-triazaspiro[4.5]decane-2,4-dione; biphenyl-4-yl-1-(5-hydroxypyrazin-2-yl)-8-[(3-methylpyridin-2-yl)methyl]-1,3,8-triazaspiro[4.5]decane-2,4-dione; 3-biphenyl-4-yl-1-(2-hydroxypyridin-4-yl)-8-[(3-methylpyridin-2-yl)methyl]-1,3,8-triazaspiro[4.5]decane-2,4-dione; 5-(4-{8-[(3-carboxypyridin-2-yl)methyl]-2,4-dioxo-1-pyrimidin-2-yl-1,3,8-triazaspiro[4.5]dec-3-yl}phenyl)pyridine-2-carboxylic acid; 3-biphenyl-4-yl-1-(4-hydroxypyrimidin-2-yl)-8-[(3-methylpyridin-2-yl)methyl]-2,4-dioxo-1,3,8-triazaspiro[4.5]decane-6-carboxylic acid; 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid; 3-biphenyl-4-yl-8-[(3-methylpyridin-2-yl)methyl]-2,4-dioxo-1-pyrimidin-2-yl-1,3,8-triazaspiro[4.5]decane-6-carboxylic acid; 3-biphenyl-4-yl-1-(6-hydroxypyrimidin-4-yl)-8-[(3-methylpyridin-2-yl)methylpyridin-2-yl)methyl]-2,4-dioxo-1,3,8-triazaspiro[4.5]decane-6-carboxylic acid; 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid; or a pharmaceutically acceptable salt thereof, or a stereoisomer thereof, or a pharmaceutically acceptable salt of the stereoisomer thereof.

In another embodiment of the invention, the compounds include those listed below or a pharmaceutically acceptable salt thereof, or a stereoisomer thereof, or a pharmaceutically acceptable salt of the stereoisomer thereof: 4'-{1-(6-methoxypyrimidin-4-yl)-8-[(3-methylpyridin-2-yl)methyl]-2,4-dioxo-1,3,8-triazaspiro[4.5]dec-3-yl}-2-methylbiphenyl-4-carboxylic acid; 4'-{1-(6-methoxypyrimidin-4-yl)-8-[(3-methylpyridin-2-yl)methyl]-2,4-dioxo-1,3,8-triazaspiro[4.5]dec-3-yl}-3-methylbiphenyl-4-carboxylic acid; 2-fluoro-4'-{1-(6-methoxypyrimidin-4-yl)-8-[(3-methylpyridin-2-yl)methyl]-2,4-dioxo-1,3,8-triazaspiro[4.5]dec-3-yl}biphenyl-4-carboxylic acid; 2-methyl-4'-{8-[(3-methylpyridin-2-yl)methyl]-2,4-dioxo-1-pyrazin-2-yl-1,3,8-triazaspiro[4.5]dec-3-yl}biphenyl-4-carboxylic acid; 2-methyl-4'-{1-(6-methylpyrazin-2-yl)-8-[(3-methylpyridin-2-yl)methyl]-2,4-dioxo-1,3,8-triazaspiro[4.5]dec-3-yl}biphenyl-4-carboxylic acid; 4'-{1-(6-methylpyrazin-2-yl)-8-[(3-methylpyridin-2-yl)methyl]-2,4-dioxo-1,3,8-triazaspiro[4.5]dec-3-yl}biphenyl-4-carboxylic acid; 2-methyl-4'-[8-[(3-methylpyridin-2-yl)methyl]-1-(6-methylpyrimidin-4-yl)-2,4-dioxo-1,3,8-triazaspiro[4.5]dec-3-yl]biphenyl-4-carboxylic acid; 4'-[8-[(3-methylpyridin-2-yl)methyl]-1-(6-methylpyrimidin-4-yl)-2,4-dioxo-1,3,8-triazaspiro[4.5]dec-3-yl]biphenyl-4-carboxylic acid; 2-methyl-4'-{8-[(3-methylpyridin-2-yl)methyl]-2,4-dioxo-1-[6-(trifluoromethyl)pyrimidin-4-yl]-1,3,8-triazaspiro[4.5]dec-3-yl}biphenyl-4-carboxylic acid; 1-(6-methoxypyrimidin-4-yl)-8-[(3-methylpyridin-2-yl)methyl]-3-[4'-(1H-pyrazol-5-yl) biphenyl-4-yl]-1,3,8-triazaspiro[4.5]decane-2,4-dione; 1-(6-hydroxypyrimidin-4-yl)-8-[(3-methylpyridin-2-yl)methyl]-3-[4'-(1H-pyrazol-5-yl) biphenyl-4-yl]-1,3,8-triazaspiro[4.5]decane-2,4-dione; 1-(6-methoxypyrimidin-4-yl)-8-[(3-methylpyridin-2-yl)methyl]-3-[4'-(5-oxopyrazolidin-3-yl) biphenyl-4-yl]-1,3,8-triazaspiro[4.5]decane-2,4-dione; 1-(6-hydroxypyrimidin-4-yl)-8-[(3-methylpyridin-2-yl)methyl]-3-[4'-(1 morpholin-4-yl) biphenyl-4-yl]-1,3,8-triazaspiro[4.5]decane-2,4-dione; 4-(6-{3-(4-bromophenyl)-8-[(3-methylpyridin-2-yl)methyl]-2,4-dioxo-1,3,8-triazaspiro[4.5]dec-1-yl}pyrimidin-4-yl)benzoic acid; 4'-{8-[(3-methylpyridin-2-yl)methyl]-2,4-dioxo-1-pyrimidin-4-yl-1,3,8-triazaspiro[4.5]dec-3-yl}biphenyl-4-carboxylic acid; methyl 2-methyl-4'-{8-[(3-methylpyridin-2-yl)methyl]-2,4-dioxo-1-pyrimidin-4-yl-1,3,8-triazaspiro[4.5]dec-3-yl}biphenyl-4-carboxylate; 2-methyl-4'-{8-[(3-methylpyridin-2-yl)methyl]-2,4-dioxo-1-pyrimidin-4-yl-1,3,8-triazaspiro[4.5]dec-3-yl}biphenyl-4-carboxylic acid; 2-methyl-4'-[8-[(3-methylpyridin-2-yl)methyl]-1-(2-methylpyrimidin-4-yl)-2,4-dioxo-1,3,8-triazaspiro[4.5]dec-3-yl]biphenyl-4-carboxylic acid; 2-methyl-4'-{8-[(3-methylpyridin-2-yl)methyl]-2,4-dioxo-1-pyridazin-3-yl-1,3,8-triazaspiro[4.5]dec-3-yl}biphenyl-4-carboxylic acid; 4-(5-{1-(6-methoxypyrimidin-4-yl)-8-[(3-methylpyridin-2-yl)methyl]-2,4-dioxo-1,3,8-triazaspiro[4.5]dec-3-yl}-pyridin-2-yl)benzoic acid; 4-(5-{1-(4-methoxypyrimidin-2-yl)-8-[(3-methylpyridin-2-yl)methyl]-2,4-dioxo-1,3,8-triazaspiro[4.5]dec-3-yl}-pyridin-2-yl)benzoic acid; 4-(5-{8-[(4-methoxypyridin-2-yl)methyl]-1-(6-methoxypyrimidin-4-yl)-2,4-dioxo-1,3,8-triazaspiro[4.5]dec-3-yl}-pyridin-2-yl)benzoic acid; 4-(5-{8-[(4-hydroxypyridin-2-yl)methyl]-1-(6-methoxypyrimidin-4-yl)-2,4-dioxo-1,3,8-triazaspiro[4.5]dec-3-yl}-pyridin-2-yl)benzoic acid; 4-(5-{1-(6-methoxypyrimidin-4-yl)-8-[(3-methylpyridin-2-yl)methyl]-2,4-dioxo-1,3,8-triazaspiro[4.5]dec-3-yl}-pyridin-2-yl)-3-methylbenzoic acid; 4-(5-{1-(4-methoxypyrimidin-2-yl)-8-[(3-methylpyridin-2-yl)methyl]-2,4-dioxo-1,3,8-triazaspiro[4.5]dec-3-yl}-pyridin-2-yl)-3-methylbenzoic acid; 3-methyl-4-(5-{8-[(3-methylpyridin-2-yl)methyl]-2,4-dioxo-1-(2,2,2-trifluoroethyl)-1,3,8-triazaspiro[4.5]dec-3-yl}-pyridin-2-yl)benzoic acid; and 3-fluoro-4-(5-{1-(6-methoxypyrimidine-4-yl)-8-[(3-methylpyridin-2-yl)methyl]-2,4-dioxo-1,3,8-triazaspiro[4.5]dec-3-yl}pyridin-2-yl)-3-benzoic acid.

Structural representations of compounds having substituents terminating with a methyl group may display the terminal methyl group either using the characters "CH₃", e.g. "—CH₃" or using a straight line representing the presence of the methyl group, e.g., "—", i.e.,

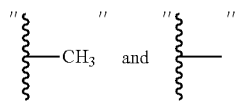

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

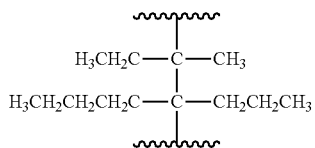

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts and solvates thereof. Unless specifically mentioned otherwise, reference to one isomer applies to any of the possible isomers. Whenever the isomeric composition is unspecified, all possible isomers are included. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —CH₂C(O)— groups (keto forms) may undergo tautomerism to form hydroxyl —CH═C(OH)— groups (enol forms). Both keto and enol forms, individually as well as mixtures thereof, are included within the scope of the present invention.

Salts

Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydro-scopicity and solubility. The term "pharmaceutically acceptable salts" refers to salts prepared from pharmaceutically acceptable non-toxic bases or acids. When the compound of the present invention is acidic, its corresponding salt can be conveniently prepared from inorganic bases or organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from organic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from inorganic or organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono, sesqui-, di- and trihydrates.

Prodrugs

The present invention includes within its scope the use of prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound which may not be a compound of formula I, but which converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

Utilities

Compounds of the present invention are inhibitors of hypoxia-inducible factor (HIF) prolyl hydroxylases, and as such are useful in the treatment and prevention of diseases and conditions in which HIF modulation is desirable, such as anemia and ischemia. Compounds of the invention can be used in a selective and controlled manner to induce hypoxia-inducible factor stabilization and to rapidly and reversibly stimulate erythropoietin production and secretion. Accordingly, another aspect of the present invention provides a method of treating or preventing a disease or condition in a mammal, the treatment or prevention of which is effected or facilitated by HIF prolyl hydroxylase inhibition, which comprises administering an amount of a compound of Formula I that is effective for inhibiting HIF prolyl hydroxylase. This aspect of the present invention further includes the use of a compound of Formula I in the manufacture of a medicament for the treatment or prevention of a disease or condition modulated by HIF prolyl hydroxylase.

In one embodiment is a method of enhancing endogenous production of erythropoietin in a mammal which comprises administering to said mammal an amount of a compound of Formula I that is effective for enhancing endogenous production of erythropoietin.

Another embodiment is a method of treating anemia in a mammal which comprises administering to said mammal a therapeutically effective amount of a compound of Formula I. "Anemia" includes, but is not limited to, chronic kidney disease anemia, chemotherapy-induced anemia (e.g., anemia resulting from antiviral drug regimens for infectious diseases, such as HIV and hepatitis C virus), anemia of chronic disease, anemia associated with cancer conditions, anemia resulting from radiation treatment for cancer, anemias of chronic immune disorders such as rheumatoid arthritis, inflammatory bowel disease, and lupus, and anemias due to menstruation or of senescence or in other individuals with iron processing deficiencies such as those who are iron-replete but unable to utilize iron properly.

Another embodiment is a method of treating ischemic diseases in a mammal, which comprises administering to said mammal a therapeutically effective amount of a compound of Formula I.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., anemia.

Pharmaceutical Composition

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or a pharmaceutically acceptable salt or solvate thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other active ingredients known to be useful for improving the level of erythropoietin in a patient.

Synthesis

Methods for preparing the compounds of this invention are illustrated in the following schemes. Other synthetic protocols will be readily apparent to those skilled in the art. The examples illustrate the preparation of the compounds of Formula I and as such are not to be considered as limiting the invention set forth in the claims appended hereto. Unless otherwise indicated, all variables are as previously defined.

Abbreviations used herein are as follows: Ac=acetyl; BOC=t-butoxycarbonyl; DCM=dichloromethane; DME=dimethylether; DMF=dimethylformamide; h=hour; LiHMDS=lithium hexamethyldisilazane; Me=methyl; and TFA=trifluoroacetic acid.

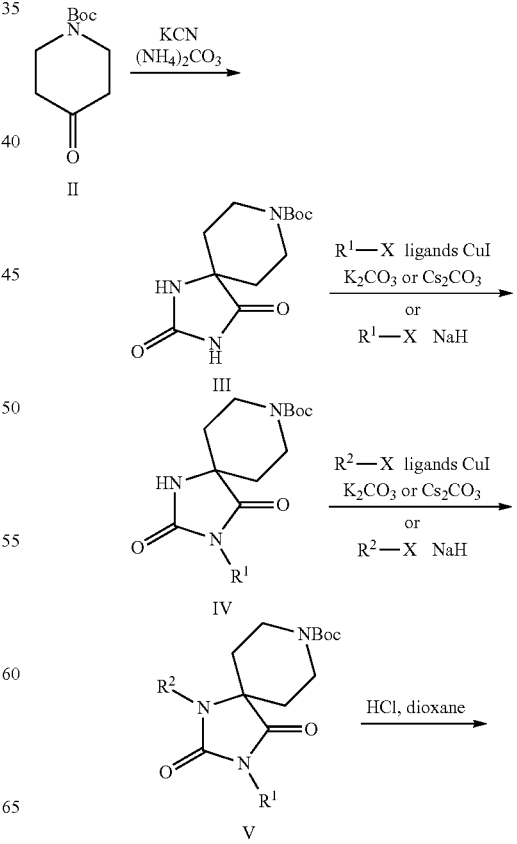

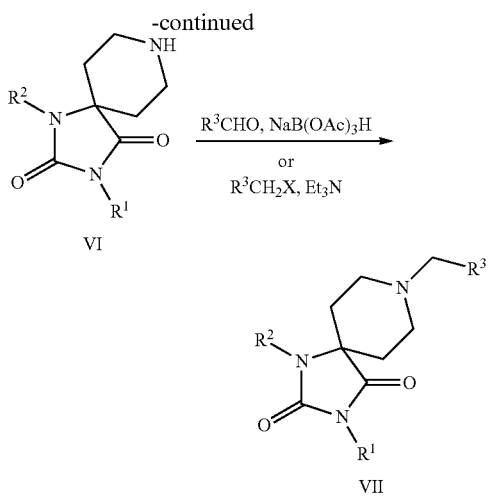

As illustrated in Scheme 1, a compound of formula II may be converted to a compound of formula III by reaction with ammonium carbonate and potassium cyanide such as is disclosed, for example, in Sarges, R.; Schnur, R. C.; Belletire, J. L.; Peterson, M. J. *J. Med. Chem.* 1988, 31, 230-43 and Courtoison, J. C.; Coudert, P.; Couquelet, J.; Tronche, P.; Jonadet, M.; Bastide, P. *Farmaco, Edizione Sci.* 1988, 43, 153-60. Reaction of a compound of formula III with a halide, $R^1$—X, where X represents a leaving group such as I, Br, Cl, OTf, is accomplished using copper(I) salts (such as copper(I) iodide, CuI), various ligands (such as N,N'-dimethylethylenediamine, 1,10-phenanthroline, 2,2,6,6-tetramethyl-3,5-heptadion) and a base (such as potassium or cesium carbonate) in a variety of solvents (such as DMF, acetonitrile, dioxane and toluene). In some cases, conversion of a compound of formula II to a compound of formula IV is accomplished using copper salts (such as copper bromide), strong base (such as sodium hydride) in various solvents (such as N,N-dimethylformamide). The latter method is better suitable for aliphatic halides, where $R^1$=alkyl, heteroalkyl, etc. Alternatively, many other conditions may accomplish the conversion of a compound of formula III to a compound of formula IV, including: stoichiometric use of copper salts and high temperature; reaction of the compound of formula III with the halide, $R^1$—X, where X is boronic acid (X=—B(OH)$_2$) or boronic acid ester; using a tertiary organic or inorganic base (such as triethylamine, N,N-diisopropylethylamine, and sodium hydride) and copper salts (such as Cu(OAc)$_2$, CuCl$_2$) in various solvents (such as methylene chloride, THF, dioxane, acetonitrile) as disclosed by Konkel, M. J., Packiarajan, M., Chen, H., Topiwala, U. P., Jimenez, H., Talisman, I. J., Coate, H., and Walker, M. W., in Bioorg. Med. Chem. Lett. 2006, 16, 3950-3954. In some cases, conversion of II to IV is accomplished using copper salts (such as copper bromide), strong base (such as sodium hydride) in various solvents (such as N,N-dimethylformamide).

Conversion of IV to V is accomplished under conditions described for the conversion of III to IV, where $R^2$—X is used in place of $R^1$—X.

Deprotection of the Boc-group in V is accomplished by a reaction with an acid such as hydrogen chloride, trifluoroacetic acid, sulfuric acid, or hydrogen bromide, either neat or in organic solvents such as methylene chloride, dioxane, or ether.

Formation of a compound of formula I is accomplished by a one-pot reductive amination of the compound of formula VI using a reducing agent (such as sodium triacetoxyborohydride) or by a stepwise procedure analogous to Scheme 1 forming an imine with corresponding carbonyl compound VI first, and subsequently reducing the imine with a reducing agent (such as sodium borohydride, hydrogenation using palladium on carbon, or zinc in acetic acid).

Alternatively, the formation of I is accomplished by a reaction of VI with $R^3CH_2X$ in which X is a halogen (or alternatives, such as a triflate, or mesylate) and a base (such as triethylamine), neat or in organic solvents (such as acetonitrile or methylene chloride).

The steps in the reaction sequence depicted in Scheme 1 may be carried out in different order, for example in the order as shown below in Scheme 2, with the reaction conditions and suitable reagents being substantially the same as those described above for Scheme 1.

Scheme 2

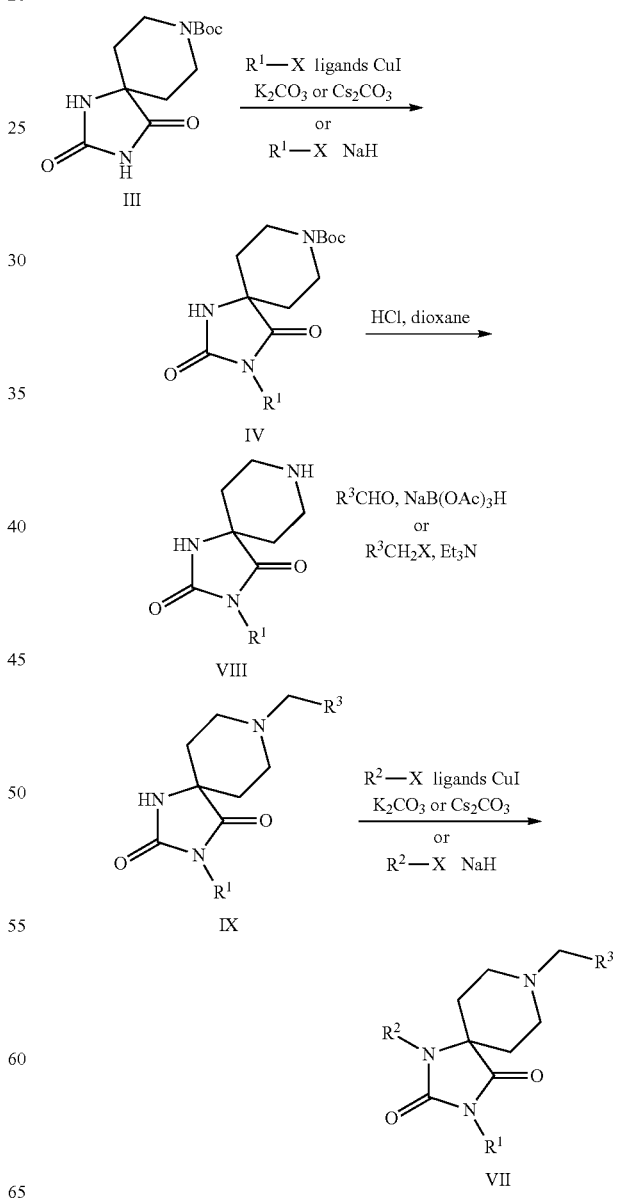

Preparation of Intermediate A (Compound A-1)

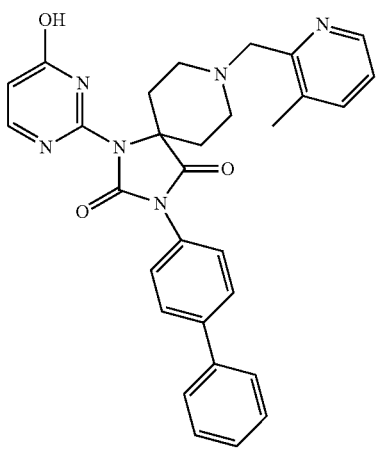

A mixture of tert-butyl 4-oxopiperidine-1-carboxylate (105 g, 527 mmol) potassium cyanide (51.5 g, 790 mmol) and ammonium carbonate (152 g, 1581 mmol) in Water (350 mL) and Ethanol (350 mL) was heated to 95° C. for 2 h, and cooled by ice-bath with slow stirring. The solids were collected by filtration, rinsed with 100 mL of water/ethanol=1:1 (volume:volume) and dried in a desiccator. LCMS (Method B): 2.21 min, m/z (MH-Boc)$^+$=170.1.

Example 1

3-biphenyl-4-yl-1-(4-hydroxyprimidin-2-yl)-8-[(3-methylpyridin-2-yl)methyl]-1,3,8-triazaspiro[4.5]decane-2,4-dione, (1-1)

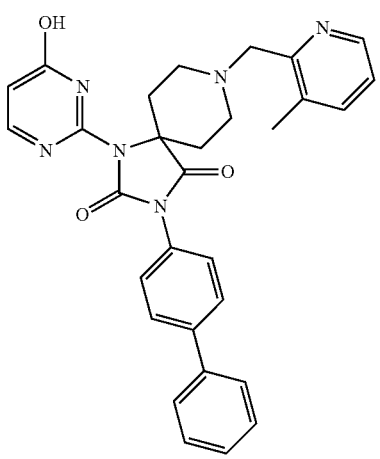

Step A (Compound 1-A)

A solution of Intermediate A (A-1)(23.77 mmol), 4-iodobiphenyl (22.58 mmol) in acetonitrile (80 ml) and DMF (80 mL) was degassed with a stream of nitrogen for 15 minutes. N,N'-dimethylethylenediamine (5.94 mmol), copper(I) iodide (5.94 mmol), and potassium carbonate (71.3 mmol) were added sequentially. The resulting mixture was heated to 85° C. for 15 h, combined with ethyl acetate (300 mL) and water (300 mL). The organic layer from this combination step was separated. The organic extract was washed with water (2×300 mL), dried over sodium sulfate and concentrated. The purification was accomplished by column chromatography on silica gel: eluted with a gradient of 0-100% hexanes in ethyl acetate. White solid, 1-A, resulted. LCMS (Method B): 3.21 min, m/z (MH-Boc)=321.0.

Step B (Compound 1-B)

A solution of the product of Step A, 1-A, (10 mmol), 2-iodo-4-methoxypyrimidine (30 mmol) in acetonitrile (20 ml) and DMF (20 mL) was degassed with a stream of nitrogen for 15 minutes. 2,2,6,6-tetramethyl-3,5-heptadion (10 mmol), copper(I) iodide (10 mmol), and cesium carbonate (50 mmol) were added sequentially and the resulting mixture was heated to 85° C. for 15 h. The heated mixture was then combined with ethyl acetate (300 mL) and water (300 mL). The organic layer separated. The organic extract was washed with water (2×300 mL), dried over sodium sulfate and concentrated. The purification was accomplished by preparative HPLC (Method C) and the product, 1-B, was isolated as a salt of trifluoroacetaic acid.

Step C (Compound 1-C)

4M HCl in dioxane (60 ml, 240 mmol) was added to the product of Step B, 1-B, (6 mmol) via syringe. The resulting mixture was stirred at ambient temperature for 1 h, concentrated to an approximate volume of 30 mL and cooled to 10° C. Solids were collected by filtration, rinsed with 10 mL of dioxane and dried in desiccator.

Step D (Compound 2-D)

The product of Step C, 1-C, (4 mmol) was added to methylene chloride (40 mL) to form a solution. 3-methylpyridine-2-carboxaldehyde (5 mmol) and sodium triacetoxyborohydride (20 mmol) were added to the solution sequentially. The resulting mixture was stirred at ambient temperature for 2 h. Methanol (20 mL) was added and the resulting mixture was stirred at ambient temperature for 5 minutes and then concentrated. The final purification was accomplished by preparative reverse phase HPLC (Method C) to give the title compound, 1-D, isolated as a salt of trifluoroacetic acid; 1HNMR (CDCl$_3$): δ=2.03-2.15 (m, 4H), 2.03 (s, 3H), 3.53-4.30 (m, 6H), 4.06 (s, 3H), 6.60-8.49 (m, 14H); LCMS (Method A), 1.71 min, m/z (MH)+=535.

Step E (Compound 2-E)

The product of Step D, 1-D, was combined with 1M aqueous solution of hydrochloric acid and the resulting mixture was refluxed in a sealed tube for 8 h. The final purification was accomplished by preparative reverse phase HPLC (Method C) to give the title compound, 1-1, EXAMPLE 1, isolated as a salt of trifluoroacetic acid; 1HNMR (CDCl$_3$): δ=1.96 (s, 3H), 2.24 (m, 2H), 2.34 (m, 2H), 3.84 (m, 2H), 3.92 (m, 2H), 4.48 (s, 2H), 6.18 (d, 1H, J=6.6 Hz), 7.24-7.87 (m, 12H), 8.43 (d, 1H, J=4.3 Hz); LCMS (Method A), 1.60 min, m/z (MH)+=521.

Table 1 discloses in addition to Example 1-1, Examples 1-2 through 1-71 of formula IX which were prepared according to the general procedure described for Example 1-1 and isolated as salts of trifluoroacetic acid using preparative HPLC (Method C) described previously.

TABLE 1

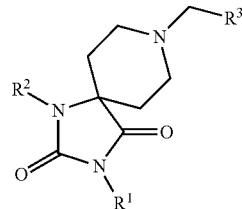

| Ex. No. | IUPAC name | R1 | R2 | R3 | NMR and LCMS |
|---|---|---|---|---|---|
| 1-1 | 3-biphenyl-4-yl-1-(4-hydroxypyrimidin-2-yl)-8-[(3-methylpyridin-2-yl)methyl]-1,3,8-triazaspiro[4.5]decane-2,4-dione | biphenyl-4-yl | 4-hydroxypyrimidin-2-yl | (3-methylpyridin-2-yl) | 1HNMR(CDCl3): δ = 1.96 (s, 3H), 2.24 (m, 2H), 2.34(m, 2H), 3.84(m, 2H), 3.92(m, 2H), 4.48(s, 2H), 6.18(d, 1H, J = 6.6 Hz), 7.24-7.87(m, 12H), 8.43 (d, 1H, J = 4.3 Hz); LCMS (Method A), 1.60 min, m/z (MH)+ = 521. |
| 1-2 | 3-biphenyl-4-yl-8-[(3-methylpyridin-2-yl)methyl]-1-pyridin-2-yl-1,3,8-triazaspiro[4.5]decane-2,4-dione | biphenyl-4-yl | pyridin-2-yl | (3-methylpyridin-2-yl) | 8.56 (d, J = 4.8, 2H), 8.52 (d, J = 4.8, 1H), 8.14 (d, J = 8.5, 1H), 7.91 (dt, J = 1.8, 7.4, 1H), 7.78 (d, J = 8.5, 2H), 7.73 (d, J = 8.1, 1H), 7.68 (d, J = 8.5, 2H), 7.61 (d, J = 8.5, 2H), 7.48 (t, J = 7.5, 2H), 7.38 (m, 2H), 7.31 (m, 1H). LCMS (Method A): 1.77 min, m/z (MH)+ = 530. |
| 1-3 | 1-(4-hydroxypyrimidin-2-yl)-8-[(3-methylpyridin-2-yl)methyl]-3-phenyl-1,3,8-triazaspiro[4.5]decane-2,4-dione | phenyl | 4-hydroxypyrimidin-2-yl | (3-methylpyridin-2-yl) | 1HNMR(CD3OD): δ = 2.40 (s, 3H), 2.40 (m, 2H), 3.44 (m, 6H), 4.72 (s, 2H), 6.22 (s, 1H), 7.38 (m, 1H), 7.53 (m, 7H), 7.60 (m, 1H); 8.54 (d, 1H, J = 3.7 Hz); LCMS (Method B), 1.89 min, m/z (MH)+ = 445.0. |
| 1-4 | 3-biphenyl-4-yl-8-[(3-methylpyridin-2-yl)methyl]-1-phenyl-1,3,8-triazaspiro[4.5]decane-2,4-dione | biphenyl-4-yl | phenyl | (3-methylpyridin-2-yl) | 1HNMR(CD3OD): 8.40 (d, J = 4.8, 1H), 7.76 (d, J = 8.5, 2H), 7.68 (d, J = 7.6, 1H), 7.65 (d, J = 8.0, 2H), 7.61 (d, J = 7.4, 3H), 7.57 (m, 2H), 7.46 (t, J = 7.8, 2H), 7.45 (d, J = 7.7, 2H), 7.37 (t, J = 7.6, 1H), 7.30 (m, 1H), 4.53 (s, 2H), 3.92 (t, J = 11.0, 2H), 3.68 (d, J = 12.6, 2H), 2.56 (d, J = 14.6, 2H), 2.41 (dt, J = 4.2, 14.2, 2H), 2.29 (s, 3H). LCMS (Method A): 1.65 min, m/z (MH)+ = 503.0. |
| 1-5 | 2-{3-biphenyl-4-yl-8-[(3-methylpyridin-2-yl)methyl]-2,4-dioxo-1,3,8-triazaspiro[4.5]dec-1-yl}isonicotinic acid | biphenyl-4-yl | CO2H-pyridinyl | (3-methylpyridin-2-yl) | 1HNMR(CD3OD): 8.74 (s, 1H), 8.70 (d, J = 5.1, 1H), 8.52 (d, J = 4.4, 1H), 7.79 (d, J = 8.5, 3H), 7.73 (d, J = 7.8, 1H), 7.67 (d, J = 7.6, 2H), 7.62 (d, J = 8.4, 2H), 7.47 (t, J = 8.8, 2H), 7.37 (m, 2H), 4.72 (s, 2H), 4.05 (t, J = 13.3, 2H), 3.69 (m, 2H), 2.43 (d, J = 14.6, 2H), 2.40 (s, 3H). LCMS (Method A): 1.67 min, m/z (MH)+ = 548.0. |

TABLE 1-continued

IX

| Ex. No. | IUPAC name | R1 | R2 | R3 | NMR and LCMS |
|---|---|---|---|---|---|
| 1-6 | 3-biphenyl-4-yl-1-(6-fluoropyridin-2-yl)-8-[(3-methylpyridin-2-yl)methyl]-1,3,8-triazaspiro[4.5]decane-2,4-dione | biphenyl-4-yl | 6-fluoropyridin-2-yl | (3-methylpyridin-2-yl)methyl | 1HNMR(CD3OD): 8.53 (d, J = 4.6, 1H), 8.14 (d, J = 7.8, 1H), 8.05 (q, J = 8.0, 1H), 7.98 (d, J = 6.6, 2H), 7.74 (d, J = 7.6, 1H), 7.67 (d, J = 8.5, 2H), 7.47 (t, J = 7.8, 2H), 7.37 (m, 2H), 6.96 (dd, J = 2.5, 8.0, 1H), 4.77 (s, 2H), 4.10 (dt, J = 3.2, 13.5, 2H), 3.70 (m, 4H), 2.43 (d, J = 14.6, 2H), 2.41 (s, 3H). LCMS (Method A): 1.77 min, m/z (MH)+ = 521.9. |
| 1-7 | 6-{3-biphenyl-4-yl-8-[(3-methylpyridin-2-yl)methyl]-2,4-dioxo-1,3,8-triazaspiro[4.5]dec-1-yl}nicotinonitrile | biphenyl-4-yl | 5-cyanopyridin-2-yl | (3-methylpyridin-2-yl)methyl | 1HNMR(CD3OD): 8.73 (d, J = 5.0, 1H), 8.58 (s, 1H), 8.53 (d, J = 5.1, 1H), 7.79 (d, J = 8.5, 2H), 7.74 (d, J = 7.5, 1H), 7.68 (d, J = 7.1, 2H), 7.57 (dd, J = 1.2, 5.3, 1H), 7.48 (t, J = 7.4, 2H), 7.37 (m, 2H), 4.73 (s, 2H), 4.06 (t, J = 13.7, 2H), 3.74 (m, 4H), 2.43 (d, J = 16.0, 2H), 2.40 (s, 3H). LCMS (Method A): 1.76 min, m/z (MH)+ = 528.9. |
| 1-8 | 3-biphenyl-4-yl-8-[(3-methylpyridin-2-yl)methyl]-1-pyridin-4-yl-1,3,8-triazaspiro[4.5]decane-2,4-dione | biphenyl-4-yl | pyridin-4-yl | (3-methylpyridin-2-yl)methyl | 1HNMR(CD3OD): 8.82 (d, J = 6.6, 1H0, 8.48 (d, J = 3.9, 1H), 8.24 (d, J = 7.1, 1H), 7.80 (d, J = 6.6, 2H), 7.75 (d, J = 7.8, 1H), 7.68 (d, J = 8.0, 2H), 7.63 (d, J = 8.7, 2H), 7.48 (t, J = 7.3, 2H), 7.38 (m, 2H), 4.63 (s, 2H), 4.00 (dt, J = 2.9, 13.0, 2H), 3.82 (d, J = 12.1, 2H), 2.93 (dt, J = 4.8, 15.1, 2H), 2.61 (d, J = 15.4, 2H), 2.37 (s, 3H). LCMS (Method A): 1.43 min, m/z (MH)+ = 503.9. |
| 1-9 | 3-biphenyl-4-yl-1-(6-hydroxypyridazin-3-yl)-8-[(3-methylpyridin-2-yl)methyl]-1,3,8-triazaspiro[4.5]decane-2,4-dione | biphenyl-4-yl | 6-hydroxypyridazin-3-yl | (3-methylpyridin-2-yl)methyl | 1HNMR(CD3OD): 8.46 (d, J = 3.1, 1H), 7.91 (d, J = 9.8, 1H), 7.66 (d, J = 8.5, 2H), 7.71 (d, J = 7.7, 1H), 7.64 (d, J = 7.3, 2H), 7.59 (d, J = 8.5, 2H), 7.45 (t, J = 8.0, 2H), 7.35 (m, 2H), 7.08 (d, J = 10.0, 1H), 4.61 (s, 2H), 3.94 (dt, J = 2.5, 13.0, 2H), 3.73 (d, J = 12.6, 2H), 3.02 (dt, J = 4.6, 14.6, 2H), 2.48 (d, J = 15.1, 2H), 2.34 (s, 3H). LCMS (Method A): 1.70 min, m/z (MH)+ = 520.9. |

US 8,921,555 B2

TABLE 1-continued

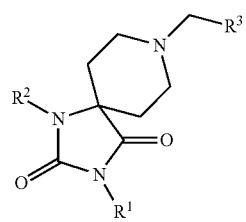

IX

| Ex. No. | IUPAC name | R1 | R2 | R3 | NMR and LCMS |
|---|---|---|---|---|---|
| 1-10 | 3-biphenyl-4-yl-1-(5-hydroxypyrimidin-2-yl)-8-[(3-methylpyridin-2-yl)methyl]-1,3,8-triazaspiro[4.5]decane-2,4-dione | biphenyl-4-yl | 5-hydroxypyrimidin-2-yl (OH on pyrimidine) | (3-methylpyridin-2-yl)methyl | 1HNMR(CD3OD): 8.56 (d, J = 2.4, 1H), 8.44 (s, 1H), 7.86 (d, J = 7.6, 1H), 7.77 (d, J = 8.4, 2H), 7.66 (d, J = 8.4, 2H), 7.60 (d, J = 8.5, 2H), 7.60 (d, J = 8.5, 2H), 7.48 (m, 4H), 7.37 (t, J = 7.6, 1H), 4.71 (s, 2H), 4.00 (dt, J = 2.3, 13.5, 2H), 3.76 (d, J = 12.1, 2H), 3.22 (dt, J = 4.4, 14.7, 2H), 2.48 (d, J = 9.6, 2H), 2.43 (s, 3H). LCMS (Method A): 1723 min, m/z (MH)+ = 520.9. |
| 1-11 | 3-biphenyl-4-yl-1-(6-methoxypyridin-2-yl)-8-[(3-methylpyridin-2-yl)methyl]-1,3,8-triazaspiro[4.5]decane-2,4-dione | biphenyl-4-yl | 6-methoxypyridin-2-yl (MeO) | (3-methylpyridin-2-yl)methyl | 1HNMR(CD3OD): 8.42 (d, J = 4.6, 1H), 7.73 (m, 4H), 7.62 (d, J = 8.3, 2H), 7.57 (d, J = 8.5, 2H), 7.45 (q, J = 7.7, 3H), 7.35 (m, 2H), 6.76 (d, J = 8.0, 1H), 4.59 (s, 2H), 4.04 (s, 3H), 3.97 (t, J = 11.0, 2H), 3.67 (d, J = 12.2, 2H), 3.36 (t, J = 14.4, 2H), 2.43 (d, J = 14.7, 2H), 2.32 (s, 3H). LCMS (Method A): 1.78 min, m/z (MH)+ = 534.0 |
| 1-12 | 3-biphenyl-4-yl-1-(6-hydroxypyridin-2-yl)-8-[(3-methylpyridin-2-yl)methyl]-1,3,8-triazaspiro[4.5]decane-2,4-dione | biphenyl-4-yl | 6-hydroxypyridin-2-yl (HO) | (3-methylpyridin-2-yl)methyl | 1HNMR(CD3OD): 8.50 (d, J = 4.6, 1H), 7.76 (d, J = 7.3, 2H), 7.72 (t, J = 6.1, 2H), 7.66 (d, J = 7.3, 2H), 7.58 (d, J = 7.3, 2H), 7.50 (d, J = 7.8, 2H), 7.46 (t, J = 7.3, 2H), 7.37 (m, 2H), 6.61 (d, J = 8.2, 1H). 4.71 (s, 2H), 4.01 (t, J = 12.8, 2H), 3.75 (d, J = 12.4, 2H), 3.56 (t, J = 11.4, 2H), 2.39 (d, J = 10.7, 2H), 2.38 (s, 3H). LCMS (Method A): 1.65 min, m/z (MH)+ = 520.0. |
| 1-13 | methyl 6-{3-biphenyl-4-yl-8-[(3-methylpyridin-2-yl)methyl]-2,4-dioxo-1,3,8-triazaspiro[4.5]dec-1-yl}pyridine-2-carboxylate | biphenyl-4-yl | 6-(methoxycarbonyl)pyridin-2-yl (CO2Me) | (3-methylpyridin-2-yl)methyl | 1HNMR(CD3OD): 8.51 (d, J = 4.6, 1H), 8.43 (d, J = 8.2, 1H), 8.04 (t, J = 7.8, 1H), 7.97 (d, J = 7.6, 1H), 7.75 (d, J = 8.3, 2H), 7.64 (d, J = 7.8, 2H), 7.59 (d, J = 8.5, 2H), 7.45 (t, J = 7.5, 2H), 7.36 (m, 2H), 4.84 (s, 2H), 4.12 (t, J = 12.6, 2H), 4.02 (s, 3H), 3.77 (t, J = 11.0, 4H), 2.43 (s, 3H), 2.41 (d, J = 15.4, 2H). LCMS (Method A): 2.56 min, m/z (MH)+ = 562.0. |

TABLE 1-continued

IX

| Ex. No. | IUPAC name | R1 | R2 | R3 | NMR and LCMS |
|---|---|---|---|---|---|
| 1-14 | 6-{3-biphenyl-4-yl-8-[(3-methylpyridin-2-yl)methyl]-2,4-dioxo-1,3,8-triazaspiro[4.5]dec-1-yl}pyridine-2-carboxylic acid | biphenyl-4-yl | pyridin-2-yl with CO₂H at 6-position | (3-methylpyridin-2-yl)methyl | 1HNMR(CD3OD): 8.51 (d, J = 4.5, 1H), 8.42 (d, J = 8.2, 1H), 8.06 (t, J = 7.8, 1H), 8.03 (t, J = 6.7, 1H), 7.78 (d, J = 6.5, 2H), 7.73 (d, J = 7.8, 1H), 7.67 (d, J = 7.1, 2H), 7.61 (d, J = 8.5, 2H), 7.47 (t, J = 7.7, 2H), 7.37 (m, 2H), 4.85 (s, 2H), 4.13 (t, J = 11.7, 2H), 3.80 (m, 4H), 2.44 (d, J = 8.8, 2H), 2.42 (s, 3H). LCMS (Method A): 2.00 min, m/z (MH)+ = 547.9. |
| 1-15 | 1-(4-methoxypyrimidin-2-yl)-8-[(3-methylpyridin-2-yl)methyl]-3-[4-(1H-tetrazol-5-yl)phenyl]-1,3,8-triazaspiro[4.5]decane-2,4-dione | 4-(1H-tetrazol-5-yl)phenyl | 4-methoxypyrimidin-2-yl | (3-methylpyridin-2-yl)methyl | 1HNMR(CD3OD): 8.50 (m, 2H), 8.20 (d, J = 8.5, 2H), 7.79 (d, J = 8.7, 2H), 7.73 (d, J = 7.5, 1H), 7.36 (m, 1H), 6.81 (d, J = 5.7, 1H), 4.70 (s, 2H), 4.09 (s, 3H), 4.04 (t, J = 13.2, 2H), 3.77 (d, J = 12.2, 2H), 3.56 (t, J = 14.2, 2H), 2.49 (d, J = 14.6, 2H), 2.38 (s, 3H). LCMS (Method A): 1.30 min, m/z (MH)+ = 526.9. |
| 1-16 | 1-(4-hydroxypyrimidin-2-yl)-8-[(3-methylpyridin-2-yl)methyl]-3-[4-(1H-tetrazol-5-yl)phenyl]-1,3,8-triazaspiro[4.5]decane-2,4-dione | 4-(1H-tetrazol-5-yl)phenyl | 4-hydroxypyrimidin-2-yl | (3-methylpyridin-2-yl)methyl | 1HNMR(CD3OD): 8.52 (d, J = 4.1, 1H), 8.19 (d, J = 8.7, 2H), 7.89 (d, J = 7.1, 1H), 7.76 (d, J = 8.7, 2H), 7.72 (d, J = 7.6, 1H), 7.35 (dd, J = 5.1, 7.8, 1H), 6.23 (d, J = 7.1, 1H), 4.73 (s, 2H), 3.91 (dt, J = 3.0, 10.8, 2H), 3.85 (m, 4H), 2.45 (d, J = 13.9, 2H), 2.40 (s, 3H). LCMS (Method A): 1.16 min, m/z (MH)+ = 512.9. |
| 1-17 | 4-{1-(4-hydroxypyrimidin-2-yl)-8-[(3-methylpyridin-2-yl)methyl]-2,4-dioxo-1,3,8-triazaspiro[4.5]dec-3-yl}benzoic acid | 4-carboxyphenyl | 4-hydroxypyrimidin-2-yl | (3-methylpyridin-2-yl)methyl | 1HNMR(CD3OD): 8.53 (d, J = 4.4, 1H), 8.18 (d, J = 8.4, 2H), 7.87 (d, J = 5.3, 1H), 7.73 (d, J = 7.6, 1H), 7.66 (d, J = 8.7, 2H), 7.36 (dd, J = 4.8, 7.5, 1H), 6.23 (d, J = 7.1, 1H), 4.72 (s, 2H), 3.87 (m, 6H), 2.41 (d, J = 7.4, 2H), 2.40 (s, 3H). LCMS (Method A): 1.11 min, m/z (MH)+ = 488.8. |
| 1-18 | 3-biphenyl-4-yl-8-[(3-methylpyridin-2-yl)methyl]-1-pyridin-3-yl-1,3,8-triazaspiro[4.5]decane-2,4-dione | biphenyl-4-yl | pyridin-3-yl | (3-methylpyridin-2-yl)methyl | 1HNMR(CD3OD): 8.73 (d, J = 18.5, 2H), 8.38 (d, J = 3.7, 1H), 8.02 (d, J = 7.5, 1H), 7.76 (d, J = 7.0, 2H), 7.69 (t, J = 7.6, 2H), 7.62 (m, 3H), 7.45 (t, J = 7.4, 2H), 7.36 (t, J = 7.1, 1H), 7.30 (t, J = 6.7, 1H), 4.52 (s, 2H), 3.89 (t, J = 11.9, 2H), 3.67 (d, J = 10.7, 2H), 2.58 (d, J = 14.0, 2H), 2.36 (t, J = 11.7, 2H), 2.29 (s, 3H). LCMS (Method A): 1.68 min, m/z (MH)+ = 504.0. |

TABLE 1-continued

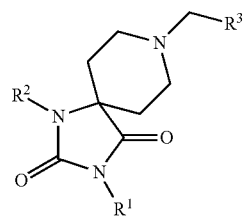

IX

| Ex. No. | IUPAC name | R1 | R2 | R3 | NMR and LCMS |
|---|---|---|---|---|---|
| 1-19 | tert-butyl (2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)acetate | biphenyl | 4-methoxypyrimidin-2-yl | tert-butyl imidazolyl acetate | LCMS (Method B), 3.11 min, m/z (MH)+ = 624.2. |
| 1-20 | tert-butyl (2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)acetate | biphenyl | 4-methoxypyrimidin-2-yl | tert-butyl imidazolyl propanoate | LCMS (Method B), 3.13 min, m/z (MH)+ = 638.2. |
| 1-21 | (2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)acetic acid | biphenyl | 4-methoxypyrimidin-2-yl | imidazolyl acetic acid | 1HNMR(CD3OD): δ = 2.10 (m, 2H), 2.91 (m, 2H), 3.18 (m, 4H), 4.07 (s, 3H), 4.08 (s, 2H), 5.22 (s, 2H), 6.77 (d, 1H, J = 2.6 Hz), 7.56 (m, 7H), 7.68 (d, 2H, J = 5.6 Hz); 7.77 (d, 2H, J = 5.6 Hz); 8.47 (d, 1H, J = 2.6 Hz); LCMS (Method B), 2.61 min, m/z (MH)+ = 568.1. |
| 1-22 | 3-(2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)propanoic acid | biphenyl | 4-methoxypyrimidin-2-yl | imidazolyl propanoic acid | 1HNMR(CD3OD): δ = 2.11 (m, 2H), 2.93 (m, 2H), 3.04 (m, 2H), 3.31 (m, 4H), 4.04 (s, 3H), 4.12 (s, 2H), 4.54 (t, 2H, J = 2.8 Hz), 6.76 (d, 1H, J = 2.6 Hz), 7.38 (t, 1H, J = 2.8 Hz), 7.47 (m, 3H), 7.56 (d, 2H, J = 4.6 Hz), 7.68 (m, 3H), 7.77 (m, 2H), 8.46 (d, 1H, J = 2.6 Hz); LCMS (Method B), 2.69 min, m/z (MH)+ = 582.1. |

TABLE 1-continued

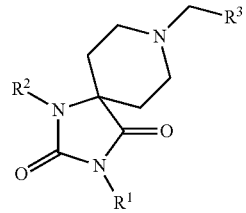

IX

| Ex. No. | IUPAC name | R1 | R2 | R3 | NMR and LCMS |
|---|---|---|---|---|---|
| 1-23 | (2-{[3-biphenyl-4-yl-1-(4-hydroxypyrimidin-2-yl)-2,4-dioxo-1,3,8-triazaspiro[4.5]dec-8-yl]methyl}-1H-imidazol-1-yl)acetic acid | 3-biphenyl-4-yl | 4-hydroxypyrimidin-2-yl (methyl) | 1-(carboxymethyl)-1H-imidazol-2-yl | 1HNMR(CD3OD): δ = 1.93 (m, 2H), 2.96 (m, 2H), 3.08 (m, 2H), 3.53 (m, 2H), 3.96 (s, 2H), 5.07 (s, 3H), 6.22 (d, 1H, J = 2.6 Hz), 7.56 (m, 7H), 7.68 (d, 2H, J = 5.6 Hz); 7.77 (d, 2H, J = 5.6 Hz); 7.83 (d, 1H, J = 2.6 Hz); LCMS (Method B), 2.61 min, m/z (MH)+ = 554.0. |
| 1-24 | 3-(2-{[3-biphenyl-4-yl-1-(4-hydroxypyrimidin-2-yl)-2,4-dioxo-1,3,8-triazaspiro[4.5]dec-8-yl]methyl}-1H-imidazol-1-yl)propanoic acid | 3-biphenyl-4-yl | 4-hydroxypyrimidin-2-yl (methyl) | 1-(2-carboxyethyl)-1H-imidazol-2-yl | LCMS (Method B), 2.51 min, m/z (MH)+ = 568.0. |
| 1-25 | 4-{1-(4-methoxypyrimidin-2-yl)-8-[(3-methylpyridin-2-yl)methyl]-2,4-dioxo-1,3,8-triazaspiro[4.5]dec-3-yl}benzonitrile | 4-cyanophenyl | 4-methoxypyrimidin-2-yl (methyl) | 3-methylpyridin-2-yl | 1HNMR(CD3OD): 8.50 (m, 2H), 7.91 (d, J = 8.7, 2H), 7.79 (d, J = 8.7, 2H), 7.73 (d, J = 7.6, 1H), 7.36 (dd, J = 4.8, 7.8, 1H), 6.80 (d, J = 6.0, 1H), 4.69 (s, 2H), 4.08 (s, 3H), 4.02 (dt, J = 2.9, 13.5, 2H), 3.75 (d, J = 10.7, 2H), 3.53 (dt, J = 4.6, 14.7, 2H), 2.48 (d, J = 15.1, 2H), 2.38 (s, 3H). LCMS (Method A): 1.44 min, m/z (MH)+ = 484.0. |
| 1-26 | ethyl 4-{1-(4-methoxypyrimidin-2-yl)-8-[(3-methylpyridin-2-yl)methyl]-2,4-dioxo-1,3,8-triazaspiro[4.5]dec-3-yl}benzoate | 4-(CO2Et)phenyl | 4-methoxypyrimidin-2-yl (methyl) | 3-methylpyridin-2-yl | 1HNMR(CD3OD): 8.50 (d, J = 6.8, 2H), 8.16 (d, J = 8.7, 2H), 7.33 (d, J = 7.8, 1H), 7.68 (d, J = 8.7, 2H), 7.36 (dd, J = 4.8, 7.5, 1H), 8.79 (d, J = 6.0, 1H), 4.68 (s, 2H), 4.40 (q, J = 7.1, 2H), 4.08 (s, 3H), 3.75 (dd, J = 1.8, 10.5, 2H), 3.53 (dt, J = 4.6, 10.0, 2H), 2.47 (d, J = 5.4, 2H), 2.38 (s, 3H), 1.41 (t, J = 7.1, 3H). LCMS (Method A): 1.53 min, m/z (MH)+ = 531.0. |
| 1-27 | 3-biphenyl-4-yl-8-[(3-methylpyridin-2-yl)methyl]-1-(2-thienyl)-1,3,8-triazaspiro[4.5]decane-2,4-dione | 3-biphenyl-4-yl | 2-thienyl | 3-methylpyridin-2-yl | 1HNMR(CD3OD): 8.40 (d, J = 4.8, 1H), 7.74 (d, J = 8.5, 2H), 7.67 (d, J = 8.6, 1H), 7.62 (d, J = 8.5, 2H), 7.57 (m, 3H), 7.44 (t, J = 7.6, 2H), 7.34 (m, 1H), 7.30 (m, 1H), 7.16 (m, 2H), 4.50 (s, 2H), 3.84 (dt, J = 3.4, 12.6, 2H), 3.67 (m, 2H), 2.52 (m, 4H), 2.28 (s, 3H). LCMS (Method A): 1.79 min, m/z (MH)+ = 509.0. |

TABLE 1-continued

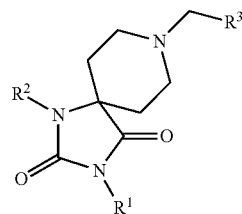

| Ex. No. | IUPAC name | R1 | R2 | R3 | NMR and LCMS |
|---|---|---|---|---|---|
| 1-28 | 3-biphenyl-4-yl-8-[(3-bromopyridin-2-yl)methyl]-1-(4-methoxypyrimidin-2-yl)-1,3,8-triazaspiro[4.5]decane-2,4-dione | biphenyl-4-yl | 4-methoxypyrimidin-2-yl | 3-bromopyridin-2-yl | 1HNMR(CDCl3): δ = 1.93 (m, 2H), 2.99(m, 2H), 3.17-3.22 (m, 4H), 3.93(s, 2H), 4.03(s, 3H), 6.59(d, 1H, J = 6.3 Hz), 7.08-7.88(m, 11H), 8.44 (d, 1H, J = 4.0 Hz); LCMS (Method A), 1.80 min, m/z (MH)+ = 401. |
| 1-29 | 3-biphenyl-4-yl-1-(4-methoxypyrimidin-2-yl)-8-[(3-methylpyridin-2-yl)methyl]-1,3,8-triazaspiro[4.5]decane-2,4-dione | biphenyl-4-yl | 4-methoxypyrimidin-2-yl | 3-methylpyridin-2-yl | 1HNMR(CDCl$_3$): δ = 2.03-2.15 (m, 4H), 2.03 (s, 3H), 3.53-4.30(m, 6H), 4.06 (s, 3H), 6.60-8.49(m, 14H); LCMS (Method A), 1.71 min, m/z (MH)+ = 535. |
| 1-30 | 1-(4-methoxypyrimidin-2-yl)-8-[(3-methylpyridin-2-yl)methyl]-3-phenyl-1,3,8-triazaspiro[4.5]decane-2,4-dione | phenyl | 4-methoxypyrimidin-2-yl | 3-methylpyridin-2-yl | 1HNMR(CD3OD): δ = 2.38 (s, 3H), 2.48 (m, 2H), 3.54 (m, 2H), 3.73 (m, 2H), 4.02 (s, 2H), 4.09 (s, 3H), 4.69 (s, 2H), 6.80 (d, 1H, J = 4.6 Hz), 7.35 (m, 1H), 7.53 (m, 6H), 7.74 (dd, 1H, J = 8.3, 1.2 Hz); 8.51 (d, 1H, J = 4.3 Hz); LCMS (Method B), 2.19 min, m/z (MH)+ = 458.9. |
| 1-31 | 3-biphenyl-4-yl-8-[(3-bromopyridin-2-yl)methyl]-1-(4-hydroxypyrimidin-2-yl)-1,3,8-triazaspiro[4.5]decane-2,4-dione | biphenyl-4-yl | 4-hydroxypyrimidin-2-yl | 3-bromopyridin-2-yl | 1HNMR(CD3OD): δ = 2.48 (m, 2H), 3.80-4.06 (m, 6H), 5.40(m, 2H), 6.46(m, 1H), 7.38-8.17(m, 12H), 8.69 (d, 1H, J = 4.7 Hz), 8.53(m, 1H); LCMS (Method A), 1.10 min, m/z (MH)+ = 587. |

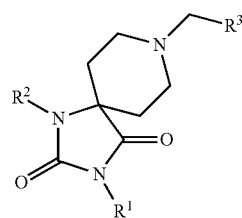

| Ex. No. | IUPAC name | R1 | R2 | R3 | NMR and LCMS |
|---|---|---|---|---|---|
| 1-32 | 4-[8-[(3-bromopyridin-2-yl)methyl]-1-(4-hydroxypyrimidin-2-yl)-2,4-dioxo-1,3,8-triazaspiro[4.5]dec-3-yl]-N-phenylbenzamide | 4-(phenylcarbamoyl)phenyl | 4-hydroxypyrimidin-2-yl | 3-methylpyridin-2-yl | 1HNMR(CD3OD): 8.54 (d, J = 4.6, 1H), 8.10 (d, J = 8.4, 2H), 7.87 (s, 1H), 7.74 (d, J = 7.8, 1H), 7.71 (m, 4H), 7.37 (t, J = 7.8, 3H), 7.16 (t, J = 7.4, 1H), 6.23 (d, J = 6.9, 1H), 4.73 (s, 2H), 3.89 (m, 6H), 2.42 (d, J = 12.1, 2H), 2.40 (s, 3H). LCMS (Method A): 1.51 min, m/z (MH)+ = 564. |
| 1-33 | 3-biphenyl-4-yl-1-(4-hydroxypyrimidin-2-yl)-8-[(3-methylpyridin-2-yl)methyl]-1,3,8-triazaspiro[4.5]decane-2,4-dione | biphenyl-4-yl | 4-hydroxypyrimidin-6-yl | 3-methylpyridin-2-yl | 1HNMR(CD3OD): 8.52 (d, J = 4.8, 1H), 8.26 (s, 1H), 7.78 (d, J = 8.5, 2H), 7.74 (d, J = 7.3, 1H), 7.67 (d, J = 7.1, 2H), 7.58 (d, J = 8.5, 2H), 7.48 (t, J = 7.6, 2H), 7.37 (m, 3H), 4.71 (s, 2H), 4.04 (t, J = 11.4, 2H), 3.74 (t, J = 11.7, 4H), 2.43 (d, J = 15.5, 2H), 2.40 (s, 3H). LCMS (Method A): 1.71 min, m/z (MH)+ = 564.0. |
| 1-34 | 4-[8-[(3-bromopyridin-2-yl)methyl]-1-(4-hydroxypyrimidin-2-yl)-2,4-dioxo-1,3,8-triazaspiro[4.5]dec-3-yl]-N-cyclopropylbenzamide | 4-(cyclopropylcarbamoyl)phenyl | 4-hydroxypyrimidin-2-yl | 3-methylpyridin-2-yl | 1HNMR(CD3OD): 8.54 (d, J = 4.4, 1H), 7.97 (d, J = 8.1, 2H), 7.87 (s, 1H), 7.74 (d, J = 7.3, 1H), 7.64 (d, J = 8.0, 2H), 7.37 (t, J = 5.7, 1H), 6.24 (d, J = 6.2, 1H), 4.73 (s, 2H), 3.88 (m, 6H), 2.89 (m, 1H), 2.42 (d, J = 12.1, 2H), 2.40 (s, 3H), 0.83 (d, J = 6.9. 2H), 0.67 (s, 2H). LCMS (Method A): 1.23 min, m/z (MH)+ = 527.9. |
| 1-35 | 3-biphenyl-4-yl-8-[(3-bromopyridin-2-yl)methyl]-1-pyrimidin-2-yl-1,3,8-triazaspiro[4.5]decane-2,4-dione | biphenyl-4-yl | pyrimidin-2-yl | 3-methylpyridin-2-yl | 1HNMR(CD3OD): 8.84 (d, J = 4.8, 2H), 8.51 (d, J = 4.6, 1H), 7.78 (d, J = 8.5, 2H), 7.72 (d, J = 7.7, 1H), 7.67 (d, J = 8.5, 2H), 7.60 (d, J = 7.5, 2H), 7.47 (t, J = 8.0, 2H), 7.38 (m, 3H), 4.69 (s, 2H), 4.04 (dt, J = 3.0, 13.3, 2H), 3.75 (d, J = 11.4, 2H0, 3.58 (dt, J = 4.6, 14.7, 2H), 2.45 (d, J = 15.1, 2H), 2.38 (s, 3H). LCMS (Method A): 1.70 min, m/z (MH)+ = 505.0. |

TABLE 1-continued

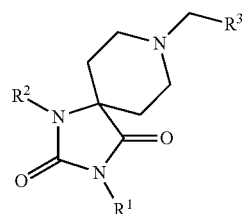

| Ex. No. | IUPAC name | R1 | R2 | R3 | NMR and LCMS |
|---|---|---|---|---|---|
| 1-36 | 3-biphenyl-4-yl-8-[(3-bromopyridin-2-yl)methyl]-1-(4-hydroxypyridin-2-yl)-1,3,8-triazaspiro[4.5]decane-2,4-dione | biphenyl-4-yl | 4-hydroxypyridin-2-yl | 3-bromopyridin-2-yl | 1HNMR(CD3OD): 8.50 (d, J = 4.1, 1H), 8.25 (d, J = 5.7, 1H), 7.77 (d, J = 8.5, 2H), 7.72 (d, J = 7.5, 1H), 7.66 (d, J = 7.3, 2H), 7.58 (d, J = 8.5, 2H), 7.54 (s, 1H), 7.46 (t, J = 7.6, 2H), 7.38 (t, J = 7.4, 1H), 7.35 (dd, J = 4.8, 7.8, 1H), 6.74 (dd, J = 2.0, 5.7, 1H), 4.70 (s, 2H), 4.01 (dt, J = 3.0, 13.5, 2H), 3.71 (d, J = 11.1, 2H), 3.61 (dt, J = 4.3, 14.4, 2H0, 2.48 (d, J = 14.7, 2H), 2.39 (s, 3H). LCMS (Method A): 1.74 min, m/z (MH)+ = 520.0. |
| 1-37 | tert-butyl 2-{[3-biphenyl-4-yl-1-(4-methoxypyrimidin-2-yl)-2,4-dioxo-1,3,8-triazaspiro[4.5]dec-8-yl]methyl}nicotinate | biphenyl-4-yl | 4-methoxypyrimidin-2-yl | tert-butyl nicotinate-2-yl | 1HNM$^R$(CDCl3): δ = 1.46 (s, 9H), 2.14(m, 2H), 3.38-4.08 (m, 10H), 4.14(s, 3H), 6.67(d, 1H, J = 5.2 Hz), 7.04-8.63(m, 13H); LCMS (Method A), 2.10 min, m/z (MH)$^+$ = 635. |
| 1-38 | 2-{[3-biphenyl-4-yl-1-(4-hydroxypyrimidin-2-yl)-2,4-dioxo-1,3,8-triazaspiro[4.5]dec-8-yl]methyl}nicotinic acid | biphenyl-4-yl | 4-hydroxypyrimidin-2-yl | nicotinic acid-2-yl | 1HNMR(CD3OD): δ = 2.40 (m, 2H), 3.34(s, 2H), 3.75-3.97 (m, 6H), 4.77(s, 2H), 6.3(d, 1H, J = 7.1 Hz), 7.37-7.82(m, 12H), 8.63 (m, 1H); LCMS (Method A), 1.63 min, m/z (MH)$^+$ = 565. |
| 1-39 | 3-biphenyl-4-yl-1-(4-methoxypyrimidin-2-yl)-8-(1H-tetrazol-5-ylmethyl)-1,3,8-triazaspiro[4.5]decane-2,4-dione | biphenyl-4-yl | 4-methoxypyrimidin-2-yl | 1H-tetrazol-5-yl | 1HNMR(CD3OD): δ = 2.43 (m, 2H), 3.78-3.90 (m, 6H), 4.20(s, 3H), 4.95(m, 2H), 6.20(d, 1H, J = 6.9 Hz), 7.38-7.85(m, 12H); LCMS (Method A), 1.50 min, m/z (MH)$^+$ = 512. |

TABLE 1-continued

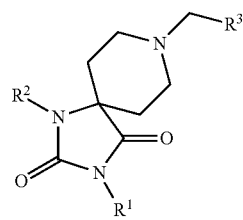

| Ex. No. | IUPAC name | R1 | R2 | R3 | NMR and LCMS |
|---|---|---|---|---|---|
| 1-40 | 2-{[3-biphenyl-4-yl-1-(4-methoxypyrimidin-2-yl)-2,4-dioxo-1,3,8-triazaspiro[4.5]dec-8-yl]methyl}nicotinonitrile | biphenyl-4-yl | 4-methoxypyrimidin-2-yl | 3-cyanopyridin-2-ylmethyl | 1HNMR(CD3OD): δ = 1.93 (m, 2H), 2.96(m, 2H), 3.20-3.26 (m, 4H), 3.97(s, 2H), 4.06(s, 3H), 6.59(d, 1H, J = 6.3 Hz), 7.34-8.00(m, 11H), 8.45 (d, 1H, J = 4.7 Hz), 8.74(m, 1H); LCMS (Method A), 1.80 min, m/z (MH)+ = 546. |
| 1-41 | 3-biphenyl-4-yl-1-(4-methoxypyrimidin-2-yl)-8-{[3-(1H-tetrazol-5-yl)pyridin-2-yl]methyl}-1,3,8-triazaspiro[4.5]decane-2,4-dione | biphenyl-4-yl | 4-methoxypyrimidin-2-yl | [3-(1H-tetrazol-5-yl)pyridin-2-yl]methyl | 1HNMR(CD3OD): δ = 2.42 (m, 2H), 3.76-4.02 (m, 6H), 4.05(s, 2H), 4.18(s, 3H), 6.22(d, 1H, J = 6.8 Hz), 7.37-7.96(m, 12H), 8.28 (d, 1H, J = 4.7 Hz), 8.94(m, 1H); LCMS (Method A), 1.60 min, m/z (MH)+ = 589. |
| 1-42 | 3-biphenyl-4-yl-1-(2-hydroxypyrimidin-4-yl)-8-[(3-methylpyridin-2-yl)methyl]-1,3,8-triazaspiro[4.5]decane-2,4-dione | biphenyl-4-yl | 2-hydroxypyrimidin-4-yl | (3-methylpyridin-2-yl)methyl | 8.52 (d, J = 4.6, 1H), 7.78 (d, J = 6.4, 2H), 7.72 (d, J = 11.0, 2H), 7.47 (m, 3H), 7.37 (m, 2H), 6.22 (d, J = 6.8, 1H), 4.71 (s, 2H), 3.89 (m, 6H), 2.40 (m, 2H), 2.39 (s, 3H). LCMS (Method A): 1.71 min, m/z (MH)+ = 521.0 |
| 1-43 | 3-biphenyl-4-yl-1-(3-hydroxypyridin-2-yl)-8-[(3-methylpyridin-2-yl)methyl]-1,3,8-triazaspiro[4.5]decane-2,4-dione | biphenyl-4-yl | 3-hydroxypyridin-2-yl | (3-methylpyridin-2-yl)methyl | 8.43 (d, J = 4.1, 1H), 8.15 (dd, J = 1.6, 4.6, 1H), 7.77 (d, J = 8.4, 2H), 7.65 (d, J = 8.3, 3H), 7.57 (d, J = 8.7, 2H), 7.51 (dd, J = 1.6, 8.2, 1H), 7.46 (m, 3H), 7.37 (t, J = 7.3, 1H), 7.31 (dd, J = 4.8, 7.8, 1H), 4.55 (s, 2H), 3.91 (m, 2H), 3.68 (d, J = 12.3, 2H), 3.11 (s, 3H), 2.60 (m, 2H), 2.72 (m, 2H). LCMS (Method A): 1.63 min, m/z (MH)+ = 520.2 |

TABLE 1-continued

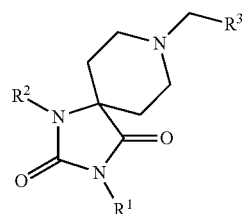

IX

| Ex. No. | IUPAC name | R1 | R2 | R3 | NMR and LCMS |
|---|---|---|---|---|---|
| 1-44 | 4'-{1-(6-hydroxypyrimidin-4-yl)-8-[(3-methylpyridin-2-yl)methyl]-2,4-dioxo-1,3,8-triazaspiro[4.5]dec-3-yl}biphenyl-4-carboxylic acid | biphenyl-4-CO₂H | 6-hydroxypyrimidin-4-yl | (3-methylpyridin-2-yl)methyl | 8.51 (d, J = 4.8, 1H), 8.25 (s, 1H), 8.04 (d, J = 8.3, 2H), 7.90 (d, J = 6.6, 2H), 7.86 (d, J = 8.5, 2H), 7.76 (d, J = 7.6, 1H), 7.62 (d, J = 8.5, 2H), 7.39 (dd, J = 4.8, 7.8, 1H), 6.91 (s, 1H), 4.67 (s, 2H), 3.74 (t, J = 11.0, 2H), 3.62 (d, J = 11.7, 2H), 3.39 (dt, J = 4.3, 14.6, 2H), 2.48 (m, 2H), 2.37 (s, 3H). LCMS (Method A): 1.50 min, m/z (MH)+ = 564.9 |
| 1-45 | 3-biphenyl-4-yl-1-(5-hydroxypyrazin-2-yl)-8-[(3-methylpyridin-2-yl)methyl]-1,3,8-triazaspiro[4.5]decane-2,4-dione | biphenyl-4-yl | 5-hydroxypyrazin-2-yl | (3-methylpyridin-2-yl)methyl | 8.46 (d, J = 4.8, 1H), 8.09 (s, 1H), 7.89 (bs, 1H), 7.82 (d, J = 8.7, 2H), 7.72 (d, J = 7.3, 3H), 7.56 (d, J = 8.5, 2H), 7.48 (t, J = 7.6, 2H), 7.37 (m, 2H), 4.61 (s, 2H), 3.61 (m, 4H), 2.51 (m, 4H), 2.29 (s, H). LCMS (Method A): 1.60 min, m/z (MH)+ = 521.4 |
| 1-46 | Butyl 4-{[3-biphenyl-4-yl-1-(4-hydroxypyrimidin-2-yl)-2,4-dioxo-1,3,8-triazaspiro[4.5]dec-8-yl]methyl}-1-H-imidazole-5-carboxylate | biphenyl-4-yl | 4-hydroxypyrimidin-2-yl | 5-CO₂Bu-imidazol-4-yl | In CD3OD; 7.96 (s, 1H), 7.82(bs, 1H), 7.78 (d, J = 7.0, 2H), 7.66 (d, J = 8.7 Hz, 2H), 7.57 (d, J = 7.0 Hz, 2H), 7.47 (t, J = 7.3 Hz, 2H), 7.40 (m, 1H), 6.20 (d, J = 6.9, 1H), 4.88(s, 2H), 4.38 (t, J = 6.6 Hz, 2H), 3.81 (m, 6H), 2.41 (m, 2H), 1.79 (m, 2H), 1.49 (m, 2H), 0.99 (t, J = 7.4 Hz, 3H). LCMS (Method A): 1.80 min, m/z (MH)+ = 596 |
| 1-47 | Butyl 4-{[3-biphenyl-4-yl-1-(4-methoxypyrimidin-2-yl)-2,4-dioxo-1,3,8-triazaspiro[4.5]dec-8-yl]methyl}-1-H-imidazole-5-carboxylate | biphenyl-4-yl | 4-methoxypyrimidin-2-yl | 5-CO₂Bu-imidazol-4-yl | In CD3OD; 8.45 (d, J = 5.9 Hz, 1H), 7.96(s, 1H), 7.77 (d, J = 6.7, 2H), 7.67 (d, J = 8.7 Hz, 2H), 7.58 (d, J = 6.7 Hz, 2H), 7.47 (t, J = 7.3 Hz, 2H), 7.38 (m, 1H), 6.76 (d, J = 5.9, 1H), 4.88 (s, 2H), 4.36 (t, J = 6.9 Hz, 2H), 4.04(s, 3H), 3.95 (m, 2H), 3.68 (m, 2H), 3.44 (m, 2H), 2.44 (m, 2H), 1.78 (m, 2H), 1.47 (m, 2H), 0.98 (t, J = 7.4 Hz, 3H). LCMS (Method A): 1.90 min, m/z (MH)+ = 610.1 |

TABLE 1-continued

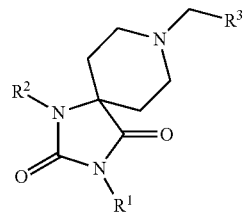

| Ex. No. | IUPAC name | R1 | R2 | R3 | NMR and LCMS |
|---|---|---|---|---|---|
| 1-48 | Butyl 4-{[3-biphenyl-4-yl-1-(6-methoxypyrimidin-4-yl)-2,4-dioxo-1,3,8-triazaspiro[4.5]dec-8-yl]methyl}-1-H-imidazole-5-carboxylate | biphenyl-4-yl | 6-methoxypyrimidin-4-yl | 5-(butoxycarbonyl)-1H-imidazol-4-yl | In CDCl3; 8.70 (s, 1H), 7.40-7.74(m, 11H), 7.28 (s, 1H), 4.45(s, 2H), 4.32 (t, J = 6.9 Hz, 2H), 4.02(s, 3H), 3.79 (m, 2H), 3.46 (m, 2H), 3.13(m, 2H), 2.14 (s, 3H), 1.90 (d, j = 13.8 Hz, 2H), 1.78 (m, 2H), 1.48 (m, 2H), 0.96 (t, J = 7.4 Hz, 3H). LCMS (Method A): 2.0 min, m/z (MH)+ = 610.1 |
| 1-49 | 3-biphenyl-4-yl-1-(4-methoxypyrimidin-2-yl)-8-[(5-methyl-1-H-imidazol-4-yl)methyl]-1,3,8-triazaspiro[4.5]decane-2,4-dione | biphenyl-4-yl | 4-methoxypyrimidin-2-yl | 5-methyl-1H-imidazol-4-yl | In CDCl3; 8.62 (s, 1H), 7.40-7.74(m, 11H), 7.28 (s, 1H), 4.01 (s, 1H), 4.68(s, 2H), 3.54 (m, 2H), 3.04(m, 2H), 2.93 (m, 2H), 2.25(s, 3H), 1.85 (d, J = 13.5 Hz, 2H); LCMS (Method A): 1.60 min, m/z (MH)+ = 524 |
| 1-50 | 4-{[3-biphenyl-4-yl-1-(4-methoxypyrimidin-2-yl)-2,4-dioxo-1,3,8-triazaspiro[4.5]dec-8-yl]methyl}-1-H-imidazole-5-carboxylic acid | biphenyl-4-yl | 4-hydroxypyrimidin-2-yl | 5-carboxy-1H-imidazol-4-yl | In CD3OD; 8.01 (s, 1H), 7.38-7.81(m, 10H), 6.22 (d, J = 6.0 Hz, 1H), 4.78 (s, 2H), 3.76(m, 6H), 2.43(m, 2H),; LCMS (Method A): 1.40 min, m/z (MH)+ = 540 |
| 1-51 | 4-[(3-biphenyl-4-yl-2,4-dioxo-1,3,8-triazaspiro[4.5]dec-8-yl]methyl]-1-H-imidazole-5-carboxylic acid | biphenyl-4-yl | H | 5-carboxy-1H-imidazol-4-yl | In DMSO; 7.36-7.78(m, 9H), 4.61 (s, 2H), 3.4-3.63(m, 6H), 2.43(m, 2H),; LCMS (Method A): 1.40 min, m/z (MH)+ = 446. |

TABLE 1-continued

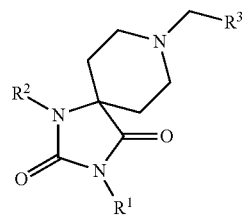

| Ex. No. | IUPAC name | R1 | R2 | R3 | NMR and LCMS |
|---|---|---|---|---|---|
| 1-52 | 4-{[3-biphenyl-4-yl-1-(6-hydroxypyrimidin-4-yl)-2,4-dioxo-1,3,8-triazaspiro[4.5]dec-8-yl]methyl}-1-H-imidazole-5-carboxylic acid | biphenyl-4-yl | 6-hydroxypyrimidin-4-yl | imidazole-5-carboxylic acid (CO2H) | in CD3OD; 8.23 (s, 1H), 8.03(bs, 1H), 7.32-7.72(m, 10H), 4.82 (s, 2H), 3.98(m, 2H), 2.67(m, 4H), 2.38(m, 2H),; LCMS (Method A): 1.40 min, m/z (MH)+ = 539.9 |
| 1-53 | 3-biphenyl-4-yl-1-(6-hydroxypyrimidin-4-yl)-8-[(5-methyl-1-H-imidazol-4-yl)methyl]-1,3,8-triazaspiro[4.5]decane-2,4-dione | biphenyl-4-yl | 6-hydroxypyrimidin-4-yl | 5-methyl-1H-imidazol-4-yl | in CD3OD; 8.84 (s, 1H), 8.08(s, 1H), 7.78 (d, J = 7.0, 2H), 7.66 (d, J = 8.7 Hz, 2H), 7.58 (d, J = 7.0 Hz, 2H), 7.47 (t, J = 7.3 Hz, 2H), 7.40 (m, 1H), 7.28(s, 1H), 4.80 (s, 2H), 3.88(m, 2H), 2.68(m, 4H), 2.41(s, 3H), 2.38(m, 2H),; LCMS (Method A): 1.30 min, m/z (MH)+ = 510 |
| 1-54 | 2-{[3-biphenyl-4-yl-1-(6-hydroxypyrimidin-4-yl)-2,4-dioxo-1,3,8-triazaspiro[4.5]dec-8-yl]methyl}nicotinic acid | biphenyl-4-yl | 6-hydroxypyrimidin-4-yl | nicotinic acid (CO2H-pyridinyl) | 8.76 (m, 1H), 8.53 (d, J = 4.8, 1H), 8.32 (d, J = 6.1, 1H), 8.27 (s, 1H), 8.73 (m, 3H), 7.63 (d, J = 6.4, 2H), 7.57 (dd, J = 5.0, 7.8, 1H), 7.36 (m, 2H), 4.73 (s, 2H), 4.04 (m, 2H), 3.78 (m, 4H), 2.44 (m, 2H), 2.41 (s, 3H). LCMS (Method A): 1.14 min, m/z (MH)+ = 566.0 |
| 1-55 | 3-biphenyl-4-yl-1-(4,6-dihydroxypyrimidin-2-yl)-8-[(3-methylpyridin-2-yl)methyl]-1,3,8-triazaspiro[4.5]decane-2,4-dione | biphenyl-4-yl | 4,6-dihydroxypyrimidin-2-yl | 3-methylpyridin-2-yl | 8.47 (d, J = 4.8, 1H), 7.76 (d, J = 6.1, 2H), 7.70 (d, J = 6.1, 1H), 7.68 (d, J = 6.1, 2H), 7.52 (d, J = 6.2, 2H), 7.42 (m, 2H), 7.38 (m, 1H), 7.32 (m, 1H), 4.32 (s, 2H), 3.67 (m, 2H), 3.54 (m, 2H), 3.38 (m, 2H), 2.39 (s, 3H), 2.27 (m, 2H). LCMS (Method B): 2.61 min, m/z (MH)+ = 537.0 |

TABLE 1-continued

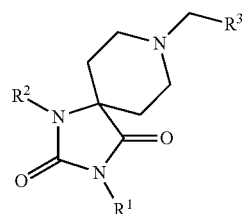

| Ex. No. | IUPAC name | R1 | R2 | R3 | NMR and LCMS |
|---|---|---|---|---|---|
| 1-56 | 3-biphenyl-4-yl-1-(4-hydroxy-6-methoxypyrimidin-2-yl)-8-[(3-methylpyridin-2-yl)methyl]-1,3,8-triazaspiro[4.5]decane-2,4-dione | biphenyl-4-yl | 4-hydroxy-6-methoxypyrimidin-2-yl | (3-methylpyridin-2-yl)methyl | 8.47 (d, J = 4.8, 1H), 7.76 (d, J = 6.1, 2H), 7.70 (d, J = 6.1, 1H), 7.68 (d, J = 6.1, 2H), 7.52 (d, J = 6.2, 2H), 7.40 (m, 4H), 4.48 (s, 2H), 3.88 (m, 2H), 3.59 (m, 4H), 3.38 (m, 2H), 2.39 (s, 3H), 2.39 (m, 2H). LCMS (Method B): 2.81 min, m/z (MH)+ = 551.1 |
| 1-57 | 3-biphenyl-4-yl-1-(4,6-dimethoxypyrimidin-2-yl)-8-[(3-methylpyridin-2-yl)methyl]-1,3,8-triazaspiro[4.5]decane-2,4-dione | biphenyl-4-yl | 4,6-dimethoxypyrimidin-2-yl | (3-methylpyridin-2-yl)methyl | LCMS (Method B): 3.33 min, m/z (MH)+ = 565.1 |
| 1-58 | 3-biphenyl-4-yl-1-(2-hydroxypyridin-4-yl)-8-[(3-methylpyridin-2-yl)methyl]-1,3,8-triazaspiro[4.5]decane-2,4-dione | biphenyl-4-yl | 2-hydroxypyridin-4-yl | (3-methylpyridin-2-yl)methyl | 8.45 (d, J = 4.4, 1H), 7.76 (d, J = 8.5, 2H), 7.71 (d, J = 7.5, 1H), 7.65 (d, J = 8.4, 2H), 7.60 (t, J = 8.7, 3H), 7.46 (t, J = 7.7, 2H), 7.35 (m, 2H), 6.66 (d, J = 1.9, 1H), 6.56 (dd, J = 2.0, 7.1, 1H), 4.58 (s, 2H), 3.94 (dt, J = 3.9, 12.6, 2H), 2.58 (m, 4H), 2.33 (s, 3H). LCMS (Method A): 1.59 min, m/z (MH)+ = 519.9 |
| 1-59 | 2-{3-biphenyl-4-yl-8-[(3-methylpyridin-2-yl)methyl]-2,4-dioxo-1,3,8-triazaspiro[4.5]dec-1-yl}pyrimidine-4-carboxylic acid | biphenyl-4-yl | 4-carboxypyrimidin-2-yl | (3-methylpyridin-2-yl)methyl | 8.87 (d, J = 3.8, 1H), 8.53 (d, J = 2.8, 1H), 7.76 (d, J = 6.4, 1H), 7.70 (d, J = 6.2, 2H), 7.69 (d, J = 6.1, 1H), 7.67 (d, J = 6.2, 2H), 7.60 (d, J = 6.1, 2H), 7.45 (m, 2H), 7.35 (m, 2H), 4.68 (s, 2H), 4.00 (m, 2H), 3.84 (m, 2H), 3.71 (m, 2H), 2.45 (m, 2H), 2.40 (s, 3H). LCMS (Method B): 2.81 min, m/z (MH)+ = 549.0 |

TABLE 1-continued

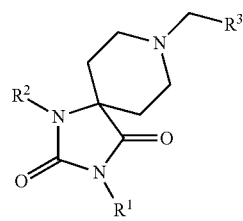

IX

| Ex. No. | IUPAC name | R1 | R2 | R3 | NMR and LCMS |
|---|---|---|---|---|---|
| 1-60 | 6-{3-biphenyl-4-yl-8-[(3-methylpyridin-2-yl)methyl]-2,4-dioxo-1,3,8-triazaspiro[4.5]dec-1-yl}nicotinic acid | biphenyl-4-yl | 5-CO₂H-pyridin-2-yl | 3-methylpyridin-2-yl | 9.12 (m, 1H), 8.54 (m, 1H), 8.41 (m, 2H), 7.67 (m, 3H), 7.67 (m, 2H), 7.61 (t, J = 7.8, 2H), 7.48 (d, J = 6.9, 2H), 7.39 (t, J = 12.0, 2H), 4.74 (m, 2H), 4.05 (m, 2H), 3.97 (m, 2H), 3.84 (d, J = 14.4, 2H), 3.78 (m, 2H), 2.42 (s, 3H). LCMS (Method A): 2.00 min, m/z (MH)+ = 562.1 |
| 1-61 | Methyl 4'-{8-[(3-methylpyridin-2-yl)methyl]-2,4-dioxo-1-pyrimidin-2-yl-1,3,8-triazaspiro[4.5]dec-3-yl}biphenyl-4-carboxylate | 4'-CO₂Me-biphenyl-4-yl | pyrimidin-2-yl | 3-methylpyridin-2-yl | LCMS (Method B): 2.73 min, m/z (MH)+ = 563.0 |
| 1-62 | Methyl 4-[(3-biphenyl-4-yl-2,4-dioxo-1-pyrimidin-2-yl-1,3,8-triazaspiro[4.5]dec-8-yl)methyl]-1-H-imidazole-5-carboxylate | biphenyl-4-yl | pyrimidin-2-yl | 4-CO₂H-1H-imidazol-5-yl | LCMS (Method A): 2.53 min, m/z (MH)+ = 538.0 |
| 1-63 | 4'-{8-[(3-methylpyridin-2-yl)methyl]-2,4-dioxo-1-pyrimidin-2-yl-1,3,8-triazaspiro[4.5]dec-3-yl}biphenyl-4-carboxylic acid | 4'-CO₂H-biphenyl-4-yl | pyrimidin-2-yl | 3-methylpyridin-2-yl | 8.87 (d, J = 3.8, 2H), 8.53 (d, J = 2.8, 1H), 8.19 (d, J = 6.4, 2H), 7.91 (d, J = 6.4, 2H), 7.74 (d, J = 6.2, 2H), 7.68 (d, J = 6.1, 1H), 7.41 (d, J = 6.2, 2H), 7.42 (m, 1H), 7.38 (m, 1H), 4.72 (s, 2H), 4.07 (m, 2H), 3.80 (m, 2H), 3.61 (m, 2H), 2.51 (m, 2H), 2.41 (s, 3H). LCMS (Method B): 2.38 min, m/z (MH)+ = 549.2 |

TABLE 1-continued

IX

| Ex. No. | IUPAC name | R1 | R2 | R3 | NMR and LCMS |
|---|---|---|---|---|---|
| 1-64 | 4-[(3-biphenyl-4-yl-2,4-dioxo-1-pyrimidin-2-yl-1,3,8-triazaspiro[4.5]dec-8-yl)methyl]-1-H-imidazole-5-carboxylic acid | biphenyl-4-yl | pyrimidin-2-yl | 5-carboxy-1H-imidazol-4-yl | 8.59 (d, J = 1.8, 1H), 7.78 (d, J = 6.4, 1H), 7.76 (d, J = 6.4, 2H), 7.65 (m, 2H), 7.58 (d, J = 6.2, 2H), 7.51 (m, 3H), 7.36 (m, 2H), 4.56 (s, 1H), 4.35 (s, 1H), 3.80 (m, 2H), 3.62 (m, 2H), 3.48 (m, 4H), 2.39 (m, 2H), 2.16 (m, 1H). LCMS (Method B): 2.38 min, m/z (MH)+ = 524.0 |
| 1-65 | 5-(4-{8-[(3-carboxypyridin-2-yl)methyl]-2,4-dioxo-1-pyrimidin-2-yl-1,3,8-triazaspiro[4.5]dec-3-yl}phenyl)pyridine-2-carboxylic acid | 4-(6-carboxypyridin-3-yl)phenyl | pyrimidin-2-yl | 3-carboxypyridin-2-yl | LCMS (Method A): 1.16 min, m/z (MH)+ = 550.1 |
| 1-66 | 4'-{8-[(3-methylpyridin-2-yl)methyl]-2,4-dioxo-1-pyrimidin-2-yl-1,3,8-triazaspiro[4.5]dec-3-yl}biphenyl-3-carboxylic acid | 3'-carboxybiphenyl-4-yl | pyrimidin-2-yl | 3-methylpyridin-2-yl | 8.81 (d, J = 4.8, 2H), 8.48 (d, J = 4.5, 1H), 8.28 (s, 1H), 8.03 (d, J = 7.6, 1H), 7.88 (d, J = 7.7, 1H), 7.79 (d, J = 8.2, 2H), 7.70 (d, J = 7.6, 1H), 7.63 (d, J = 8.4, 2H), 7.57 (t, J = 7.6, 1H), 7.38 (t, J = 4.8, 1H), 7.33 (dd, J = 4.8, 7.6, 1H), 4.66 (s, 2H), 4.00 (t, J = 11.0, 2H), 3.73 (d, J = 11.0, 2H), 3.54 (dt, J = 4.6, 15.7, 2H), 2.42 (d, J = 15.6, 2H), 2.36 (s, 3H). LCMS (Method A): 1.50 min, m/z (MH)+ = 549.0 |
| 1-67 | (4'-{8-[(3-methylpyridin-2-yl)methyl]-2,4-dioxo-1-pyrimidin-2-yl-1,3,8-triazaspiro[4.5]dec-3-yl}biphenyl-4-yl)acetic acid | 4'-(carboxymethyl)biphenyl-4-yl | pyrimidin-2-yl | 3-methylpyridin-2-yl | 8.83 (d, J = 4.6, 2H), 8.51 (d, J = 3.9, 1H), 7.77 (d, J = 8.4, 2H), 7.71 (d, J = 7.6, 1H), 7.61 (d, J = 8.7, 4H), 7.39 (m, 3H), 7.34 (m, 1H), 4.66 (s, 2H), 4.02 (t, J = 11.2, 2H), 3.74 (d, J = 12.6, 2H), 3.67 (s, 2H), 3.57 (dt, J = 4.4, 14.2, 2H), 2.43 (m, 2H), 2.38 (s, 3H). LCMS (Method A): 1.47 min, m/z (MH)+ = 563.0 |

TABLE 1-continued

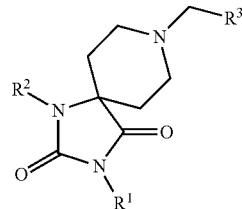

| Ex. No. | IUPAC name | R1 | R2 | R3 | NMR and LCMS |
|---|---|---|---|---|---|
| 1-68 | 3-biphenyl-4-yl-8-[(3-methylpyridin-2-yl)methyl]-1-pyrimidin-4-yl-1,3,8-triazaspiro[4.5]decane-2,4-dione | biphenyl | pyrimidin-4-yl | 3-methylpyridin-2-yl | 9.11 (s, 1H), 8.55 (d, J = 3.9, 1H), 8.50 (d, J = 5.5, 1H), 7.80 (d, J = 8.3, 2H), 7.76 (d, J = 7.5, 1H), 7.68 (d, J = 7.3, 2H), 7.61 (d, J = 8.2, 2H), 7.49 (t, J = 7.8, 2H), 7.40 (m, 3H), 4.77 (s, 2H), 4.07 (t, J = 11.9, 2H), 3.92 (t, J = 10.1, 2H), 3.81 (d, J = 10.5, 2H), 2.44 (m, 2H), 2.43 (s, 3H). LCMS (Method A): 1.80 min, m/z (MH)+ = 505.0 |
| 1-69 | 2-(4-{8-[(3-methylpyridin-2-yl)methyl]-2,4-dioxo-1-pyrimidin-2-yl-1,3,8-triazaspiro[4.5]dec-3-yl}phenyl)cyclopropanecarboxylic acid | 4-(cyclopropanecarboxylic acid)phenyl | pyrimidin-2-yl | 3-methylpyridin-2-yl | 8.55 (bs, 2H), 8.55 (d, J = 4.8, 1H), 7.80 (d, J = 7.6, 1H), 7.75 (d, J = 8.4, 1H), 7.42 (t, J = 8.2, 2H), 7.40 (m, 1H), 7.29 (d, J = 8.5, 2H), 4.72 (s, 2H), 4.00 (t, J = 12.3, 2H), 3.75 (d, J = 12.1, 2H), 3.57 (dt, J = 4.1, 14.4, 2H), 2.53 (m, 1H), 2.42 (s, 3H), 2.41 (m, 2H), 1.90 (m, 1H), 1.57 (m, 1H), 1.40 (m, 1H). LCMS (Method B): 1.30 min, m/z (MH)+ = 513.0 |
| 1-70 | 8-[(3-methylpyridin-2-yl)methyl]-1-(6-methoxypyrimidin-4-yl)-3-(4'-propionylbiphenyl-4-yl)-1,3,8-triazaspiro[4.5]decane-2,4-dione | 4'-propionylbiphenyl-4-yl | 6-methoxypyrimidin-4-yl | 3-methylpyridin-2-yl | 8.70 (s, 1H), 8.53 (d, J = 4.6, 1H), 8.13 (d, J = 8.7, 2H), 7.73 (d, J = 7.5, 1H), 7.69 (d, J = 4.6, 2H), 7.67 (s, 1H, 7.36 (dd, J = 4.8, 7.5, 1H), 4.74 (s, 2H), 4.03 (dt, J = 2.8, 13.3, 2H), 4.01 (s, 3H), 3.86 (dt, J = 4.6, 14.6, 2H), 3.76 (d, J = 12.2, 2H), 3.10 (q, J = 7.1, 2H), 2.41 (s, 3H), 2.40 (d, J = 13.3, 2H), 1.20 (t, J = 7.1, 3H). LCMS (Method B): 2.85 min, m/z (MH)+ = 515.4 |
| 1-71 | 1-(6-hydroxypyrimidin-4-yl)-8-[(3-methylpyridin-2-yl)methyl]-3-(4'-propionylbiphenyl-4-yl)-1,3,8-triazaspiro[4.5]decane-2,4-dione | 4'-propionylbiphenyl-4-yl | 6-hydroxypyrimidin-4-yl | 3-methylpyridin-2-yl | 8.49 (d, J = 4.4, 1H), 8.20 (s, 1H), 8.09 (d, J = 10.5, 2H), 7.67 (d, J = 7.8, 1H), 7.62 (d, J = 7.4, 2H), 7.33 (dd, J = 4.8, 7.6, 1H), 7.28 (s, 1H), 4.60 (s, 2H), 3.98 (t, J = 12.9, 2H), 3.79 (m, 4H), 3.06 (q, 7.4, 2H), 2.38 (s, 3H), 2.34 (d, J = 14.4, 2H), 1.21 (t, J = 7.1, 3H). LCMS (Method B): 2.58 min, m/z (MH)+ = 565.1. |

Table 2 discloses compounds of formula VII as Example 2-1 through Example 2-8 which were prepared according to the analogous general procedure described for Example 1-1 modifying either Step A or Step B as follows: Respective imide/amide (depending on modification of the first/second step, respectively, 1 mmol) was dissolved in acetonitrile (25 mL), sodium hydride (2 mmol) added followed by addition of $R^1X$ or $R^2X$. The resulting mixture was stirred at room temperature for 8 h and then concentrated. In case of acetic acid derivatives, tert-butyl bromoacetate was used as $R^1X$ or $R^2X$ electrophile and the final deprotection of the ester was accomplished by treatment with 25% solution of trifluoroacetic acid in DCM. The products were isolated as salts of trifluoroacetic acid using preparative HPLC (Method C).

TABLE 2

VII

| Ex. No. | IUPAC name | R1 | R2 | R3 | NMR and LCMS |
|---|---|---|---|---|---|
| 2-1 | 3-biphenyl-4-yl-1-methyl-8-[(3-methylpyridin-2-yl)methyl]-1,3,8-triazaspiro[4.5]decane-2,4-dione | biphenyl-4-yl | —Me | (3-methylpyridin-2-yl)methyl | 8.50 (d, J = 4.8, 1H), 7.73 (d, J = 8.5, 3H), 7.64 (d, J = 7.3, 2H), 7.52 (d, J = 8.5, 2H), 7.44 (t, J = 7.3, 2H), 7.36 (m, 2H), 4.63 (s, 2H), 3.91 (t, J = 10.5, 2H), 3.75 (d, J = 10.8, 2H), 3.03 (s, 3H), 2.65 (dt, J = 4.4, 14.5, 2H), 2.36 (s, 3H), 2.23 (d, J = 15.1, 2H). LCMS (Method A): 1.50 min, m/z (MH)+ = 441.0. |
| 2-2 | tert-butyl (3-biphenyl-4-yl-2,4-dioxo-1-pyrazin-2-yl-1,3,8-triazaspiro[4.5]dec-8-yl)acetate | biphenyl-4-yl | pyrazin-2-yl | tert-butyl acetate | LCMS (Method B), 3.00 min, m/z (MH)$^+$ = 514.0. |
| 2-3 | (3-biphenyl-4-yl-2,4-dioxo-1-pyrazin-2-yl-1,3,8-triazaspiro[4.5]dec-8-yl)acetic acid | biphenyl-4-yl | pyrazin-2-yl | —CO2H | 1HNMR(CD3OD): δ = 2.46 (m, 2H), 3.56 (m, 2H), 3.78 (m, 2H), 3.95 (m, 2H), 4.22 (s, 2H), 7.38 (m, 1H), 7.46 (m, 2H), 7.62 (d, 2H, J = 4.6 Hz), 7.69 (d, 2H, J = 4.6 Hz), 7.75 (d, 2H, J = 4.6 Hz), 8.46 (m, 1H), 8.53 (m, 1H), 9.46 (s, 1H); LCMS (Method B), 2.61 min, m/z (MH)$^+$ = 457.9. |
| 2-4 | (3-biphenyl-4-yl-2,4-dioxo-1-pyrimidin-5-yl-1,3,8-triazaspiro[4.5]dec-8-yl)acetic acid | biphenyl-4-yl | pyrimidin-5-yl | —CO2H | 1HNMR(CD3OD): δ = 2.26 (m, 2H), 3.66 (m, 2H), 3.72 (m, 2H), 3.89 (m, 2H), 4.12 (s, 2H), 7.39 (t, 1H, J = 4.6 Hz), 7.46 (m, 2H), 7.61 (d, 2H, J = 4.6 Hz), 7.67 (d, 2H, J = 4.6 Hz), 7.77 (d, 2H, J = 4.6 Hz), 8.96 (s, 2H), 9.32 (s, 1H); LCMS (Method B), 2.48 min, m/z (MH)$^+$ = 457.9. |

TABLE 2-continued

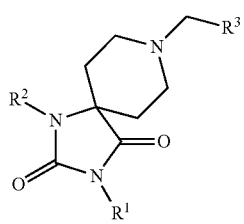

VII

| Ex. No. | IUPAC name | R1 | R2 | R3 | NMR and LCMS |
|---|---|---|---|---|---|
| 2-5 | (3-biphenyl-4-yl-2,4-dioxo-1-pyrimidin-2-yl-1,3,8-triazaspiro[4.5]dec-8-yl)acetic acid | 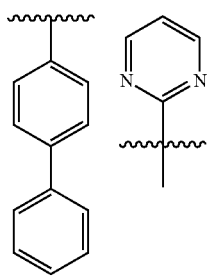 | | —CO2H | 1HNMR(CD3OD): δ = 2.44 (m, 2H), 3.526 (m, 2H), 3.78 (m, 2H), 3.95 (m, 2H), 4.20 (s, 2H), 7.39 (m, 1H), 7.48 (m, 2H), 7.62 (d, 2H, J = 4.6 Hz), 7.69 (d, 2H, J = 4.6 Hz), 7.75 (d, 2H, J = 4.6 Hz), 8.83 (m, 2H); LCMS (Method B), 2.41 min, m/z (MH)+ = 457.9. |
| 2-6 | [3-biphenyl-4-yl-1-(4-methoxypyrimidin-2-yl)-2,4-dioxo-1,3,8-triazaspiro[4.5]dec-8-yl]acetic acid | 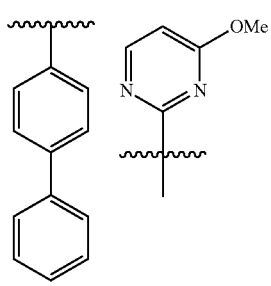 | | —CO2H | 1HNMR(CD3OD): δ = 2.25-2.53 (m, 4H), 3.72-3.93(m, 4H), 4.30(s, 2H), 6.22(d, 1H, J = 7.1 Hz), 7.38-7.81(m, 12H); LCMS (Method A), 1.20 min, m/z (MH)+ = 474. |
| 2-7 | 2,2'-(3-biphenyl-4-yl-2,4-dioxo-1,3,8-triazaspiro[4.5]decane-1,8-diyl)diacetic acid | 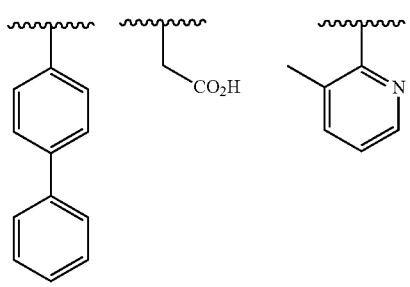 | | | 1HNMR(CD3OD): δ = 2.32 (m, 2H), 2.35 (s, 3H), 2.50 (m, 2H), 3.73(m, 2H), 3.91 (m, 2H), 4.25 (s, 2H), 4.62(s, 2H),7.35-7.76(m, 11H), 8.50(d, 1H, J = 4.2 Hz); LCMS (Method. A), 1.50 min, m/z (MH)+ = 485. |

TABLE 2-continued

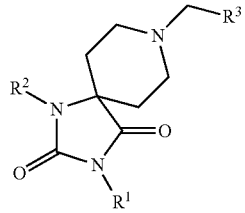

VII

| Ex. No. | IUPAC name | R1 | R2 | R3 | NMR and LCMS |
|---|---|---|---|---|---|
| 2-8 | [3-biphenyl-4-yl-1-(2-ethoxy-2-oxoethyl)-2,4-dioxo-1,3,8-triazaspiro[4.5]dec-8-yl]acetic acid | 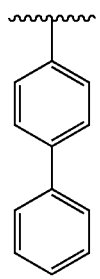 | 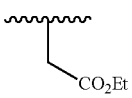 | 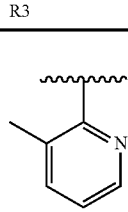 | 1HNMR(CD3OD): δ = 1.19(m, 3H), 2.23-2.50 (m, 3H), 2.43 (s, 3H), 2.94(m, 1H), 3.29-3.84(m, 5H), 4.15 (m, 2H), 6.60-8.41(m, 12H); LCMS (Method A), 1.60 min, m/z (MH)$^+$ = 499. |

Example 3

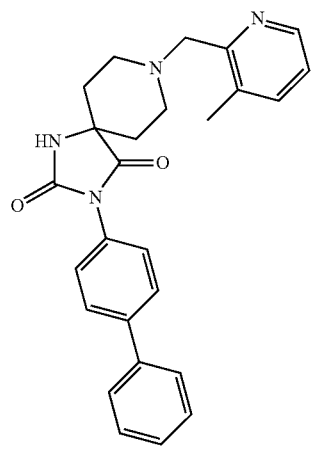

3-biphenyl-4-yl-8-[(3-methylpyridin-2-yl)methyl]-1,3,8-triazaspiro[4.5]decane-2,4-dione (3-1)

Compound 3-1 was prepared according to the general procedure described for Example 1, omitting Step B, and then isolated as salts of trifluoroacetic acid using preparative HPLC (Method C). $^1$HNMR (CDCl$_3$): δ=2.25 (m, 2H), 2.37 (m, 2H), 2.46 (s, 3H), 2.96 (m, 2H), 3.74 (s, 2H), 6.87 (s, 1H), 7.16-7.70 (m, 10H), 8.40 (d, 1H, J=4.2 Hz); LCMS (Method A), 1.50 min, m/z (MH)$^+$=427.

Example 4

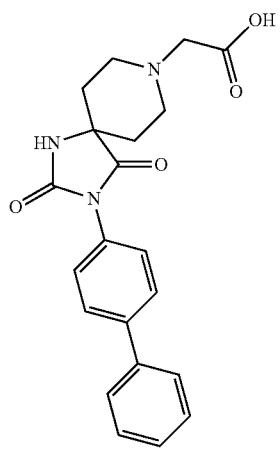

(3-biphenyl-4-yl-2,4-dioxo-1,3,8-triazaspiro[4.5]dec-8-yl)acetic acid (4-1)

Compound 4-1 was prepared according to the general procedure described for Example 1, omitting Step B and isolated as salts of trifluoroacetic acid using preparative HPLC (Method C). $^1$HNMR (CD3OD): δ=2.21-2.51 (m, 4H), 3.67-3.90 (m, 4H), 4.24 (m, 2H), 7.38-7.76 (m, 9H); LCMS (Method A), 1.50 min, m/z (MH)$^+$=380.

Compound Examples 3-2 through 3-12 were prepared according to the general procedure described for Example 1, using a slightly modified intermediate A, 8-tert-butyl 6-ethyl 2,4-dioxo-1,3,8-triazaspiro[4.5]decane-6,8-dicarboxylate, which in turn was prepared from the corresponding substituted ketone, 1-tert-butyl 3-ethyl 4-oxopiperidine-1,3-dicarboxylate. Hydrolysis of the ethyl ester was accomplished according to the general procedure described for Example 1, Step E. The final products were isolated as salts of trifluoroacetic acid using preparative HPLC (Method C).

TABLE 3

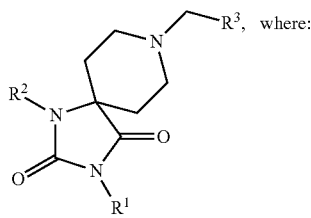 VII   where:

R1 = 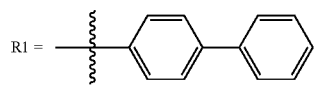

R3 = 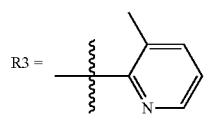 [SMILES: *c1ncccc1C]

| Ex. No | IUPAC name | R2 | R4 | NMR and LCMS |
|---|---|---|---|---|
| 3-2 | ethyl 3-biphenyl-4-yl-1-(4-methoxypyrimidin-2-yl)-8-[(3-methylpyridin-2-yl)methyl]-2,4-dioxo-1,3,8-triazaspiro[4.5]decane-6-carboxylate | 4-OMe pyrimidin-2-yl | —CO2Et | 1HNMR(CDCl3): δ = 1.18 (t, 3H, J = 7.1 Hz), 2.44 (s, 3H), 2.83-3.89(m, 7H), 4.01(s, 3H), 4.11(m, 2H), 4.64(m, 2H), 6.55(d, 1H, J = 5.5 Hz), 7.11-7.72(m, 12H), 8.41 (d, 1H, J = 5.3 Hz); LCMS (Method A), 1.90 min, m/z (MH)+ = 607. |
| 3-3 | ethyl 3-biphenyl-4-yl-1-(4-hydroxypyrimidin-2-yl)-8-[(3-methylpyridin-2-yl)methyl]-2,4-dioxo-1,3,8-triazaspiro[4.5]decane-6-carboxylate | 4-OH pyrimidin-2-yl | —CO2Et | 1HNMR(CDCl3): δ = 1.20 (t, 3H, J = 7.1 Hz), 2.45 (s, 3H), 3.56-3.92(m, 7H), 4.62(m, 2H), 6.23(d, 1H, J = 7.1 Hz), 7.38-7.98(m, 12H), 8.59 (d, 1H, J = 4.6 Hz); LCMS (Method A), 1.90 min, m/z (MH)+ = 593. |
| 3-4 | 3-biphenyl-4-yl-1-(4-hydroxypyrimidin-2-yl)-8-[(3-methylpyridin-2-yl)methyl]-2,4-dioxo-1,3,8-triazaspiro[4.5]decane-6-carboxylic acid | 4-OH pyrimidin-2-yl | —CO2H | 1HNMR(CD3OD): δ = 2.41 (s, 3H), 3.66-4.06(m, 7H), 4.67(m, 2H), 4.64(m, 2H), 6.24(d, 1H, J = 7.1 Hz), 7.39-7.91(m, 12H), 8.59 (d, 1H, J = 4.6 Hz); LCMS (Method A), 1.60 min, m/z (MH)+ = 565. |
| 3-5 | 3-biphenyl-4-yl-8-[(3-methylpyridin-2-yl)methyl]-2,4-dioxo-1,3,8-triazaspiro[4.5]decane-6-carboxylic acid | H | CO2H | 1HNMR(CDCl3): δ = 2.17 (m, 1H), 2.43 (s, 3H), 2.51(m, 1H), 3.10(m, 1H), 3.26(m, 1H), 3.56(m, 1H), 3.72(m, 1H), 3.83 (m, 1H), 4.47 (m, 1H), 7.35-8.55(m, 12H); LCMS (Method A), 1.40 min, m/z (MH)+ = 471. |
| 3-6 | Ethyl 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylate | 6-OH pyrimidin-4-yl | —CO2Et | in CD3OD; 8.54 (d, J = 4.4 Hz, 1H), 8.23(s, 1H), 7.84 (d, J = 6.5 Hz, 2H), 7.76 (d, J = 8.5 Hz, 1H), 7.65 (d, J = 8.2 Hz, 2H), 7.53 (d, J = 8.5 Hz, 2H), 7.45 (m, 2H), 7.39 (m, 1H), 7.37 (s, 1H), 5.14(m, 1H), 4.66 (m, 2H), 4.19 (q, J = 7.4 Hz, J = 14.4 Hz, 2H), 4.08(m, 1H), 3.94(m, 2H), 3.62 (m, 2H), 2.43 (m, 1H), 2.41 (s, 3H), 1.18(t,, J = 7.1 Hz, 3H). LCMS (Method C): 1.20 min, m/z (MH)+ = 593 |

TABLE 3-continued

| 3-7 | 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid | 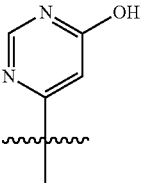 [SMILES: *c1cc(O)ncn1] | —CO2H | In DMSO; 8.52 (d, J = 4.6 Hz, 1H), 8.25(s, 1H), 7.83 (d, J = 8.5 Hz, 2H), 7.78 (d, J = 7.6 Hz, 1H), 7.72 (d, J = 7.6 Hz, 2H), 7.44 (m, 4H), 7.39 (m, 1H), 6.87 (s, 1H), 4.86(m, 1H), 4.68 (s, 2H), 3.87(m, 2H), 3.60 (m, 2H), 3.27 (m, 1H), 2.53(m, 1H), 2.34 (s, 3H). LCMS (Method C): 1.05 min, m/z (MH)+ = 565.1 |
| --- | --- | --- | --- | --- |
| 3-8 | 3-biphenyl-4-yl-8-[(3-methylpyridin-2-yl)methyl]-2,4-dioxo-1-pyrimidin-2-yl-1,3,8-triazaspiro[4.5]decane-6-carboxylic acid | 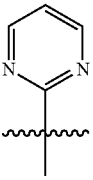 | —CO2H | in CD3OD; 8.85 (bs, 1H), 8.55(d, J = 4.6 Hz, 1H), 7.84 (d, J = 7.8 Hz, 2H), 7.80 (d, J = 8.3 Hz, 1H), 7.69 (d, J = 7.3 Hz, 2H), 7.57 (d, J = 8.3 Hz, 2H), 7.50 (m, 2H), 7.46 (m, 1H), 7.43 (m, 1H), 5.06(m, 1H), 4.76 (m, 2H), 4.18-3.39 (m, 5H), 2.43 (m, 1H), 2.41 (s, 3H). LCMS (Method A): 1.63 min, m/z (MH)+ = 549 |
| 3-9 | Ethyl 3-biphenyl-4-yl-1-(6-methoxypyrimidin-4-yl)-8-[(3-methylpyridin-2-yl)methyl]-2,4-dioxo-1,3,8-triazaspiro[4.5]decane-6-carboxylate | 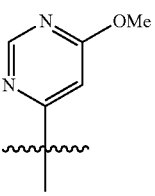 | —CO2Et | LCMS (Method B): 2.52 min, m/z (MH)+ = 607.4. |
| 3-10 | Ethyl 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylate | 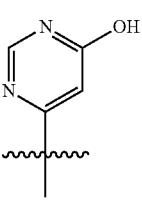 | —CO2Et | 8.59 (d, J = 4.4, 1H), 8.18 (s, 1H), 8.09 (d, J = 10.5, 2H), 7.67 (d, J = 7.8, 1H), 7.62 (d, J = 7.4, 2H), 7.33 (dd, J = 4.8, 7.6, 1H), 7.28 (s, 1H), 5.21 (m, 1H), 4.42 (dd, J = 50, 10, 2H), 4.18 (q, J = 5.6, 2H), 4.03 (m, 2H), 3.79 (m, 4H), 2.47 (s, 3H), 1.23 (1, J = 7.1, 3H). LCMS (Method B): 2.83 min, m/z (MH)+ = 593.1, first eluted enantiomer (AD). |
| 3-11 | 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid | 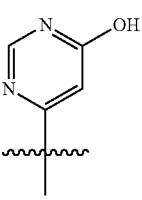 | —CO2H | 8.59 (d, J = 4.4, 1H), 8.18 (s, 1H), 8.09 (d, J = 10.5, 2H), 7.67 (d, J = 7.8, 1H), 7.62 (d, J = 7.4, 2H), 7.33 (dd, J = 4.8, 7.6, 1H), 7.28 (s, 1H), 5.11 (m, 1H), 4.17 (m, 1H), 4.10 (m, 1H), 3.91 (m, 1H), 3.68 (m, 2H), 2.48 (m, 2H), 2.41 (s, 3H), LCMS (Method B): 2.83 min, m/z (MH)+ = 593.1, first elated enantiomer (AD). |

TABLE 3-continued

| 3-12 | 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid | 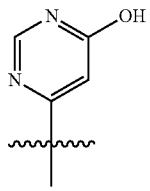 | —CO2H | 8.59 (d, J = 4.4, 1H), 8.18 (s, 1H), 8.09 (d, J = 10.5, 2H), 7.67 (d, J = 7.8, 1H), 7.62 (d, J = 7.4, 2H), 7.33 (dd, J = 4.8, 7.6, 1H), 7.28 (s, 1H), 5.11 (m, 1H), 4.17 (m, 1H), 4.10 (m, 1H), 3.91 (m, 1H), 3.68 (m, 2H), 2.48 (m, 2H), 2.41 (s, 3H), LCMS (Method B): 2.83 min, m/z (MH)+ = 593.1, second elated enantiomer (AD). |

Example 5

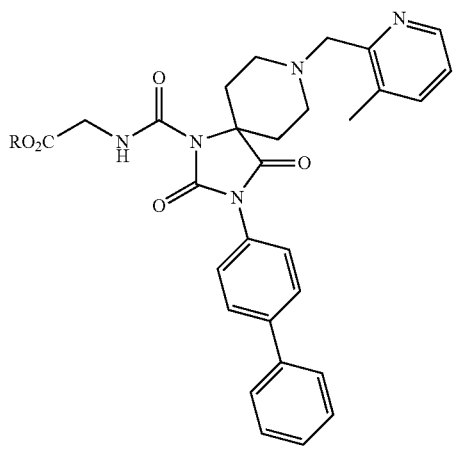

where:
R = ethyl (5-1)
R = t-butyl (5-2)

ethyl [({3-biphenyl-4-yl-8-[(3-methylpyridin-2-yl)methyl]-2,4-dioxo-1,3,8-triazaspiro[4.5]dec-6-yl}carbonyl)amino]acetate(5-1)

Compound 5-1 was prepared according to the general procedure described for Example 1, modifying Step B as follows: The product of Step A (1 mmol) was dissolved in DMF (5 mL) and sodium hydride (2 mmol) was added followed by addition of ethyl N-(oxomethylene)glycinate (2 mmol) (R=Et). The resulting mixture was stirred at room temperature for 1 h. The product was isolated as salt of trifluoroacetic acid using preparative HPLC (Method C).
R=Et, LCMS (Method B), 3.02 min, m/z (MH)$^+$=556.3.

tert-butyl [({3-biphenyl-4-yl-8-[(3-methylpyridin-2-yl)methyl]-2,4-dioxo-1,3,8-triazaspiro[4.5]dec-6-yl}carbonyl)amino]acetate(5-2)

Compound 5-2 was prepared according to the general procedure described for Example 1, modifying Step B as follows: The product of Step A (1 mmol) was dissolved in DMF (5 mL) and sodium hydride (2 mmol) was added followed by addition of ethyl t-butyl N-(oxomethylene)glycinate (2 mmol) (R=T-Bu). The resulting mixture was stirred at room temperature for 1 h. The product was isolated as salt of trifluoroacetic acid using preparative HPLC (Method C).
R=t-butyl, LCMS (Method B), 4.17 min, m/z (MNa)$^+$=601.1.

Example 6

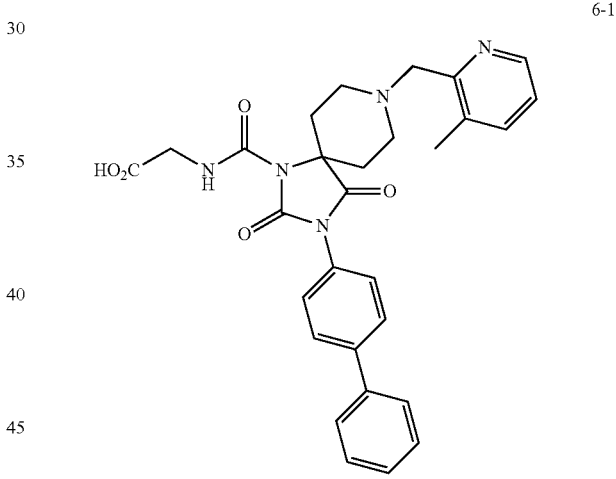

6-1

[({3-biphenyl-4-yl-8-[(3-methylpyridin-2-yl)methyl]-2,4-dioxo-1,3,8-triazaspiro[4.5]dec-6-yl}carbonyl)amino]acetic acid (6-1)

Compound 5-2 was treated with 25% solution of trifluoroacetic acid in DCM for 12 h and concentrated. The product was isolated as salt of trifluoroacetic acid using preparative HPLC (Method C). 1HNMR (CD3OD3): δ=2.37 (s, 3H), 2.42 (m, 2H), 3.46 (m, 2H), 3.74 (m, 2H), 3.95 (m, 2H), 4.01 m (2H), 4.67 (s, 2H), 7.36 (m, 2H), 7.47 (m, 2H), 7.64 (d, 2H, J=5.6 Hz), 7.68 (d, 2H, J=5.6 Hz), 7.70 (d, 1H, J=5.6 Hz), 7.79 (d, 2H, J=5.6 Hz), 8.51 (m, 1H), 8.79 (m, 1H); LCMS (Method B), 2.76 min, m/z (MH)+=527.9.

TABLE 4 depicts compounds of Examples 5-3 through 5-7 which were prepared via analogous methods to those described for Examples 5 and 6.

TABLE 4

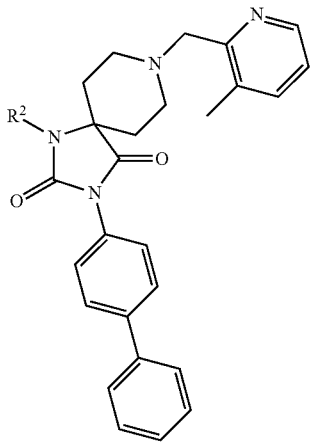

| Ex. No. | IUPAC name | R | NMR and LCMS |
|---|---|---|---|
| 5-3 | 2-[({3-biphenyl-4-yl-8-[(3-methylpyridin-2-yl)methyl]-2,4-dioxo-1,3,8-triazaspiro[4.5]dec-1-yl}carbonyl)amino]-2-methylpropanoic acid | 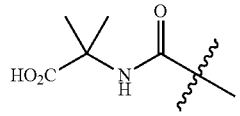 | 8.83 (s, 1H), 8.51 (d, J = 3.8, 1H), 7.78 (d, J = 4.4, 2H), 7.76 (d, J = 6.4, 1H), 7.73 (d, J = 6.4, 2H), 7.65 (d, J = 6.2, 2H), 7.47 (m, 2H), 7.36 (m, 2H), 4.67 (s, 2H), 4.10 (m, 2H), 3.95 (m, 2H), 3.74 (m, 2H), 3.46 (m, 2H), 2.46 (m, 2H), 2.38 (s, 3H), 1.62 (s, 6H). LCMS (Method B): 2.92 min, m/z (MH)+ = 556.4. |
| 5-4 | (2R)-2-[({3-biphenyl-4-yl-8-[(3-methylpyridin-2-yl)methyl]-2,4-dioxo-1,3,8-triazaspiro[4.5]dec-1-yl}carbonyl)amino]propanoic acid | 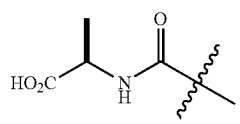 [SMILES: *C(=O)N[C@H](C)C(=O)O] | 8.83 (s, 1H), 8.51 (d, J = 3.8, 1H), 7.78 (d, J = 4.4, 2H), 7.76 (d, J = 6.4, 1H), 7.73 (d, J = 6.4, 2H), 7.65 (d, J = 6.2, 2H), 7.47 (m, 2H), 7.36 (m, 2H), 4.67 (s, 2H), 4.49 (m, 1H), 4.10 (m, 2H), 3.95 (m, 2H), 3.74 (m, 2H), 3.46 (m, 2H), 2.46 (m, 2H), 2.38 (s, 3H), 1.52 (d, J = 3.8, 3H). LCMS (Method B): 2.86 min, m/z (MH)+ = 542.1. |
| 5-5 | (2S)-2-[({3-biphenyl-4-yl-8-[(3-methylpyridin-2-yl)methyl]-2,4-dioxo-1,3,8-triazaspiro[4.5]dec-1-yl}carbonyl)amino]propanoic acid | 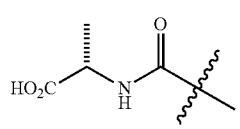 | 8.83 (s, 1H), 8.51 (d, J = 3.8, 1H), 7.78 (d, J = 4.4, 2H), 7.76 (d, J = 6.4, 1H), 7.73 (d, J = 6.4, 2H), 7.65 (d, J = 6.2, 2H), 7.47 (m, 2H), 7.36 (m, 2H), 4.67 (s, 2H), 4.49 (m, 1H), 4.10 (m, 2H), 3.95 (m, 2H), 3.74 (m, 2H), 3.46 (m, 2H), 2.46 (m, 2H), 2.38 (s, 3H), 1.52 (d, J = 3.8, 3H). LCMS (Method B): 2.86 min, m/z (MH)+ = 542.1. |
| 5-6 | N-({3-biphenyl-4-yl-8-[(3-methylpyridin-2-yl)methyl]-2,4-dioxo-1,3,8-triazaspiro[4.5]dec-1-yl}carbonyl)-L-serine | 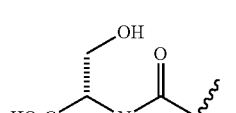 | 8.83 (s, 1H), 8.51 (d, J = 3.8, 1H), 7.78 (d, J = 4.4, 2H), 7.76 (d, J = 6.4, 1H), 7.73 (d, J = 6.4, 2H), 7.65 (d, J = 6.2, 2H), 7.47 (m, 2H), 7.36 (m, 2H), 4.67 (s, 2H), 4.49 (m, 1H), 4.10 (m, 2H), 4.00 (ddd, J = 50, 6, 1.1, 2H), 3.95 (m, 2H), 3.74 (m, 2H), 3.46 (m, 2H), 2.46 (m, 2H), 2.38 (s, 3H). LCMS (Method B): 2.69 min, m/z (MH)+ = 558.1. |
| 5-7 | 4-{3-biphenyl-4-yl-8-[(3-methylpyridin-2-yl)methyl]-2,4-dioxo-1,3,8-triazaspiro[4.5]dec-1-yl}-4-oxobutanoic acid | 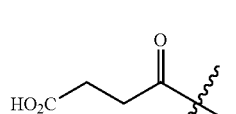 | 8.51 (d, J = 3.8, 1H), 7.78 (d, J = 4.4, 2H), 7.76 (d, J = 6.4, 1H), 7.73 (d, J = 6.4, 2H), 7.65 (d, J = 6.2, 2H), 7.47 (m, 2H), 7.36 (m, 2H), 4.67 (s, 2H), 4.49 (m, 1H), 4.10 (m, 2H), 3.95 (m, 2H), 3.74 (m, 2H), 3.46 (m, 2H), 2.72 (m, 2H), 2.38 (s, 3H). LCMS (Method B): 2.81 min, m/z (MH)+ = 527.1. |

Example 7

4'-{1-(6-methoxypyrimidin-4-yl)-8-[(3-methylpyridin-2-yl)methyl]-2,4-dioxo-1,3,8-triazaspiro[4.5]dec-3-yl}biphenyl-4-carboxylic acid (7-1)

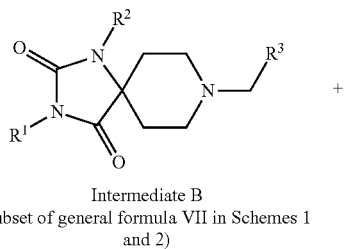

Intermediate B
(subset of general formula VII in Schemes 1 and 2)

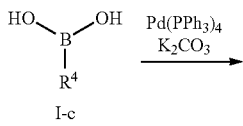

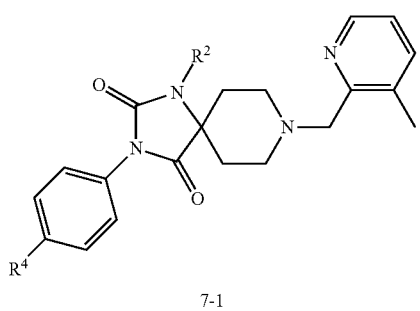

7-1

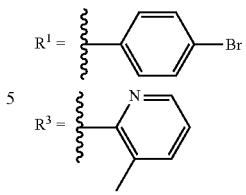

It should be noted that, Intermediate B is a subset of the compounds of formula VII found in general Schemes 1 and 2. Intermediate B was prepared according to the general procedure described in Example 1, Steps A-D, where four equivalents of 1,4-dibromobenzene were substituted for the 4-iodobiphenyl in Step A. The 1,4-dibromo benzene corresponds to the group, $R^1$—X, as depicted in General Scheme 1.

A reaction of mixture of 0.56 mmol of 3-(4-bromophenyl)-1-(6-methoxypyrimidin-4-yl)-8-[(3-methylpyridin-2-yl)methyl]-1,3,8-triazaspiro[4.5]decane-2,4-dione, (Intermediate B where R2=6-methoxypyrimidin-4-yl), 1.41 mmol of 4-(dihydroxyboryl)benzoic acid (corresponding to compound, 1-c, where R4=4-(hydroxycarbonyl)phenyl), 0.09 mmol of tetrakis(triphenylphosphine)palladium(0), and 2N solution of potassium carbonate (0.9 ml, 1.7 mmol) in 6 ml of DMF was heated at 140° C. for 40 min in a microwave. The mixture was filtered and solids rinsed with methanol. It was evaporated under reduced pressure to give the crude product. The residue was purified by Mass-directed HPLC to yield a white solid; 7-1. $^1$NMR (CDCl$_3$): δ=2.37 (m, 2H), 2.41 (s, 3H), 3.75 (m, 2H), 3.88 (m, 2H), 4.01 (s, 3H), 4.04 (m, 2H), 4.87 (s, 2H), 7.37 (m, 1H), 7.62 (d, J=8.5 Hz, 2H), 7.72 (m, 2H), 7.77 (d, J=8.5 Hz), 7.83 (d, J=8.5 Hz, 2H), 8.12 (d, J=8.5 Hz, 2H), 8.52 (m, 1H), 8.70 (s, 1H); LCMS @1.71 min (method A), m/z (MH)$^+$=579.

Table 5 depicts compounds of Example 7-1 through 7-15 which were prepared as described for Example 7-1 and represented by formula VII.

TABLE 5

VII

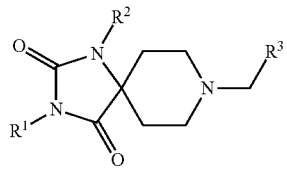

where $R^1$ =

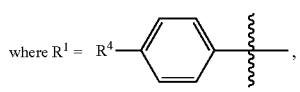

, $R^3$ =

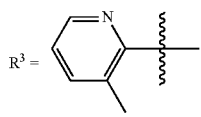 [SMILES: *c1ncccc1C]

| Ex. No. | IUPAC name | R4 | R2 | NMR and LCMS |
|---|---|---|---|---|
| 7-1 | 4'-{1-(6-methoxypyrimidin-4-yl)-8-[(3-methylpyridin-2-yl)methyl]-2,4-dioxo-1,3,8-triazaspiro[4.5]dec-3-yl}biphenyl-4-carboxylic acid | benzoic acid (4-carboxyphenyl) | 6-methoxypyrimidin-4-yl | 1HNMR(CDCl3): δ = 2.37 (m, 2H), 2.41(s, 3H), 3.75 (m, 2H), 3.88(m, 2H), 4.01(s, 3H), 4.04(m, 2H), 4.87(s, 2H), 7.37(m, 1H), 7.62(d, J = 8.5 Hz, 2H), 7.72(m, 2H), 7.77(d, J = 8.5 Hz), 7.83(d, J = 8.5 Hz, 2H), 8.12 (d, J = 8.5 Hz, 2H), 8.52 (m, 1H), 8.70 (s, 1H); LCMS (Method A): 1.71 min, m/z (MH)+ = 579. |

TABLE 5-continued

| 7-2 | 4'-{1-(6-methoxypyrimidin-4-yl)-8-[(3-methylpyridin-2-yl)methyl]-2,4-dioxo-1,3,8-triazaspiro[4.5]dec-3-yl}-2-methylbiphenyl-4-carboxylic acid | | | 1HNMR(CD$_3$OD): δ = 2.23 (m, 2H), 2.33(s, 3H), 2.46(s, 3H), 3.45 (m, 2H), 3.73(m, 4H), 4.00(s, 3H), 4.42(s, 2H), 7.28-7.34(m, 2H), 7.49(d, J = 8.4 Hz, 2H), 7.57(d, J = 8.4 Hz, 2H), 7.68 (s, 1H), 7.70(d, J = 7.5 Hz, 1H), 7.86(d, J = 8.5 Hz, 1H), 7.94 (s, 1H), 8.45 (m, 1H), 8.67 (s, 1H); LCMS (Method A); 1.74 min, m/z (MH)+ = 593. |
|---|---|---|---|---|
| 7-3 | 4'-{1-(6-methoxypyrimidin-4-yl)-8-[(3-methylpyridin-2-yl)methyl]-2,4-dioxo-1,3,8-triazaspiro[4.5]dec-3-yl}-3-methylbiphenyl-4-carboxylic acid | | | 1HNMR(CD$_3$OD): δ = 2.11(m, 2H), 2.45(s, 3H), 2.60(s, 3H), 3.26 (m, 2H), 3.52(m, 2H), 3.63(m, 2H), 3.98(s, 3H), 4.25(s, 2H), 7.29(m, 1H), 7.48(d, J = 8.0 Hz, 1H), 7.50 (s, 1H), 7.54(d, J = 8.2 Hz, 2H), 7.64 (s, 1H), 7.68(d, J = 8.0 Hz, 1H), 7.74 (d, J = 8.2 Hz, 2H), 7.76(m, 1H), 8.40 (m, 1H), 8.62 (s, 1H); LCMS (Meth. A); 1.77 min, m/z (MH)+ = 593. |
| 7-4 | 2-fluoro-4'-{1-(6-methoxypyrimidin-4-yl)-8-[(3-methylpyridin-2-yl)methyl]-2,4-dioxo-1,3,8-triazaspiro[4.5]dec-3-yl}biphenyl-4-carboxylic acid | | | $^1$HNMR(CD$_3$OD): δ = 2.40(m, 2H), 2.42(s, 3H), 3.77(m, 2H), 3.86(m, 2H), 4.01(s, (3H), 4.06(m, 2H), 4.76(s, 2H), 7.36(m, 1H), 7.64-7.72(m, 7H), 7.83(m, 1H), 7.93(m, 1H), 8.54 (m, 1H), 8.71 (s, 1H); LCMS (Method A); 1.73 min, m/z (MH)+ = 597. |
| 7-5 | 2-methyl-4'-{8-(3-methylpyridin-2-yl)methyl]-2,4-dioxo-1-pyrazin-2-yl-1,3,8-triazaspiro[4.5]dec-3-yl}biphenyl-4-carboxylic acid | | | 1HNMR(CD$_3$OD): δ = 2.0, (m, 2H), 2.33(s, 3H), 2.49(s, 3H), 2.85 (m, 2H), 3.07(m, 4H), 3.86 (s, 2H), 7.24(m, 2H), 7.48(d, J = 8.3 Hz, 2H), 7.55(d, J = 8.3 Hz, 2H), 7.64(d, J = 7.5 Hz,1H), 7.82(d, J = 7.5 Hz, 1H) , 7.89 (s, 1H), 8.29 (d, J = 4.2 Hz, 1H), 8.40 (m, 1H), 8.51(m, 1H), 9.26 (s, 1H); LCMS (Method A); 1.61 min, m/z (MH)+ = 563. |
| 7-6 | 2-methyl-4'-{1-(6-methylpyrazin-2-yl)-8-[(3-methylpyridin-2-yl)methyl]-2,4-dioxo-1,3,8-triazaspiro[4.5]dec-3-yl}biphenyl-4-carboxylic acid | | | $^1$HNMR(CD$_3$OD): δ = 2.0(m, 2H), 2.33(s, 3H), 2.51(s, 3H), 2.52(s, 3H), 2.88 (m, 2H), 3.11(m, 4H), 3.85 (s, 2H), 7.24(m, 2H), 7.48(d, J = 8.3 Hz, 2H), 7.55(d, J = 8.3 Hz, 2H), 7.64(d, J = 7.5 Hz, 1H), 7.84(d, J = 7.5 Hz, 1H), 7.90 (s, 1H), 8.29 (d, J = 4.2 Hz, 1H), 8.31(s, 1H), 9.06 (m, 1H); LCMS (Method A); 1.55 min, m/z (MH)+ = 577. |
| 7-7 | 4'-{1-(6-methylpyrazin-2-yl)-8-[(3-methylpyridin-2-yl)ethyl]-2,4-dioxo-1,3,8-triazaspiro[4.5]dec-3-yl}biphenyl-4-carboxylic acid | | | $^1$HNMR(CD$_3$OD): δ = 1.94(m, 2H), 2.50(s, 3H), 2.55(s, 3H), 2.80 (m, 2H), 3.05-3.11(m, 4H), 3.79 (s, 2H), 7.24(m, 1H), 7.55(d, J = 8.5 Hz, 2H), 7.62(d, J = 7.6 Hz, 1H), 7.66(d, J = 8.3 Hz, 2H), 7.78(d, J = 8.5 Hz, 2H), 8.04(d, J = 8.3 Hz, 2H), 8.27(d, J = 4.3 Hz, 1H), 8.29(s, 1H), 9.04 (m, 1H); LCMS (Method A); 1.60 min, m/z (MH)+ = 563. |
| 7-8 | 2-methyl-4'-[8-[(3-methylpyridin-2-yl)methyl]-1-(6-methylpyrimidin-4-yl)-2,4-dioxo-1,3,8-triazaspiro[4.5]dec-3-yl]biphenyl-4-carboxylic acid | | | $^1$HNMR(CD$_3$OD): δ = 1.90(m, 2H), 2.32 (s, 3H), 2.50(s, 3H), 2.53 (s, 3H), 2.89(m, 2H), 3.11(m, 2H), 3.48 (m, 2H), 3.85 (s, 2H), 7.26(m, 2H), 7.48(d, J = 8.4 Hz, 2H), 7.52(d, J = 8.4 Hz, 2H), 7.66(d, J = 7.5 Hz, 1H), 7.82 (d, J = 7.5 Hz, 1H), 7.89 (s, 1H), 8.20 (s, 1H), 8.29 (d, J = 4.3 Hz, 1H), 8.83 (s, 1H); LCMS (Method A); 1.62 min, m/z (MH)+ = 577. |

TABLE 5-continued

| # | Name | Structure 1 | Structure 2 | Data |
|---|---|---|---|---|
| 7-9 | 4'-[8-[(3-methylpyridin-2-yl)methyl]-1-(6-methylpyrimidin-4-yl)-2,4-dioxo-1,3,8-triazaspiro[4.5]dec-3-yl]biphenyl-4-carboxylic acid | phenyl-COOH | 6-methylpyrimidin-4-yl | $^1$HNMR(CD$_3$OD): δ = 1.90(m, 2H), 2.50(s, 3H), 2.53 (s, 3H), 2.89(m, 2H), 3.10(m, 2H), 3.48(m, 2H), 3.84(s, 2H), 7.25(m, 1H), 7.54(d, J = 8.2 Hz, 2H), 7.64(m, 1H), 7.67(d, J = 8.2 Hz, 2H), 7.80(d, J = 8.1 Hz, 2H), 8.05(d, J = 7.7 Hz, 2H), 8.20(s, 1H), 8.29 (d, J = 4.1 Hz, 1H), 8.83 (s, 1H); LCMS (Method A); 1.60 min, m/z (MH)+ = 563. |
| 7-10 | 2-methyl-4'-{8-[(3-methylpyridin-2-yl)methyl]-2,4-dioxo-1-[6-(trifluoromethyl)pyrimidin-4-yl]-1,3,8-triazaspiro[4.5]dec-3-yl}biphenyl-4-carboxylic acid | 2-methylphenyl-COOH | 6-(trifluoromethyl)pyrimidin-4-yl | $^1$HNMR(CD$_3$OD): δ = 2.01(m, 2H), 2.33(s, 3H), 2.53 (s, 3H), 3.01(m, 2H), 3.22(m, 2H), 3.54(m, 2H), 3.95(s, 2H), 7.27 (m, 2H), 7.49(d, J = 8.4 Hz, 2H), 7.56(d, J = 8.4 Hz, 2H), 7.64(d, J = 7.5 Hz, 1H), 7.84(d, J = 7.8 Hz, 1H), 7.92 (s, 1H), 8.33(d, J = 4.5 Hz, 1H), 8.75(s, 1H), 9.12(s, 1H); LCMS (Method A); 1.87 min, m/z (MH)+ = 631. |
| 7-11 | 1-(6-methoxypyrimidin-4-yl)-8-[(3-methylpyridin-2-yl)methyl]-3-[4'-(1H-pyrazol-5-yl)biphenyl-4-yl]-1,3,8-triazaspiro[4.5]decane-2,4-dione | phenyl-(1H-pyrazol-5-yl) | 6-methoxypyrimidin-4-yl | LCMS (Method A); 1.81 min, m/z (MH)+ = 601.1. |
| 7-12 | 1-(6-hydroxypyrimidin-4-yl)-8-[(3-methylpyridin-2-yl)methyl]-3-[4'-(1H-pyrazol-5-yl)biphenyl-4-yl]-1,3,8-triazaspiro[4.5]decane-2,4-dione | phenyl-(1H-pyrazol-5-yl) | 6-hydroxypyrimidin-4-yl | LCMS (Method A); 1.51 min, m/z (MH)+ = 587.1 |
| 7-13 | 1-(6-methoxypyrimidin-4-yl)-8-[(3-methylpyridin-2-yl)methyl]-3-[4'-(5-oxopyrazolidin-3-yl)biphenyl-4-yl]-1,3,8-triazaspiro[4.5]decane-2,4-dione | phenyl-(5-oxopyrazolidin-3-yl) | 6-methoxypyrimidin-4-yl | LCMS (Method A); 1.66 min, m/z (MH)+ = 619.1 |
| 7-14 | 1-(6-hydroxypyrimidin-4-yl)-8-[(3-methylpyridin-2-yl)methyl]-3-[4'-(1 morpholin-4-yl)biphenyl-4-yl]-1,3,8-triazaspiro[4.5]decane-2,4-dione | phenyl-(morpholin-4-yl) | 6-hydroxypyrimidin-4-yl | $^1$HNMR(DMSO): δ = 12.46-13.02 (b, 1H), 9.80-10.46 (b, 1H), 8.52 (d, J = 4.6 Hz, 1H), 8.27 (s, 1H), 7.75-7.78 (m, 3H), 7.62, (d, J = 8.8 Hz, 2H), 7.52 (d, J = 8.5 Hz, 2H), 7.38-7.40 (dd, 4.9, 7.5 Hz, 1H), 7.05 (d, J = 8.7 Hz, 2H), 6.92 (s, 1H), 4.68 (s, 2H), 3.74-3.79 (m, 6H), 3.62 (m, 2H), 3.34-3.40 (dt, J = 4.3, 14.5 Hz, 2H), 3.16-3.18 (m, 4H), 2.46 (m, 2H), 2.35 (s, 3H). LCMS (Method A); 1.56 min, m/z (MH)+ = 606.1. |

TABLE 5-continued

| 7-15 | 4-(6-{3-(4-bromophenyl)-8-[(3-methylpyridin-2-yl)methyl]-2,4-dioxo-1,3,8-triazaspiro[4.5]dec-1-yl}pyrimidin-4-yl)benzoic acid | | | 1HNMR(DMSO-d6): δ = 2.38 (s, 3H), 2.50 (m, 2H), 3.56-3.79 (m, 6H), 4.73 (s, 2H), 7.38 (m, 1H), 7.52-7.78 (m, 5H), 8.12 (d, J = 8.4 Hz, 2H), 8.23 (d, J = 8.4 Hz, 2H), 8.53 (m, 2H), 8.75 (s, 1H), 9.20 (s, 1H); LCMS (Method A); 1.78 min, m/z (MH)+ = 627. |
|---|---|---|---|---|

Example 8

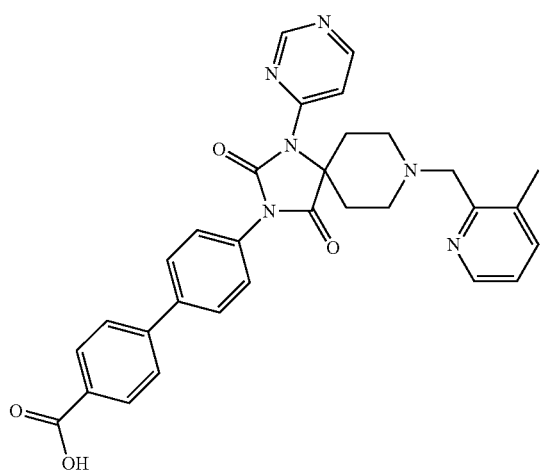

4'-{8-[(3-methylpyridin-2-yl)methyl]-2,4-dioxo-1-pyrimidin-4-yl-1,3,8-triazaspiro[4.5]dec-3-yl}biphenyl-4-carboxylic acid (8-1)

Intermediate C (subset of general formula IX in Scheme 2)

It should be noted that, Intermediate C is a subset of the compounds of formula IX found in general Scheme 2. Intermediate C was prepared according to the general procedure described in Example 1, Steps A, C and D respectively, where four equivalents of 1,4-dibromobenzene were substituted for the 4-iodobiphenyl in Step A. The 1,4-dibromo benzene corresponds to the group, R[1]—X, as depicted in General Scheme 2.

Step A—tert-butyl 4'-{8-[(3-methylpyridin-2-yl)methyl]-2,4-dioxo-1,3,8-triazaspiro[4.5]dec-3-yl}biphenyl-4-carboxylate (8-A)

A reaction of a mixture of 3-(4-bromophenyl)-8-[(3-methylpyridin-2-yl)methyl]-1,3,8-triazaspiro[4.5]decane-2,4-dione (Intermediate C, 640 mg, 1.49 mmol), [4-(tert-butoxycarbonyl)phenyl]boronic acid (497 mg, 2.24 mmol), tetrakis(triphenylphosphine)palladium(0) (138 mg, 0.12 mmol), and 2N solution of potassium carbonate (1.96 ml, 3.72 mmol) in 14 ml of DMF was heated at 120° C. for 40 minute in a microwave. The mixture was filtered through celite and washed with MeOH. The filtrate was evaporated under reduced pressure and the residue was purified by column chromatography on silica gel, eluting with dichloromethane/ethyl acetate/ammonia (2M in MeOH) to give Compound 8-A as a white solid. LCMS (Method A): 1.86 min, m/z (MH)$^+$=527.

Step B—tert-butyl 4'-{1-(6-iodopyrimidin-4-yl)-8-[(3-methylpyridin-2-yl)methyl]-2,4-dioxo-1,3,8-triazaspiro[4.5]dec-3-yl}biphenyl-4-carboxylate (8-B)

A mixture of tert-butyl 4'-{8-[(3-methylpyridin-2-yl)methyl]-2,4-dioxo-1,3,8-triazaspiro[4.5]dec-3-yl}biphenyl-4-carboxylate (Compound 8-A, 808 mg, 1.53 mmol), 4,6-diiodopyrimidine (1018 mg, 3.06 mmol), and cesium carbonate (1600 mg, 4.91 mmol) in 35 ml of Toluene was degassed with nitrogen for 10 min at 45° C. Then were added 1,10-phenanthroline (553 mg, 3.07 mmol) and copper(1) iodide (292 mg, 1.53 mmol) and degassed for 5 min. After, the reaction mixture was refluxed for 30 hr. Then it was filtered through celite and the filtrate was evaporated under reduced pressure. The residue was purified by column chromatography on silica gel, eluting with Hexane/ethyl acetate/NH3 (2M in MeOH) (100/100/8) to give Compound 8-B as a white solid. LCMS (Method A): 2.15 min, m/z (MH)$^+$=731.

Step C—tert-butyl 4'{-8-[(3-methylpyridin-2-yl)methyl]-2,4-dioxo-1-pyrimidin-4-yl-1,3,8-triazaspiro[4.5]dec-3-yl}biphenyl-4-carboxylate (8-C)

A reaction mixture of tert-butyl 4'-{1-(6-iodopyrimidin-4-yl)-8-[(3-methylpyridin-2-yl)methyl]-2,4-dioxo-1,3,8-triazaspiro[4.5]dec-3-yl}biphenyl-4-carboxylate (Compound 8-B, 700 mg, 0.96 mmol), and 320 mg of palladium (10% on carbon) in 10 ml of MeOH was hydrogenated at 50 psi H$_2$ for 3 hr. The mixture was filtered through celite and washed with CH$_2$Cl$_2$ (30 ml×4). The filtrate was evaporated under reduced pressure and the residue was purified by column chromatography on silica gel, eluting with Hexane/ethyl acetate/NH3 (2M in MeOH) (100/100/8) to give Compound 8-C as a white solid. LCMS (Method A): 2.02 min, m/z (MH)$^+$=605.

Step D—Titled Compound (8-1)

The reaction mixture of tert-butyl 4'-{8-[(3-methylpyridin-2-yl)methyl]-2,4-dioxo-1-pyrimidin-4-yl-1,3,8-triazaspiro[4.5]dec-3-yl}biphenyl-4-carboxylate (Compound 8-C, 470 mg, 0.78 mmol) in 3 ml of $CH_2Cl_2$ was treated with 6 ml of HCl in dioxane (4.0M) at rt. After 3.5 h, the resulting suspension was evaporated under reduced pressure. The residue was purified by mass-directed HPLC eluting 25-55% acetonitrile/0.1% NH4OH (aq) on an XBridge C18 5 um 50×100 mm column to give the Compound (8-1), as a white solid. $^1$HNMR (CD3OD): δ=2.42 (s, 3H), 2.45 (m, 2H), 3.80 (m, 2H), 3.80-3.94 (m, 2H), 4.04-4.10 (m, 2H), 4.76 (s, 2H), 7.37 (m, 1H), 7.64 (d, J=8.5 Hz, 2H), 7.74 (d, J=7.6 Hz, 1H), 7.79 (d, J=8.5 Hz, 2H), 7.86 (d, J=8.5 Hz, 2H), 8.14 (d, J=8.3 Hz, 2H), 8.46 (m, 1H), 8.54 (d, J=4.7 Hz, 1H), 8.74 (d, J=5.9 Hz, 1H), 9.06 (s, 1H); LCMS (Method A): 1.54 min, m/z (MH)$^+$=549.

Table 6 depicts compounds Examples 8-1 through 8-3 which were prepared as described for Example 8-1 and represented by formula VII.

TABLE 6

VII

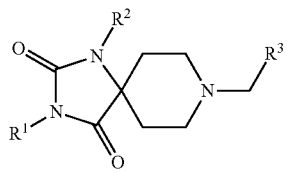

where: $R^1$ = 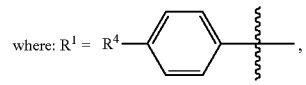, $R^3$ = 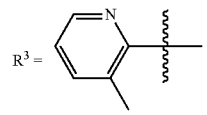 [SMILES: *c1ncccc1C]

| Ex. No. | IUPAC name | R4 | R2 | NMR and LCMS |
|---|---|---|---|---|
| 8-1 | 4'-{8-[(3-methylpyridin-2-yl)methyl]-2,4-dioxo-1-pyrimidin-4-yl-1,3,8-triazaspiro[4.5]dec-3-yl}biphenyl-4-carboxylic acid | 4-carboxyphenyl | pyrimidin-4-yl | $^1$HNMR(CD3OD): δ = 2.42 (s, 3H), 2.45(m, 2H), 3.80 (m, 2H), 3.80-3.94(m, 2H), 4.04-4.10(m, 2H), 4.76(s, 2H), 7.37(m, 1H), 7.64(d, J = 8.5 Hz, 2H), 7.74(d, J = 7.6 Hz, 1H), 7.79(d, J = 8.5 Hz, 2H), 7.86(d, J = 8.5 Hz, 2H), 8.14(d, J = 8.3 Hz, 2H), 8.46(m, 1H), 8.54(d, J = 4.7 Hz, 1H), 8.74 (d, J = 5.9 Hz, 1H), 9.06 (s, 1H); LCMS (Method A); 1.54 min, m/z (MH)+ = 549. |
| 8-2 | methyl 2-methyl-4'-{8-[(3-methylpyridin-2-yl)methyl]-2,4-dioxo-1-pyrimidin-4-yl-1,3,8-triazaspiro[4.5]dec-3-yl}biphenyl-4-carboxylate | 4-(methoxycarbonyl)-2-methylphenyl | pyrimidin-4-yl | $^1$HNMR(CDCl$_3$): δ = 1.82 (m, 2H), 2.38 (s, 3H), 2.53 (s, 3H), 2.96(m, 2H), 3.16(m, 2H), 3.64 (m, 2H), 3.89 (s, 2H), 3.98 (s, 3H), 7.16 (m, 1H), 7.34 (d, J = 7.9 Hz, 1H), 7.50(d, J = 8.6 Hz, 2H), 7.54(d, J = 8.6 Hz, 2H), 7.95(d, J = 7.8 Hz, 1H), 8.00(s, 1H), 8.31(d, J = 5.9 Hz, 1H), 8.46(d, J = 4.4 Hz, 1H), 8.69 (d, J = 5.9 Hz, 1H), 9.06 (s, 1H); LCMS (Method A); 1.83 min, m/z (MH)+ = 577. |
| 8-3 | 2-methyl-4'-{8-[(3-methylpyridin-2-yl)methyl]-2,4-dioxo-1-pyrimidin-4-yl-1,3,8-triazaspiro[4.5]dec-3-yl}biphenyl-4-carboxylic acid | 4-carboxy-2-methylphenyl | pyrimidin-4-yl | $^1$HNMR(CD$_3$OD): δ = 2.02(m, 2H), 2.34(s, 3H), 2.52(s, 3H), 3.10 (m, 2H), 3.61(m, 2H), 4.04 (m, 2H), 4.57(s, 2H), 7.29(m, 2H), 7.50 (d, J = 8.5 Hz, 2H), 7.56(d, J = 8.5 Hz, 2H), 7.68(d, J = 7.2 Hz, 1H), 7.86(d, J = 8.2 Hz, 1H), 7.93 (s, 1H), 8.36(d, J = 4.6 Hz, 1H), 8.38(d, J = 6.2 Hz, 1H), 8.64(d, J = 6.0 Hz, 1H), 8.98 (s, 1H); LCMS (Method A); 1.62 min, m/z (MH)+ = 563. |

Preparation of Intermediate D—4,6-diiodo-2-methylpyrimidine

A mixture of 4,6-dichloro-2-methylpyrimidine (2.43 g, 14.9 mmol), sodium iodide (3.13 g, 20.9 mmol), and 30 ml of hydriodic acid (57% in water) was stirred for 15 min. at 40° C. The mixture was filtered and the solid collected. To the solid was then added 5 ml of water and the pH adjusted to pH=7-8, with 2M NaOH and the mixture was evaporated under reduced pressure. To the resulting residue was added 15 ml of DCM, stirred thoroughly, and the resulting suspension filtered. The filtrate was evaporated under reduced pressure to give Intermediate D as a white solid. LCMS (Method A); 2.49 min, m/z (MH)+=255.

Example 9

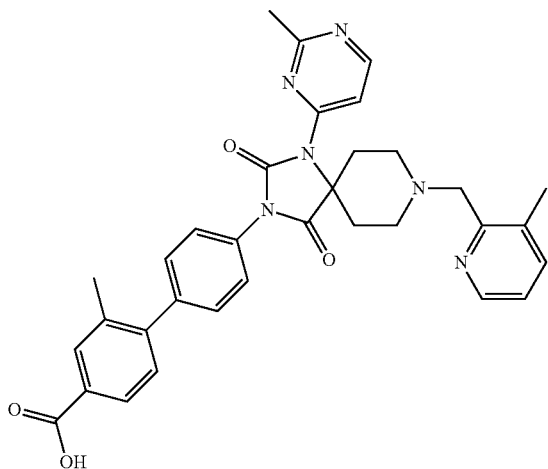

(9-1)

Step A—2-methyl-4'-{8-[(3-methylpyridin-2-yl)methyl]-2,4-dioxo-1,3,8-triazaspiro[4.5]dec-3-yl}biphenyl-4-carboxylic acid (Compound 9-A)

A reaction of 3-(4-bromophenyl)-8-[(3-methylpyridin-2-yl)methyl]-1,3,8-triazaspiro[4.5]decane-2,4-dione (Intermediate C, 964 mg, 2.25 mmol), 3-methyl-4-(4,4,5,5-tetramethyl-1,3,2-dioxaborolan-2-yl)benzoic acid (677 mg, 2.58 mmol), tetrakis(triphenylphosphine)palladium(0) (130 mg, 0.112 mmol), and 2N solution of potassium carbonate (2.25 ml, 4.50 mmol) in 18 ml of DMF was heated at 120° C. for 40 minute in a microwave. Then it was filtered to remove the solid and washed with MeOH. The filtrate was evaporated under reduced pressure to give the crude Compound 9-A, as a white solid. LCMS (Method A); 1.41 min, m/z (MH)+=485.

Step B—Benzyl 2-methyl-4'-{8-[(3-methylpyridin-2-yl) methyl]-2,4-dioxo-1,3,8-triazaspiro[4.5]dec-3-yl}biphenyl-4-carboxylate (Compound 9-B)

The reaction mixture of crude Compound 9-A, (2-methyl-4'-{8-[(3-methylpyridin-2-yl)methyl]-2,4-dioxo-1,3,8-triazaspiro[4.5]dec-3-yl}biphenyl-4-carboxylic acid, 1200 mg, 2.47 mmol), 1-(3-(dimethylaminopropyl)-3-ethylcarbodiimide hydrochloride (961 mg, 6.19 mmol), N,N-dimethylpyridin-4-amine (605 mg, 4.95 mmol), and phenylmethanol (803 mg, 7.43 mmol) in 30 ml of DCM was stirred for 12 h. The mixture was extracted with $CH_2Cl_2$ (2×20 mL) and the combined organic fractions were evaporated under reduced pressure. The residue was purified by column chromatography on silica gel, eluting with $CH_2Cl_2$/ethyl acetate/NH3 (2M in MeOH) (200/100/14) to give Compound 9-B. LCMS (Method A); 2.15 min, m/z (MH)+=731.

Step C—Benzyl 4'-{1-(6-iodo-2-methylpyrimidin-4-yl)-8-[(3-methylpyridin-2-yl)methyl]-2,4-dioxo-1,3,8-triazaspiro[4.5]dec-3-yl}-2-methylbiphenyl-4-carboxylate (Compound 9-C)

A mixture benzyl 2-methyl-4'-{8-[(3-methylpyridin-2-yl)methyl]-2,4-dioxo-1,3,8-triazaspiro[4.5]dec-3-yl}biphenyl-4-carboxylate (Compound 9-B, 490 mg, 0.85 mmol), 4,6-diiodo-2-methylpyrimidine (Intermediate D, 649 mg, 1.88 mmol), and cesium carbonate (833 mg, 2.56 mmol) in 35 ml of Toluene was degassed with nitrogen for 10 min at 45° C. 1,10-phenanthroline (307 mg, 1.7 mmol) and copper(1) iodide (162 mg, 0.85 mmol) was then added and the mixture degassed for 5 min. The reaction mixture was then refluxed for 30 h, filtered through celite and the filtrate evaporated under reduced pressure. The residue was purified by column chromatography on silica gel, eluting with Hexane/ethyl acetate/NH3 (2M in MeOH) (100/100/8) to give Compound 9-C as a white solid. LCMS (Method A); 2.30 min, m/z (MH)+=793.

Step D—2-methyl-4'-[8-[(3-methylpyridin-2-yl)methyl]-1-(2-methylpyrimidin-4-yl)-2,4-dioxo-1,3,8-triazaspiro[4.5]dec-3-yl]-biphenyl-4-carboxylic acid (9-1)

A mixture of benzyl 4'-{1-(6-iodo-2-methylpyrimidin-4-yl)-8-[(3-methylpyridin-2-yl)methyl]-2,4-dioxo-1,3,8-triazaspiro[4.5]dec-3-yl}-2-methylbiphenyl-4-carboxylate (Compound 9-C, 512 mg, 0.65 mmol), and 150 mg of palladium (10% on carbon) in 10 ml of MeOH was hydrogenated at 50 psi $H_2$ for 6 hr. The mixture was filtered through celite and washed with $CH_2Cl_2$ (30 ml×4). The organic layer was evaporated under reduced pressure and the residue was hydrogenated again at 50 psi $H_2$ in presence 160 mg of palladium (10% on carbon) for another 5 hr. The mixture was filtered through a celite and washed with MeOH and $CH_2Cl_2$ (30 ml×4). The combined organic layers was evaporated under reduced pressure and the residue was purified by mass-directed HPLC eluting 25-55% acetonitrile/0.1% NH4OH (aq) on an XBridge C18 5 um 50×100 mm column to give compound Example 9-1 as white solid. $^1$HNMR (CD$_3$OD): δ=1.94 (m, 2H), 2.32 (s, 3H), 2.57 (s, 3H), 2.68 (s, 3H), 2.95 (m, 2H), 3.20 (m, 2H), 3.59 (m, 2H), 3.95 (s, 2H), 7.27 (m, 2H), 7.48 (d, J=8.2 Hz, 2H), 7.53 (d, J=8.2 Hz, 2H), 7.66 (d, J=7.6 Hz, 1H), 7.84 (d, J=7.7 Hz, 1H), 8.17 (d, J=6.0 Hz, 1H), 8.31 (d, J=4.1 Hz, 1H), 8.53 (m, 1H); LCMS (Method A); 1.59 min, m/z (MH)+=577.

Table 7 depicts compounds Example 9-1 through 9-2, which were prepared as described for Example 9-1 and represented by formula VII.

TABLE 7

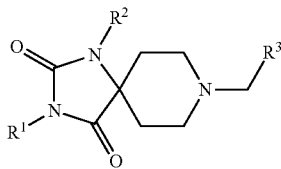

VII where: $R^1 = R^4$—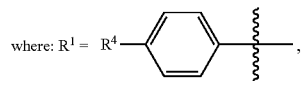, $R^3 =$ 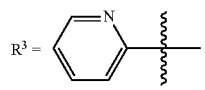

| Ex. No. | IUPAC name | R4 | R2 | NMR and LCMS |
|---|---|---|---|---|
| 9-1 | 2-methyl-4'-[8-[(3-methylpyridin-2-yl)methyl]-1-(2-methylpyrimidin-4-yl)-2,4-dioxo-1,3,8-triazaspiro[4.5]dec-3-yl]biphenyl-4-carboxylic acid | ![structure] | ![structure] | $^1$HNMR(CD$_3$OD): δ = 1.94(m, 2H), 2.32(s, 3H), 2.57(s, 3H), 2.68(s, 3H), 2.95 (m, 2H), 3.20(m, 2H), 3.59(m, 2H), 3.95(s, 2H), 7.27(m, 2H), 7.48(d, J = 8.2 Hz, 2H), 7.53(d, J = 8.2 Hz, 2H), 7.66(d, J = 7.6 Hz, 1H), 7.84(d, J = 7.7 Hz, 1H), 8.17(d, J = 6.0 Hz, 1H), 8.31(d, J = 4.1 Hz, 1H), 8.53(m, 1H); LCMS (Method A); 1.59 min, m/z (MH)+ = 577. |
| 9-2 | 2-methyl-4'-{8-[(3-methylpyridin-2-yl)methyl]-2,4-dioxo-1-pyridazin-3-yl-1,3,8-triazaspiro[4.5]dec-3-yl}biphenyl-4-carboxylic acid | ![structure] | ![structure] | $^1$HNMR(CDCl$_3$): δ = 2.19(m, 2H), 2.34(s, 3H), 2.47(s, 3H), 3.19(m, 2H), 3.34-3.44(m, 4H), 4.14(s, 2H), 7.28(m, 2H), 7.49 (d, J = 8.3 Hz, 2H), 7.58(d, J = 8.3 Hz, 2H), 7.66(d, J = 7.6 Hz, 1H), 7.77(m, 1H), 7.87(d, J = 7.7 Hz, 1H), 7.94(s, 1H), 8.36 (d, J = 4.7 Hz, 1H), 8.44(d, J = 8.0 Hz, 1H), 9.05(d, J = 4.5 Hz, 1H); LCMS (Method A); 1.59 min, m/z (MH)+ = 563. |

Preparation of Intermediate E—Tert-butyl 4-(5-bromopyridin-2-yl)benzoate (E-1)

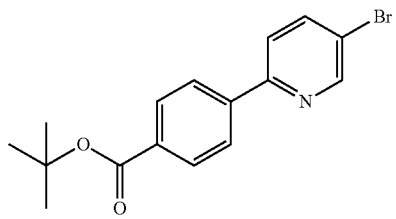

E-1

A mixture of 2,5-dibromopyridine (12.6 mmol), [4-(tert-butoxycarbonyl)phenyl]boronic acid (13.93 mmol), 2 N sodium carbonate (9.5 ml), methanol (20.0 ml), toluene (40.0 ml) and Tetrakis (0.63 mmol) was irradiated in the Advancer Biotage Microwave Reactor for 20 min at 120° C. The solvent was evaporated under reduced pressure and the resulting solid diluted with methylene chloride and water. The layers were separated and the aqueous layer washed with methylene chloride. The combined organic layers was dried (MgSO$_4$) and filtered through celite. Silica gel chromatography purification, eluting with 0 to 10% ethyl acetate/hexane afforded the title compound E-1. $^1$H NMR (CDCl3): δ=8.79 (d, J=2.2 Hz, 1H), 8.109 (d, J=12 Hz, 2H), 8.043 (d, J=11.9 Hz, 2H), 7.92 (d, J=10.9 Hz, 1H), 7.690 (d, J=8.4 Hz, 1H), 1.651 (s, 9H).

Preparation of Intermediate F—Benzyl 4-(5-bromopyridin-2-yl)-3-methylbenzoate (F-2)

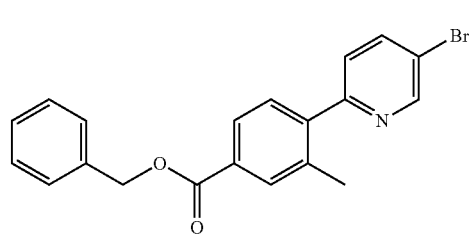

F-2

Step A—4-(5-bromopyridin-2-yl)-3-methylbenzoic acid (F-11

A mixture of 2,5-dibromopyridine (1.37 mmol), 4-(dihydroxyboryanyl)-3-methyl benzoic acid (1.37 mmol), 2 N sodium carbonate (0.82 ml), methanol (10.0 ml), toluene (20.0 ml) and Tetrakis (0.069 mmol) was irradiated in the Advancer Biotage Microwave Reactor for 20 min at 115° C.

The solvent was concentrated under reduced pressure and the resulting solid diluted with methylene chloride and water. The layers were separated and the aqueous layer washed with methylene chloride. The methylene chloride layer was discarded. The pH of the aqueous layer was adjusted to pH 7 with 2 N HCl and washed with EtOAc (×3). The combined organic layers was dried (MgSO$_4$) and filtered through celite. Trituration and filtration from diethyl ether/hexane afforded compound F-1. $^1$H NMR (CDCl3): δ=13.04 (b, 1H), 8.80 (d, J=2.3 Hz, 1H), 8.14-8.15 (dd, J=2.3, 8.4 Hz, 1H), 7.87 (s, 1H), 7.83 (d, J=8.0 Hz, 1H), 7.56 (d, J=8.4 Hz, 1H), 7.49 (d, J=7.9 Hz, 1H), 2.35 (s, 3H).

Step B—Benzyl 4-(5-bromopyridin-2-yl)-3-methylbenzoate (F-2)

The product from Step A, compound F-1 (2.05 mmol), 1-[(3-(Dimethylamino) propyl]-3-ethylcarbodiimide hydrochloride (4.52 mmol) and phenylmethanol (4.11 mmol) in methylene chloride (10 ml) was treated with N,N-dimethylpyridine-4-amine (2.05 mmol) at ambient temperature and the mixture stirred for 18 h. The mixture was diluted with methylene chloride and extracted with water. The organic layer was dried (MgSO$_4$) and concentrated under reduced pressure. Silica Gel purification eluting with 0 to 10% ethyl acetate/hexane afforded the title compound, F-2. LCMS (Method A): 2.32 min, m/z (MH)$^+$=283.9.

Preparation of Intermediate G—Benzyl 4-(5-bromopyridin-2-yl)-3-fluorobenzoate (G-2)

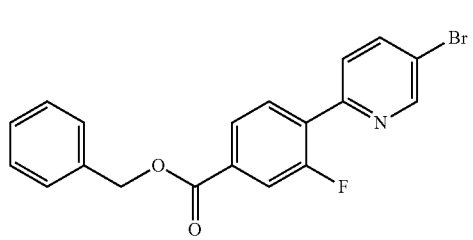

G-2

Step A—4-(5-bromopyridin-2-yl)-3-fluorobenzoic acid (Compound G-1)

A mixture of 5-bromo-2-iodopyridine (3.52 mmol), 4-(dihydroxyboryl)-3-fluoro-benzoic acid (3.52 mmol), potassium phosphate tribasic (7.04 mmol) and tri(dibenzylicene-acetone)dipalladium(0) chloroform adduct (0.18) was treated with triphenylphosphine (0.35 mmol) in a round bottom flask equipped with a reflux condenser. The flask was evacuated of oxygen with a strong flow of nitrogen, and then treated with methanol (10.0 ml) and toluene (30.0 ml). The mixture was then stirred at 80° C. for 16 h, cool to 60° C., diluted with methanol and filtered through celite. The filtrate was then concentrated to afford a crude solid consisting of compound G-1. LCMS (Method A): 1.82 min, m/z (MH)$^+$=297.9.

Step B—Benzyl 4-(5-bromopyridin-2-yl)-3-fluorobenzoate—Compound (G-2)

Following the procedure described for the preparation of Compound F-2 but with the crude product from Step A (Compound G-1) the title compound G-2 was afforded as a white crystalline solid. $^1$H NMR (CDCl$_3$): δ=8.83, (d, J=2.1 Hz, 1H), 8.12 (m, 1H), 7.99 (d, J=8.3 Hz, 1H), 7.93-7.59 (dd, J=2.3, 8.5 Hz, 1H), 7.88 (d, J=11.8 Hz, 1H), 7.38-7.50 (m, 5H), 5.42 (s, 2H). LCMS (Method A): 2.62 min, m/z (MH)$^+$=387.9.

Example 10

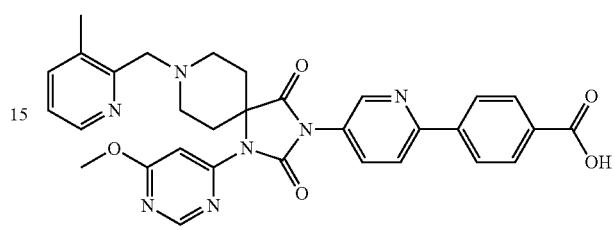

10-1

Step A—tert-butyl-3-{6-[4-(tert-butoxycarbonyl) phenyl]pyridin-3-yl}-2,4-dioxo-1,3,8-triazaspiro [4.5]decane-8-carboxylate (Compound 10-A)

Following the general procedure described for Compound 1-A but replacing 4-iodobiphenyl with Intermediate E (8.99 mmol), Compound 10-A was afforded as a White solid after silica gel chromatography, eluting with a 35:5:60 (EtOAc: MeOH:Hexane) solution. LCMS (Method A): 2.42 min, m/z (MH)$^+$=523.2.

Step B—tert-butyl-3-{6-[4-(tert-butoxycarbonyl) phenyl]pyridin-3-yl}-1-(6-methoxypyrimidin-4-yl)-2,4-dioxo-1,3,8-triazaspiro[4.5]decane-8-carboxylate (Compound 10-B)

Following the procedure described for Compound 1-B but substituting 1-A with 10-A, Compound 10-B was afforded after silica gel chromatography elating with 0 to 40% ethyl acetate/hexane. LCMS (Method A): 2.57 min, m/z (MH)$^+$=631.1.

Step C—4-{5-[1-(6-methoxypyrimidin-4-yl)-2,4-dioxo-1,3,8-triazaspiro[4.5]dec-3-yl]pyridin-2-yl}benzoic acid (Compound 10-C)

4M HCl in dioxane (4.76 ml, 19 mmol) was added to the product of Step B, 10-B, (0.9 mmol) via syringe. The resulting mixture was stirred at ambient temperature for 3 h and concentrated to afford Compound 10-C (tan solid) as an HCl salt. LCMS (Method A): 1.36 min, m/z (MH)$^+$=475.0.

Step D—4-(5-{1-(6-methoxypyrimidine-4-yl)-8-[(3-methylpyridin-2-yl)methyl]-2,4-dioxo-1,3,8-triazaspiro[4.5]dec-3-yl}pyridin-2-yl)benzoic acid, (10-1)

A suspension of Compound 10-C (0.9 mmol), triacetoxyborohydride (2.09 mmol) and 3-methylpyridine-2-carboxaldehyde (1.43 mmol) in dry methylene chloride was treated with acetic acid (2.85 mmol) and stirred at ambient temperature over night. The mixture was diluted with methylene chloride and water and the pH was adjusted to pH 7 with 1 N NaOH. The layers were separated and the aqueous layer washed (×2) with methylene chloride. The combined organic layers was dried (MgSO$_4$) and concentrated. Reverse Phase HPLC purification (Method C) afforded the title Compound 10-D (Example 10-1) as a salt of trifluoroacetic acid; $^1$H NMR (DMSO): δ=13.05-13.43 (b, 1H), 10.15-10.29 (b, 1H), 8.85 (s, 1H), 8.79 (s, 1H), 8.53 (s, 1H), 8.26-8.29 (m, 3H), 8.08-8.12 (m, 3H), 7.76 (d, J=7.7 Hz, 1H), 7.55 (s, 1H), 7.39-7.42 (m, 1H), 4.73 (s, 2H), 3.98 (s, 3H), 3.78 (m, 2H), 3.66 (m, 2H), 3.52-3.58 (m, 2H), 2.52 (m, 2H), 2.37 (s, 3H). LCMS (Method A): 1.58 min, m/z (MH)$^+$=580.1.

Table 8 discloses in addition to Example 10-1, Examples 10-2 through 10-4, which were prepared as described for Example 10-1 and represented by formula VII.

TABLE 8

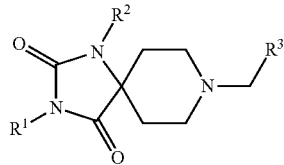

VII

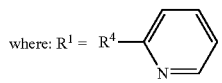

| Ex. No. | IUPAC name | R4 | R2 | R3 | NMR and LCMS |
|---|---|---|---|---|---|
| 10-1 | 4-(5-{1-(6-methoxypyrimidin-4-yl)-8-[(3-methylpyridin-2-yl)methyl]-2,4-dioxo-1,3,8-triazaspiro[4.5]dec-3-yl}-pyridin-2-yl)benzoic acid | 4-carboxyphenyl | 6-methoxypyrimidin-4-yl | 3-methylpyridin-2-yl | 1H NMR(DMSO): δ = 13.05-13.43 (b, 1H), 10.15-10.29 (b, 1H), 8.85 (s, 1H), 8.79 (s, 1H), 8.53 (s, 1H), 8.26-8.29 (m, 3H), 8.08-8.12 (m, 3H), 7.76 (d, J = 7.7 Hz, 1H), 7.55 (s, 1H), 7.39-7.42 (m, 1H), 4.73 (s, 2H), 3.98 (s, 3H), 3.78 (m, 2H), 3.66 (m, 2H), 3.52-3.58 (m, 2H), 2.52 (m, 2H), 2.37 (s, 3H). LCMS (Method A): 1.58 min, m/z (MH)$^+$ = 580.1. |
| 10-2 | 4-(5-{1-(4-methoxypyrimidin-2-yl)-8-[(3-methylpyridin-2-yl)methyl]-2,4-dioxo-1,3,8-triazaspiro[4.5]dec-3-yl}-pyridin-2-yl)benzoic acid | 4-carboxyphenyl | 4-methoxypyrimidin-2-yl | 3-methylpyridin-2-yl | 1HNMR(DMSO): δ = 12.58-13.37 (b, 1H), 9.96-10.63 (b, 1H), 9.11 (s, 1H) 8.86 (d, J = 2.2 Hz, 1H), 8.84 (d, J = 6.0 Hz, 1H), 8.54 (d, J = 4.3 Hz, 1H), 8.24-8.30 (m, 4H), 8.08-8.13 (m, 3H), 7.77 (d, J = 7.7 Hz, 1H), 7.39-7.42 (dd, J = 5.0, 7.5 Hz, 1H), 4.01 (s, 2H), 3.79 (m, 2H), 3.68 (m, 2H), 3.60 (m, 2H), 2.53 (m, 2H), 2.38 (s, 3H). LCMS (Method A): 1.46 min, m/z (MH)+ = 550.2. |
| 10-3 | 4-(5-{8-[(4-methoxypyridin-2-yl)methyl]-1-(6-methoxypyrimidin-4-yl)-2,4-dioxo-1,3,8-triazaspiro[4.5]dec-3-yl}-pyridin-2-yl)benzoic acid | 4-carboxyphenyl | 6-methoxypyrimidin-4-yl | 4-methoxypyridin-2-yl | LCMS (Method A): 1.60 min, m/z (MH)+ = 596.1. |
| 10-4 | 4-(5-{8-[(4-hydroxypyridin-2-yl)methyl]-1-(6-methoxypyrimidin-4-yl)-2,4-dioxo-1,3,8-triazaspiro[4.5]dec-3-yl}-pyridin-2-yl)benzoic acid | 4-carboxyphenyl | 6-methoxypyrimidin-4-yl | 4-hydroxypyridin-2-yl | 1HNMR(DMSO): δ = 12.12-13.04 (b, 1H) 8.82 (d, J = 2.2 Hz, 1H), 8.52 (d, J = 5.8 Hz, 1H), 8.32 (s, 1H), 8.24-8.27 (m, 3H), 8.07-8.08 (bd, J = 8.3 Hz, 3H), 7.27 (s, 1H), 7.10-7.12 (dd, 2.6, 5.8 Hz, 1H), 6.90 (s, 1H), 4.52 (s, 2H), 3.89 (s, 3H), 3.62 (m, 2H), 3.49 (m, 2H), 3.27-3.33 (dt, J = 3.6, 4.2 Hz, 2H), 2.45-2.49 (m, 1H). LCMS (Method A), 1.46 min, m/z (MH)$^+$ = 582.1. |

Example 11

4-(5-{1-(6-methoxypyrimidine-4-yl)-8-[(3-methylpyridin-2-yl)methyl]-2,4-dioxo-1,3,8-triazaspiro[4.5]dec-3-yl}pyridin-2-yl)-3-methybenzoic acid (11-1)

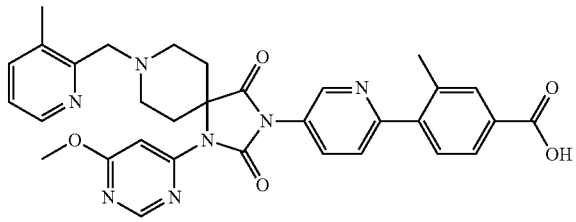

Example 11-1 was prepared according to the general procedure (Steps A-D) described for Example 10, whereby Intermediate E was replaced with Intermediate F in Step A. An additional step (Step E) required treatment of the product from Step D (Example 11), with 10% palladium on carbon in ethanol and hydrogenolysis on the parr shaker with 50 psi of hydrogen. Final purification was done according to Method C to afford the title compound (11-1) as a salt of trifluoroacetic acid; $^1$H NMR (DMSO): δ=12.85-13.21 (b, 1H), 10.10-10.41 (b, 1H), 8.84 (d, J=2.3 Hz, 1H), 8.79 (s, 1H), 8.54 (d, J=4.8 Hz, 1H), 8.08-8.10 (dd, 2.4, 8.3, Hz, 1H), 7.92 (s, 1H), 7.88 (d, J=7.9 Hz, 1H), 7.82 (d, J=8.4 Hz, 1H), 7.77 (d, J=7.7 Hz, 1H), 7.58 (d, J=7.9 Hz, 1H), 7.56 (s, 1H), 7.39-7.42 (dd, J=4.8, 7.5 Hz, 1H), 4.72 (s, 2H), 3.98 (s, 3H), 3.78 (m, 2H), 3.66 (m, 2H), 3.52-3.58 (m, 2H), 2.52 (m, 2H), 2.41 (s, 3H), 2.38 (s, 3H). LCMS (Method A): 1.61 min, m/z (MH)$^+$=594.1.

Table 9 discloses in addition to Example 11-1, Examples 11-2 through 11-3, which were prepared as described for Example 11-1 and represented by of formula VII.

TABLE 9

VII

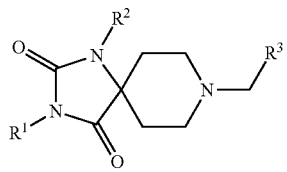

where: R$^1$ = 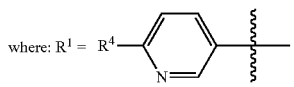

| Ex. No. | IUPAC name | R4 | R2 | R3 | NMR and LCMS |
|---|---|---|---|---|---|
| 11-1 | 4-(5-{1-(6-methoxypyrimidin-4-yl)-8-[(3-methylpyridin-2-yl)methyl]-2,4-dioxo-1,3,8-triazaspiro[4.5]dec-3-yl}-pyridin-2-yl)-3-methylbenzoic acid | 3-methyl-4-carboxyphenyl | 6-methoxypyrimidin-4-yl | 3-methylpyridin-2-yl | 1H NMR(DMSO): δ = 12.85-13.21 (b, 1H), 10.10-10.41 (b, 1H), 8.84 (d, J = 2.3 Hz, 1H), 8.79 (s, 1H), 8.54 (d, J = 4.8 Hz, 1H), 8.08-8.10 (dd, 2.4, 8.3, Hz, 1H), 7.92 (s, 1H), 7.88 (d, J = 7.9 Hz, 1H), 7.82 (d, J = 8.4 Hz, 1H), 7.77 (d, J = 7.7 Hz, 1H), 7.58 (d, J = 7.9 Hz, 1H), 7.56 (s, 1H), 7.39-7.42 (dd, J = 4.8, 7.5 Hz, 1H), 4.72 (s, 2H), 3.98 (s, 3H), 3.78 (m, 2H), 3.66 (m, 2H), 3.52-3.58 (m, 2H), 2.52 (m, 2H), 2.41 (s, 3H), 2.38 (s, 3H). LCMS (Method A): 1.61 min, m/z (MH)$^+$ = 594.1. |
| 11-2 | 4-(5-{1-(4-methoxypyrimidin-2-yl)-8-[(3-methylpyridin-2-yl)methyl]-2,4-dioxo-1,3,8-triazaspiro[4.5]dec-3-yl}-pyridin-2-yl)-3-methylbenzoic acid | 3-methyl-4-carboxyphenyl | 4-methoxypyrimidin-2-yl | 3-methylpyridin-2-yl | 1HNMR(DMSO): δ = 12.64-13.42 (b, 1H), 9.75-10.42 (b, 1H), 8.84 (d, J = 2.1 Hz, 1H), 8.60 (d, J = 5.9 Hz, 1H), 8.49 (d, J = 4.7 Hz, 1H), 8.08-8.10 (dd, J = 2.3,8.3 Hz, 1H), 7.91 (s, 1H), 7.87 (d, J = 8.0, 1H), 7.80, (d, J = 8.3 Hz, 1H), 7.74 (d, J = 7.7 Hz, 1H), 7.57 (d, J = 8.0 Hz, 1H), 7.37-7.39 (dd, J = 4.8, 7.4 Hz, 1H), 6.94 (d, J = 5.8 Hz, 1H), 4.68 (s, 2H), 4.01 (s, 3H), 3.76 (m, 2H), 3.64 (m, 2H), 3.19-3.24 (dt, J = 2.4, 11.3 Hz, 2H), 2.56 (m, 2H), 2.40 (s, 3H), 2.33 (s, 3H). LCMS (Method A), 1.54 min, m/z (MH)$^+$ = 594.1. |

TABLE 9-continued

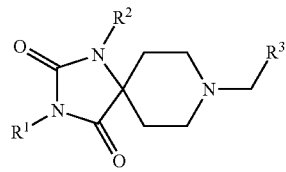

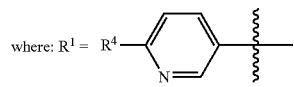

| Ex. No. | IUPAC name | R4 | R2 | R3 | NMR and LCMS |
|---|---|---|---|---|---|
| 11-3 | 3-methyl-4-(5-{8-[(3-methylpyridin-2-yl)methyl]-2,4-dioxo-1-(2,2,2-trifluoroethyl)-1,3,8-triazaspiro[4.5]dec-3-yl}-pyridin-2-yl) benzoic acid | | $F_3C$ | | LCMS (Method A), 1.55 min, m/z $(MH)^+ = 568.1$. |

Example 12

3-fluoro-4-(5-{1-(6-methoxypyrimidine-4-yl)-8-[(3-methylpyridin-2-yl)methyl]-2,4-dioxo-1,3,8-triazaspiro[4.5]dec-3-yl}pyridin-2-yl)-3-benzoic acid (12-1)

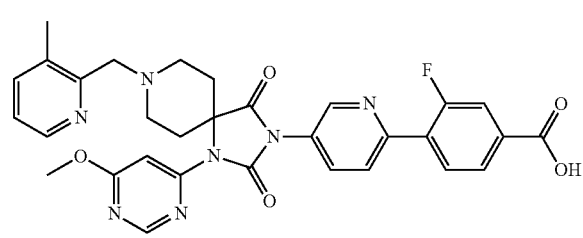

Example 12-1 was prepared according to the general procedure described for Example whereby Intermediate E was replaced with Intermediate G in Step A. An additional step (Step E) required treatment of the product from Step D (Example 12), with 10% palladium on carbon in ethanol and hydrogenolysis on the parr shaker with 50 psi of hydrogen. Final purification was done according to Method C to afford the title compound (12-1) as a salt of trifluoroacetic acid; $^1$H NMR (DMSO): δ=13.22-13.53 (b, 1H), 9.98-10.47 (b, 1H), 8.89 (d, J=2.3 Hz, 1H), 8.79 (s, 1H), 8.53 (d, J=4.5 Hz, 1H), 8.08-8.14 (m, 5H), 7.90-7.92 (dd, J=1.3, 8.1 Hz 1H), 7.82 (d, J=11.5 Hz, 1H), 7.75 (d, J=7.7 Hz, 1H), 7.53 (s, 1H), 7.38-7.41 (dd, J=4.8, 7.6 Hz, 1H), 4.72 (s, 2H), 3.98 (s, 3H), 3.78 (m, 2H), 3.66 (m, 2H), 3.55 (m, 2H), 2.52 (m, 2H), 2.36 (s, 3H). LCMS (Method A): 1.7 min, m/z $(MH)^+=598.2$.

Definition of Methods A-C for HPLC Analysis and Purification:

Method A

Conditions for LCMS: Mass Spectrometer: Micromass ZQ single quadrupole, Electrospray Positive Ionization, Full Scan mode (150-750 amu in 0.5 s); HPLC: Agilent 1100, Binary Pump; DAD UV detector: Hardware/software Waters/Micromass MassLynx 4.0; Column: Waters Xterra, 3.0 mm Width, 50 mm Length, 3.5 micron packing material; Runtime: 4.0 min; Flow Rate: 1.0 ml/min.; Mobile Phase A=Water+0.05% TFA, B=Acetonitrile+0.05% TFA; Gradient: Time/% A/% B: 0.00/90/10, 3.25/2/98, 3.75/2/98, 4.00/90/10.

Method B

Conditions for LCMS: Mass Spectrometer: Micromass ZQ single quadrupole, Electrospray Positive Ionization, Full Scan mode (150-750 amu in 0.5 s); HPLC: Agilent 1100, Binary Pump; DAD UV detector: Hardware/software Waters/Micromass MassLynx 4.0; Column: Waters Xterra, 3.0 nm Width, 50 mm Length, 3.5 micron packing material; Runtime: 5.5 min; Flow Rate: 1.0 ml/min.; Mobile Phase A=Water+0.05% TFA, B=Acetonitrile+0.05% TFA; Gradient: Time/% A/% B: 0.00/90/10, 3.75/2/98, 4.75/2/98, 4.76/90/10, 5.5/90/10.

Method C:

Preparative reverse phase liquid chromatography (RPHPLC) was performed using Waters MS Directed Purification System consisting of 2525 Binary Gradient Pump, 2767 Injector/Collector and 2996 PDA UV detector, mobile phase: gradient of water and acetonitrile (each cont. 0.1% TFA), column: Waters Sunfire (30×100 mm, 5 micron packing material).

Biological Assay

The exemplified compounds, 1-1 to 1-71, 2-1 to 2-8, 3-1 to 3-12, 4-1, 5-1, to 5-7, 6-1, and 7-1 of the present invention, have been found to inhibit the interaction between PHD2 and a HIF peptide and exhibit $IC_{50}$ values ranging between 0.1 nanomolar to 10 micromolar. Non-limiting examples of assays that may be useful to detect favorable activity are disclosed in the following publications: Oehme, F., et al., *Anal. Biochem.* 330:74-80 (2004); Hirsilä, M, et al., *J. Bio. Chem.* 278 (33): 30772-30780 (2005); Hyunju, C., et al., *Biochem. Biophys. Res. Comm.* 330 (2005) 275-280; and Hewitson, K. S., et al., *Methods in Enzymoloy*, (Oxygen Biology and Hypoxia); Elsevier Publisher (2007), pg. 25-42 (ISSN: 0076-6879).

The biological activity of the present compounds may be evaluated using assays described herein below:

Assay for HIF-PHD2 Catalytic Activity

To each well of a 96-well plate was added 1 μL of test compound in DMSO and 20 μL of assay buffer (50 mM Tris pH 7.4/0.01% Tween-20/0.1 mg/ml bovine serum albumin/10 μM ferrous sulfate/1 mM sodium ascorbate/20 μg/ml catalase) containing 0.15 μg/ml FLAG-tagged full length PHD2 expressed in and purified from baculovirus-infected Sf9 cells. After a min preincubation at room temperature, the enzymatic reactions were initiated by the addition of 4 μL of substrates (final concentrations of 0.2 μM 2-oxoglutarate and 0.5 μM HIF-1α peptide biotinyl-DLDLEMLAPYIPMDDDFQL). After 2 hr at room temperature, the reactions were terminated and signals were developed by the addition of a 25 μL quench/detection mix to a final concentration of 1 mM ortho-phenanthroline, 0.1 mM EDTA, 0.5 nM anti-(His)$_6$ LANCE reagent (Perkin-Elmer Life Sciences), 100 nM AF647-labeled streptavidin (Invitrogen), and 2 μg/ml (His)$_6$-VHL complex (S. Tan(2001) Protein Expr. Purif. 21, 224-234). The ratio of time resolved fluorescence signals at 665 and 620 nm was determined, and percent inhibition was calculated relative to an uninhibited control sample run in parallel.

Inhibition of the catalytic activity of HIF-PHD1 and HIF-PHD3 can be determined similarly.

The following three compounds, disclosed as Examples 31, 32, and 32-2 in PCT application WO 2008/030412 to Egbertson, M., et al., were tested for inhibition of the catalytic activity of HIF-PHD1, HIF-PHD2, and HIF-PHD3 using biological in vitro assays described above. All compounds tested inactive with IC$_{50}$ of greater than 10,000 nM against three isoforms of PHD.

| Compound No. | Compound Structure | IC$_{50}$ (nM) HIF-PHD-1 HIF-PHD-1 HIF-PHD-3 |
|---|---|---|
| Egbertson's Example 31 | | >10,000 nM |
| Egbertson's Example 32 | 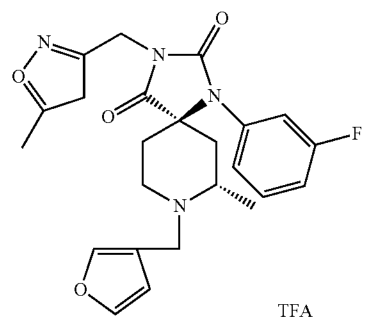 | >50000 nM |
| Egbertson's Example 32-2 | 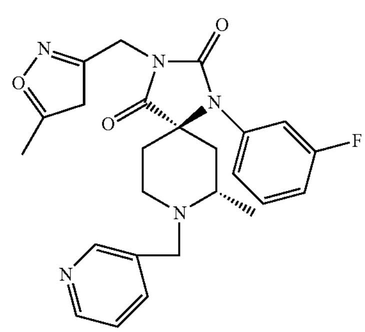 | >10,000 nM |

Table 5 depicts the HIF PHD2 binding activity expressed as IC$_{50}$ (nM), for the exemplified compounds, 1-1 to 1-71, 2-1 to 2-8, 3-1 to 3-12, 4-1, 5-1, to 5-7, 6-1, and 7-1 of the present invention.

TABLE 10

PHD2 Binding Activity

| Cmp. No. | Compound IUPAC name | IC$_{50}$ (nM) |
|---|---|---|
| 1-1 | 3-biphenyl-4-yl-1-(4-hydroxypyrimidin-2-yl)-8-[(3-methylpyridin-2-yl)methyl]-1,3,8-triazaspiro[4.5]decane-2,4-dione | + |
| 1-2 | 3-biphenyl-4-yl-8-[(3-methylpyridin-2-yl)methyl]-1-pyridin-2-yl-1,3,8-triazaspiro[4.5]decane-2,4-dione | + |
| 1-3 | 1-(4-hydroxypyrimidin-2-yl)-8-[(3-methylpyridin-2-yl)methyl]-3-phenyl-1,3,8-triazaspiro[4.5]decane-2,4-dione | +++ |

TABLE 10-continued

PHD2 Binding Activity

| Cmp. No. | Compound IUPAC name | IC$_{50}$ (nM) |
|---|---|---|
| 1-4 | 3-biphenyl-4-yl-8-[(3-methylpyridin-2-yl)methyl]-1-phenyl-1,3,8-triazaspiro[4.5]decane-2,4-dione | + |
| 1-5 | 2-{3-biphenyl-4-yl-8-[(3-methylpyridin-2-yl)methyl]-2,4-dioxo-1,3,8-triazaspiro[4.5]dec-1-yl}isonicotinic acid | + |
| 1-6 | 3-biphenyl-4-yl-1-(6-fluoropyridin-2-yl)-8-[(3-methylpyridin-2-yl)methyl]-1,3,8-triazaspiro[4.5]decane-2,4-dione | + |
| 1-7 | 6-{3-biphenyl-4-yl-8-[(3-methylpyridin-2-yl)methyl]-2,4-dioxo-1,3,8-triazaspiro[4.5]dec-1-yl}nicotinonitrile | + |
| 1-8 | 3-biphenyl-4-yl-8-[(3-methylpyridin-2-yl)methyl]-1-pyridin-4-yl-1,3,8-triazaspiro[4.5]decane-2,4-dione | ++ |
| 1-9 | 3-biphenyl-4-yl-1-(6-hydroxypyridazin-3-yl)-8-[(3-methylpyridin-2-yl)methyl]-1,3,8-triazaspiro[4.5]decane-2,4-dione | + |
| 1-10 | 3-biphenyl-4-yl-1-(5-hydroxypyrimidin-2-yl)-8-[(3-methylpyridin-2-yl)methyl]-1,3,8-triazaspiro[4.5]decane-2,4-dione | + |
| 1-11 | 3-biphenyl-4-yl-1-(6-methoxypyridin-2-yl)-8-[(3-methylpyridin-2-yl)methyl]-1,3,8-triazaspiro[4.5]decane-2,4-dione | + |
| 1-12 | 3-biphenyl-4-yl-1-(6-hydroxypyridin-2-yl)-8-[(3-methylpyridin-2-yl)methyl]-1,3,8-triazaspiro[4.5]decane-2,4-dione | + |
| 1-13 | methyl 6-{3-biphenyl-4-yl-8-[(3-methylpyridin-2-yl)methyl]-2,4-dioxo-1,3,8-triazaspiro[4.5]dec-1-yl}pyridine-2-carboxylate | + |
| 1-14 | 6-{3-biphenyl-4-yl-8-[(3-methylpyridin-2-yl)methyl]-2,4-dioxo-1,3,8-triazaspiro[4.5]dec-1-yl}pyridine-2-carboxylic acid | + |
| 1-15 | 1-(4-methoxypyrimidin-2-yl)-8-[(3-methylpyridin-2-yl)methyl]-3-[4-(1H-tetrazol-5-yl)phenyl]-1,3,8-triazaspiro[4.5]decane-2,4-dione | ++ |
| 1-16 | 1-(4-hydroxypyrimidin-2-yl)-8-[(3-methylpyridin-2-yl)methyl]-3-[4-(1H-tetrazol-5-yl)phenyl]-1,3,8-triazaspiro[4.5]decane-2,4-dione | +++ |
| 1-17 | 4-{1-(4-hydroxypyrimidin-2-yl)-8-[(3-methylpyridin-2-yl)methyl]-2,4-dioxo-1,3,8-triazaspiro[4.5]dec-3-yl}benzoic acid | +++ |
| 1-18 | 3-biphenyl-4-yl-8-[(3-methylpyridin-2-yl)methyl]-1-pyridin-3-yl-1,3,8-triazaspiro[4.5]decane-2,4-dione | + |
| 1-19 | tert-butyl (2-{[3-biphenyl-4-yl-1-(4-methoxypyrimidin-2-yl)-2,4-dioxo-1,3,8-triazaspiro[4,5]dec-8-yl]methyl}-1H-imidazol-1-yl)acetate | +++ |
| 1-20 | tert-butyl (2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)acetate | + |
| 1-21 | (2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)acetic acid | + |
| 1-22 | 3-(2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)propanoic acid | + |
| 1-23 | (2-{[3-biphenyl-4-yl-1-(4-hydroxypyrimidin-2-yl)-2,4-dioxo-1,3,8-triazaspiro[4.5]dec-8-yl]methyl}-1H-imidazol-1-yl)acetic acid | + |
| 1-24 | 3-(2-{[3-biphenyl-4-yl-1-(4-hydroxypyrimidin-2-yl)-2,4-dioxo-1,3,8-triazaspiro[4.5]dec-8-yl]methyl}-1H-imidazol-1-yl)propanoic acid | + |
| 1-25 | 4-{1-(4-methoxypyrimidin-2-yl)-8-[(3-methylpyridin-2-yl)methyl]-2,4-dioxo-1,3,8-triazaspiro[4.5]dec-3-yl}benzonitrile | +++ |
| 1-26 | ethyl 4-{1-(4-methoxypyrimidin-2-yl)-8-[(3-methylpyridin-2-yl)methyl]-2,4-dioxo-1,3,8-triazaspiro[4.5]dec-3-yl}benzoate | + |
| 1-27 | 3-biphenyl-4-yl-8-[(3-methylpyridin-2-yl)methyl]-1-(2-thienyl)-1,3,8-triazaspiro[4.5]decane-2,4-dione | + |
| 1-28 | 3-biphenyl-4-yl-8-[(3-bromopyridin-2-yl)methyl]-1-(4-methoxypyrimidin-2-yl)-1,3,8-triazaspiro[4.5]decane-2,4-dione | ++ |
| 1-29 | 3-biphenyl-4-yl-1-(4-methoxypyrimidin-2-yl)-8-[(3-methylpyridin-2-yl)methyl]-1,3,8-triazaspiro[4.5]decane-2,4-dione | + |
| 1-30 | 1-(4-methoxypyrimidin-2-yl)-8-[(3-methylpyridin-2-yl)methyl]-3-phenyl-1,3,8-triazaspiro[4.5]decane-2,4-dione | +++ |
| 1-31 | 3-biphenyl-4-yl-8-[(3-bromopyridin-2-yl)methyl]-1-(4-hydroxypyrimidin-2-yl)-1,3,8-triazaspiro[4.5]decane-2,4-dione | +++ |
| 1-32 | 4-[8-[(3-bromopyridin-2-yl)methyl]-1-(4-hydroxypyrimidin-2-yl)-2,4-dioxo-1,3,8-triazaspiro[4.5]dec-3-yl]-N-phenylbenzamide | +++ |
| 1-33 | 3-biphenyl-4-yl-1-(4-hydroxypyrimidin-2-yl)-8-[(3-methylpyridin-2-yl)methyl]-1,3,8-triazaspiro[4.5]decane-2,4-dione | + |
| 1-34 | 4-[8-[(3-bromopyridin-2-yl)methyl]-1-(4-hydroxypyrimidin-2-yl)-2,4-dioxo-1,3,8-triazaspiro[4.5]dec-3-yl]-N-cyclopropylbenzamide | +++ |
| 1-35 | 3-biphenyl-4-yl-8-[(3-bromopyridin-2-yl)methyl]-1-pyrimidin-2-yl-1,3,8-triazaspiro[4.5]decane-2,4-dione | + |
| 1-36 | 3-biphenyl-4-yl-8-[(3-bromopyridin-2-yl)methyl]-1-(4-hydroxypyridin-2-yl)-1,3,8-triazaspiro[4.5]decane-2,4-dione | + |
| 1-37 | tert-butyl 2-{[3-biphenyl-4-yl-1-(4-methoxypyrimidin-2-yl)-2,4-dioxo-1,3,8-triazaspiro[4.5]dec-8-yl]methyl}nicotinate | ++ |
| 1-38 | 2-{[3-biphenyl-4-yl-1-(4-hydroxypyrimidin-2-yl)-2,4-dioxo-1,3,8-triazaspiro[4.5]dec-8-yl]methyl}nicotinic acid | ++ |
| 1.39 | 3-biphenyl-4-yl-1-(4-methoxypyrimidin-2-yl)-8-(1H-tetrazol-5-ylmethyl)-1,3,8-triazaspiro[4.5]decane-2,4-dione | +++ |
| 1-40 | 2-{[3-biphenyl-4-yl-1-(4-methoxypyrimidin-2-yl)-2,4-dioxo-1,3,8-triazaspiro[4.5]dec-8-yl]methyl}nicotinonitrile | +++ |

TABLE 10-continued

PHD2 Binding Activity

| Cmp. No. | Compound IUPAC name | IC$_{50}$ (nM) |
|---|---|---|
| 1-41 | 3-biphenyl-4-yl-1-(4-methoxypyrimidin-2-yl)-8-{[3-(1H-tetrazol-5-yl)pyridin-2-yl]methyl}-1,3,8-triazaspiro[4.5]decane-2,4-dione | +++ |
| 1-42 | 3-biphenyl-4-yl-1-(2-hydroxypyrimidin-4-yl)-8-[(3-methylpyridin-2-yl)methyl]-1,3,8-triazaspiro[4.5]decane-2,4-dione | + |
| 1-43 | 3-biphenyl-4-yl-1-(3-hydroxypyridin-2-yl)-8-[(3-methylpyridin-2-yl)methyl]-1,3,8-triazaspiro[4.5]decane-2,4-dione | ++ |
| 1-44 | 4'-{1-(6-hydroxypyrimidin-4-yl)-8-[(3-methylpyridin-2-yl)methyl]-2,4-dioxo-1,3,8-triazaspiro[4.5]dec-3-yl}biphenyl-4-carboxylic acid | ++ |
| 1-45 | 3-biphenyl-4-yl-1-(5-hydroxypyrazin-2-yl)-8-[(3-methylpyridin-2-yl)methyl]-1,3,8-triazaspiro[4.5]decane-2,4-dione | ++ |
| 1-46 | Butyl 4-{[3-biphenyl-4-yl-1-(4-hydroxypyrimidin-2-yl)-2,4-dioxo-1,3,8-triazaspiro[4.5]dec-8-yl]methyl}-1-H-imidazole-5-carboxylate | ++ |
| 1-47 | Butyl 4-{[3-biphenyl-4-yl-1-(4-methoxypyrimidin-2-yl)-2,4-dioxo-1,3,8-triazaspiro[4.5]dec-8-yl]methyl}-1-H-imidazole-5-carboxylate | ++ |
| 1-48 | Butyl 4-{[3-biphenyl-4-yl-1-(6-methoxypyrimidin-4-yl)-2,4-dioxo-1,3,8-triazaspiro[4.5]dec-8-yl]methyl}-1-H-imidazole-5-carboxylate | + |
| 1-49 | 3-biphenyl-4-yl-1-(4-methoxypyrimidin-2-yl)-8-[(5-methyl-1-H-imidazol-4-yl)methyl]-1,3,8-triazaspiro[4.5]decane-2,4-dione | + |
| 1-50 | 4-{[3-biphenyl-4-yl-1-(4-methoxypyrimidin-2-yl)-2,4-dioxo-1,3,8-triazaspiro[4.5]dec-8-yl]methyl}-1-H-imidazole-5-carboxylic acid | ++ |
| 1-51 | 4-[(3-biphenyl-4-yl-2,4-dioxo-1,3,8-triazaspiro[4.5]dec-8-yl)methyl]-1-H-imidazole-5-carboxylic acid | + |
| 1-52 | 4-{[3-biphenyl-4-yl-1-(6-hydroxypyrimidin-4-yl)-2,4-dioxo-1,3,8-triazaspiro[4.5]dec-8-yl]methyl}-1-H-imidazole-5-carboxylic acid | + |
| 1-53 | 3-biphenyl-4-yl-1-(6-hydroxypyrimidin-4-yl)-8-[(5-methyl-1-H-imidazol-4-yl)methyl]-1,3,8-triazaspiro[4.5]decane-2,4-dione | + |
| 1-54 | 2-{[3-biphenyl-4-yl-1-(6-hydroxypyrimidin-4-yl)-2,4-dioxo-1,3,8-triazaspiro[4.5]dec-8-yl]methyl}nicotinic acid | +++ |
| 1-55 | 3-biphenyl-4-yl-1-(4,6-dihydroxypyrimidin-2-yl)-8-[(3-methylpyridin-2-yl)methyl]-1,3,8-triazaspiro[4.5]decane-2,4-dione | + |
| 1-56 | 3-biphenyl-4-yl-1-(4-hydroxy-6-methoxypyrimidin-2-yl)-8-[(3-methylpyridin-2-yl)methyl]-1,3,8-triazaspiro[4.5]decane-2,4-dione | + |
| 1-57 | 3-biphenyl-4-yl-1-(4,6-dimethoxypyrimidin-2-yl)-8-[(3-methylpyridin-2-yl)methyl]-1,3,8-triazaspiro[4.5]decane-2,4-dione | + |
| 1-58 | 3-biphenyl-4-yl-1-(2-hydroxypyridin-4-yl)-8-[(3-methylpyridin-2-yl)methyl]-1,3,8-triazaspiro[4.5]decane-2,4-dione | + |
| 1-59 | 2-{3-biphenyl-4-yl-8-[(3-methylpyridin-2-yl)methyl]-2,4-dioxo-1,3,8-triazaspiro[4.5]dec-1-yl}pyrimidine-4-carboxylic acid | + |
| 1-60 | 6-{3-biphenyl-4-yl-8-[(3-methylpyridin-2-yl)methyl]-2,4-dioxo-1,3,8-triazaspiro[4.5]dec-1-yl}nicotinic acid | + |
| 1-61 | Methyl 4'-{8-[(3-methylpyridin-2-yl)methyl]-2,4-dioxo-1-pyrimidin-2-yl-1,3,8-triazaspiro[4.5]dec-3-yl}biphenyl-4-carboxylate | + |
| 1-62 | Methyl 4-[(3-biphenyl-4-yl-2,4-dioxo-1-pyrimidin-2-yl-1,3,8-triazaspiro[4.5]dec-8-yl)methyl]-1-H-imidazole-5-carboxylate | |
| 1-63 | 4'-{8-[(3-methylpyridin-2-yl)methyl]-2,4-dioxo-1-pyrimidin-2-yl-1,3,8-triazaspiro[4.5]dec-3-yl}biphenyl-4-carboxylic acid | + |
| 1-64 | 4-[(3-biphenyl-4-yl-2,4-dioxo-1-pyrimidin-2-yl-1,3,8-triazaspiro[4.5]dec-8-yl)methyl]-1-H-imidazole-5-carboxylic acid | + |
| 1-65 | 5-(4-{8-[(3-carboxypyridin-2-yl)methyl]-2,4-dioxo-1-pyrimidin-2-yl-1,3,8-triazaspiro[4.5]dec-3-yl}phenyl)pyridine-2-carboxylic acid | + |
| 1-66 | 4'-{8-[(3-methylpyridin-2-yl)methyl]-2,4-dioxo-1-pyrimidin-2-yl-1,3,8-triazaspiro[4.5]dec-3-yl}biphenyl-3-carboxylic acid | + |
| 1-67 | (4'-{8-[(3-methylpyridin-2-yl)methyl]-2,4-dioxo-1-pyrimidin-2-yl-1,3,8-triazaspiro[4.5]dec-3-yl}biphenyl-4-yl)acetic acid | ++ |
| 1-68 | 3-biphenyl-4-yl-8-[(3-methylpyridin-2-yl)methyl]-1-pyrimidin-4-yl-1,3,8-triazaspiro[4.5]decane-2,4-dione | + |
| 1-69 | 2-(4-{8-[(3-methylpyridin-2-yl)methyl]-2,4-dioxo-1-pyrimidin-2-yl-1,3,8-triazaspiro[4.5]dec-3-yl}phenyl)cyclopropanecarboxylic acid | + |
| 1-70 | 8-[(3-methylpyridin-2-yl)methyl]-1-(6-methoxypyrimidin-4-yl)-3-(4'-propionylbiphenyl-4-yl)-1,3,8-triazaspiro[4.5]decane-2,4-dione | + |
| 1-71 | 1-(6-hydroxypyrimidin-4-yl)-8-[(3-methylpyridin-2-yl)methyl]-3-(4'-propionylbiphenyl-4-yl)-1,3,8-triazaspiro[4.5]decane-2,4-dione | + |
| 2-1 | 3-biphenyl-4-yl-1-methyl-8-[(3-methylpyridin-2-yl)methyl]-1,3,8-triazaspiro[4.5]decane-2,4-dione | + |
| 2-2 | tert-butyl (3-biphenyl-4-yl-2,4-dioxo-1-pyrazin-2-yl-1,3,8-triazaspiro[4.5]dec-8-yl)acetate | +++ |
| 2-3 | (3-biphenyl-4-yl-2,4-dioxo-1-pyrazin-2-yl-1,3,8-triazaspiro[4.5]dec-8-yl)acetic acid | + |
| 2-4 | (3-biphenyl-4-yl-2,4-dioxo-1-pyrimidin-5-yl-1,3,8-triazaspiro[4.5]dec-8-yl)acetic acid | ++ |
| 2-5 | (3-biphenyl-4-yl-2,4-dioxo-1-pyrimidin-2-yl-1,3,8-triazaspiro[4.5]dec-8-yl)acetic acid | + |
| 2-6 | [3-biphenyl-4-yl-1-(4-methoxypyrimidin-2-yl)-2,4-dioxo-1,3,8-triazaspiro[4.5]dec-8-yl]acetic acid | + |

TABLE 10-continued

PHD2 Binding Activity

| Cmp. No. | Compound IUPAC name | IC$_{50}$ (nM) |
|---|---|---|
| 2-7 | 2,2'-(3-biphenyl-4-yl-2,4-dioxo-1,3,8-triazaspiro[4.5]decane-1,8-diyl)diacetic acid | + |
| 2-8 | [3-biphenyl-4-yl-1-(2-ethoxy-2-oxoethyl)-2,4-dioxo-1,3,8-triazaspiro[4.5]dec-8-yl]acetic acid | ++ |
| 3-1 | 3-biphenyl-4-yl-8-[(3-methylpyridin-2-yl)methyl]-1,3,8-triazaspiro[4.5]decane-2,4-dione | + |
| 4-1 | (3-biphenyl-4-yl-2,4-dioxo-1,3,8-triazaspiro[4.5]dec-8-yl)acetic acid | +++ |
| 3-2 | ethyl 3-biphenyl-4-yl-1-(4-methoxypyrimidin-2-yl)-8-[(3-methylpyridin-2-yl)methyl]-2,4-dioxo-1,3,8-triazaspiro[4.5]decane-6-carboxylate | + |
| 3-3 | ethyl 3-biphenyl-4-yl-1-(4-hydroxypyrimidin-2-yl)-8-[(3-methylpyridin-2-yl)methyl]-2,4-dioxo-1,3,8-triazaspiro[4.5]decane-6-carboxylate | + |
| 3-4 | 3-biphenyl-4-yl-1-(4-hydroxypyrimidin-2-yl)-8-[(3-methylpyridin-2-yl)methyl]-2,4-dioxo-1,3,8-triazaspiro[4.5]decane-6-carboxylic acid | + |
| 3-5 | 3-biphenyl-4-yl-8-[(3-methylpyridin-2-yl)methyl]-2,4-dioxo-1,3,8-triazaspiro[4.5]decane-6-carboxylic acid | + |
| 3-6 | Ethyl 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylate | + |
| 3-7 | 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid | + |
| 3-8 | 3-biphenyl-4-yl-8-[(3-methylpyridin-2-yl)methyl]-2,4-dioxo-1-pyrimidin-2-yl-1,3,8-triazaspiro[4.5]decane-6-carboxylic acid | + |
| 3-9 | Ethyl 3-biphenyl-4-yl-1-(6-methoxypyrimidin-4-yl)-8-[(3-methylpyridin-2-yl)methyl]-2,4-dioxo-1,3,8-triazaspiro[4.5]decane-6-carboxylate | + |
| 3-10 | Ethyl 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylate | + |
| 3-11 | 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid | + |
| 3-12 | 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid | + |
| 5-1 | ethyl [({3-biphenyl-4-yl-8-[(3-methylpyridin-2-yl)methyl]-2,4-dioxo-1,3,8-triazaspiro[4.5]dec-6-yl}carbonyl)amino]acetate | + |
| 5-2 | tert-butyl [({3-biphenyl-4-yl-8-[(3-methylpyridin-2-yl)methyl]-2,4-dioxo-1,3,8-triazaspiro[4.5]dec-6-yl}carbonyl)amino]acetate | N/A |
| 6-1 | [({3-biphenyl-4-yl-8-[(3-methylpyridin-2-yl)methyl]-2,4-dioxo-1,3,8-triazaspiro[4.5]dec-6-yl}carbonyl)amino]acetic acid | + |
| 5-3 | 2-[({3-biphenyl-4-yl-8-[(3-methylpyridin-2-yl)methyl]-2,4-dioxo-1,3,8-triazaspiro[4.5]dec-1-yl}carbonyl)amino]-2-methylpropanoic acid | + |
| 5-4 | (2R)-2-[({3-biphenyl-4-yl-8-[(3-methylpyridin-2-yl)methyl]-2,4-dioxo-1,3,8-triazaspiro[4.5]dec-1-yl}carbonyl)amino]propanoic acid | + |
| 5-5 | (2S)-2-[({3-biphenyl-4-yl-8-[(3-methylpyridin-2-yl)methyl]-2,4-dioxo-1,3,8-triazaspiro[4.5]dec-1-yl}carbonyl)amino]propanoic acid | + |
| 5-6 | N-({3-biphenyl-4-yl-8-[(3-methylpyridin-2-yl)methyl]-2,4-dioxo-1,3,8-triazaspiro[4.5]dec-1-yl}carbonyl)-L-serine | + |
| 5-7 | 4-{3-biphenyl-4-yl-8-[(3-methylpyridin-2-yl)methyl]-2,4-dioxo-1,3,8-triazaspiro[4.5]dec-1-yl}-4-oxobutanoic acid | + |
| 7-1 | 4'-{1-(6-methoxypyrimidin-4-yl)-8-[(3-methylpyridin-2-yl)methyl]-2,4-dioxo-1,3,8-triazaspiro[4.5]dec-3-yl}biphenyl-4-carboxylic acid | + |
| 7-2 | 4'-{1-(6-methoxypyrimidin-4-yl)-8-[(3-methylpyridin-2-yl)methyl]-2,4-dioxo-1,3,8-triazaspiro[4.5]dec-3-yl}-2-methybiphenyl-4-carboxylic acid | + |
| 7-3 | 4'-{1-(6-methoxypyrimidin-4-yl)-8-[(3-methylpyridin-2-yl)methyl]-2,4-dioxo-1,3,8-triazaspiro[4.5]dec-3-yl}-3-methylbiphenyl-4-carboxylic acid | + |
| 7-4 | 2-fluoro-4'-{1-(6-methoxypyrimidin-4-yl)-8-[(3-methylpyridin-2-yl)methyl]-2,4-dioxo-1,3,8-triazaspiro[4.5]dec-3-yl}biphenyl-4-carboxylic acid | + |
| 7-5 | 2-methyl-4'-{8-[(3-methylpyridin-2-yl)methyl]-2,4-dioxo-1-pyrazin-2-yl-1,3,8-triazaspiro[4.5]dec-3-yl}biphenyl-4-carboxylic acid | + |
| 7-6 | 2-methyl-4'-{1-(6-methylpyrazin-2-yl)-8-[(3-methylpyridin-2-yl)methyl]-2,4-dioxo-1,3,8-triazaspiro[4.5]dec-3-yl}biphenyl-4-carboxylic acid | + |
| 7-7 | 4'-{1-(6-methylpyrazin-2-yl)-8-[(3-methylpyridin-2-yl)methyl]-2,4-dioxo-1,3,8-triazaspiro[4.5]dec-3-yl}biphenyl-4-carboxylic acid | + |
| 7-8 | 2-methyl-4'-[8-[(3-methylpyridin-2-yl)methyl]-1-(6-methylpyrimidin-4-yl)-2,4-dioxo-1,3,8-triazaspiro[4.5]dec-3-yl]biphenyl-4-carboxylic acid | + |
| 7-9 | 4'-[8-[(3-methylpyridin-2-yl)methyl]-1-(6-methylpyrimidin-4-yl)-2,4-dioxo-1,3,8-triazaspiro[4.5]dec-3-yl]biphenyl-4-carboxylic acid | + |
| 7-10 | 2-methyl-4'-{8-[(3-methylpyridin-2-yl)methyl]-2,4-dioxo-1-[6-(trifluoromethyl)pyrimidin-4-yl]-1,3,8-triazaspiro[4.5]dec-3-yl}biphenyl-4-carboxylic acid | + |
| 7-11 | 1-(6-methoxypyrimidin-4-yl)-8-[(3-methylpyridin-2-yl) methyl]-3-[4'-(1 H-pyrazol-5-yl) biphenyl-4-yl]-1,3,8-triazaspiro[4.5] decane-2,4-dione | + |
| 7-12 | 1-(6-hydroxypyrimidin-4-yl)-8-[(3-methylpyridin-2-yl) methyl]-3-[4'-(1 H-pyrazol-5-yl) biphenyl-4-yl]-1,3,8-triazaspiro[4.5] decane-2,4-dione | + |
| 7-13 | 1-(6-methoxypyrimidin-4-yl)-8-[(3-methylpyridin-2-yl) methyl]-3-[4'-(5-oxopyrazolidin-3-yl) biphenyl-4-yl]-1,3,8-triazaspiro[4.5] decane-2,4-dione | + |
| 7-14 | 1-(6-hydroxypyrimidin-4-yl)-8-[(3-methylpyridin-2-yl) methyl]-3-[4'-(1 morpholin-4-yl) biphenyl-4-yl]-1,3,8-triazaspiro[4.5] decane-2,4-dione | + |

TABLE 10-continued

PHD2 Binding Activity

| Cmp. No. | Compound IUPAC name | $IC_{50}$ (nM) |
|---|---|---|
| 7-15 | 4-(6-{3-(4-bromophenyl)-8-[(3-methylpyridin-2-yl)methyl]-2,4-dioxo-1,3,8-triazaspiro[4.5]dec-1-yl}pyrimidin-4-yl)benzoic acid | + |
| 8-1 | 4'-{8-[(3-methylpyridin-2-yl)methyl]-2,4-dioxo-1-pyrimidin-4-yl-1,3,8-triazaspiro[4.5]dec-3-yl}biphenyl-4-carboxylic acid | + |
| 8-2 | methyl 2-methyl-4'-{8-[(3-methylpyridin-2-yl)methyl]-2,4-dioxo-1-pyrimidin-4-yl-1,3,8-triazaspiro[4.5]dec-3-yl}biphenyl-4-carboxylate | + |
| 8-3 | 2-methyl-4'-{8-[(3-methylpyridin-2-yl)methyl]-2,4-dioxo-1-pyrimidin-4-yl-1,3,8-triazaspiro[4.5]dec-3-yl}biphenyl-4-carboxylic acid | + |
| 9-1 | 2-methyl-4'-[8-[(3-methylpyridin-2-yl)methyl]-1-(2-methylpyrimidin-4-yl)-2,4-dioxo-1,3,8-triazaspiro[4.5]dec-3-yl]biphenyl-4-carboxylic acid | + |
| 9-2 | 2-methyl-4'-{8-[(3-methylpyridin-2-yl)methyl]-2,4-dioxo-1-pyridazin-3-yl-1,3,8-triazaspiro[4.5]dec-3-yl}biphenyl-4-carboxylic acid | + |
| 10-1 | 4-(5-{1-(6-methoxypyrimidin-4-yl)-8-[(3-methylpyridin-2-yl) methyl]-2,4-dioxo-1,3,8-triazaspiro[4.5]dec-3-yl}-pyridin-2-yl) benzoic acid | + |
| 10-2 | 4-(5-{1-(4-methoxypyrimidin-2-yl)-8-[(3-methylpyridin-2-yl) methyl]-2,4-dioxo-1,3,8-triazaspiro[4.5]dec-3-yl}-pyridin-2-yl) benzoic acid | + |
| 10-3 | 4-(5-{8-[(4-methoxypyridin-2-yl) methyl]-1-(6-methoxypyrimidin-4-yl)-2,4-dioxo-1,3,8-triazaspiro[4.5]dec-3-yl}-pyridin-2-yl) benzoic acid | + |
| 10-4 | 4-(5-{8-[(4-hydroxypyridin-2-yl) methyl]-1-(6-methoxypyrimidin-4-yl)-2,4-dioxo-1,3,8-triazaspiro[4.5]dec-3-yl}-pyridin-2-yl) benzoic acid | + |
| 11-1 | 4-(5-{1-(6-methoxypyrimidin-4-yl)-8-[(3-methylpyridin-2-yl) methyl]-2,4-dioxo-1,3,8-triazaspiro[4.5]dec-3-yl}-pyridin-2-yl)-3-methylbenzoic acid | + |
| 11-2 | 4-(5-{1-(4-methoxypyrimidin-2-yl)-8-[(3-methylpyridin-2-yl) methyl]-2,4-dioxo-1,3,8-triazaspiro[4.5]dec-3-yl}-pyridin-2-yl)-3-methylbenzoic acid | + |
| 11-3 | 3-methyl-4-(5-{8-[(3-methylpyridin-2-yl) methyl]-2,4-dioxo-1-(2,2,2-trifluoroethyl)-1,3,8-triazaspiro[4.5]dec-3-yl}-pyridin-2-yl) benzoic acid | + |
| 12-1 | 3-fluoro-4-(5-{1-(6-methoxypyrimidine-4-yl)-8-[(3-methylpyridin-2-yl) methyl]-2,4-dioxo-1,3,8-triazaspiro[4.5] dec-3-yl} pyridin-2-yl)-3-benzoic acid | + |

+ = $0.5 \geq IC_{50} \leq 20$ (nM)
++ = $>20 \geq IC_{50} \leq 50$ (nM)
+++ = $>50\ IC_{50}$ (nM)

What is claimed is:
1. A compound selected from:
3-biphenyl-4-yl-1-(4-hydroxypyrimidin-2-yl)-8-[(3-methylpyridin-2-yl)methyl]-1,3,8-triazaspiro[4.5]decane-2,4-dione;
3-biphenyl-4-yl-8-[(3-methylpyridin-2-yl)methyl]-1-pyridin-2-yl-1,3,8-triazaspiro[4.5]decane-2,4-dione;
1-(4-hydroxypyrimidin-2-yl)-8-[(3-methylpyridin-2-yl)methyl]-3-phenyl-1,3,8-triazaspiro[4.5]decane-2,4-dione;
3-biphenyl-4-yl-8-[(3-methylpyridin-2-yl)methyl]-1-phenyl-1,3,8-triazaspiro[4.5]decane-2,4-dione;
2-{3-biphenyl-4-yl-8-[(3-methylpyridin-2-yl)methyl]-2,4-dioxo-1,3,8-triazaspiro[4.5]dec-1-yl}isonicotinic acid;
3-biphenyl-4-yl-1-(6-fluoropyridin-2-yl)-8-[(3-methylpyridin-2-yl)methyl]-1,3,8-triazaspiro[4.5]decane-2,4-dione;
6-{3-biphenyl-4-yl-8-[(3-methylpyridin-2-yl)methyl]-2,4-dioxo-1,3,8-triazaspiro[4.5]dec-1-yl}nicotinonitrile;
3-biphenyl-4-yl-8-[(3-methylpyridin-2-yl)methyl]-1-pyridin-4-yl-1,3,8-triazaspiro[4.5]decane-2,4-dione;
3-biphenyl-4-yl-1-(6-hydroxypyridazin-3-yl)-8-[(3-methylpyridin-2-yl)methyl]-1,3,8-triazaspiro[4.5]decane-2,4-dione;
3-biphenyl-4-yl-1-(5-hydroxypyrimidin-2-yl)-8-[(3-methylpyridin-2-yl)methyl]-1,3,8-triazaspiro[4.5]decane-2,4-dione;
3-biphenyl-4-yl-1-(6-methoxypyridin-2-yl)-8-[(3-methylpyridin-2-yl)methyl]-1,3,8-triazaspiro[4.5]decane-2,4-dione;
3-biphenyl-4-yl-1-(6-hydroxypyridin-2-yl)-8-[(3-methylpyridin-2-yl)methyl]-1,3,8-triazaspiro[4.5]decane-2,4-dione;
methyl 6-{3-biphenyl-4-yl-8-[(3-methylpyridin-2-yl)methyl]-2,4-dioxo-1,3,8-triazaspiro[4.5]dec-1-yl}pyridine-2-carboxylate;
6-{3-biphenyl-4-yl-8-[(3-methylpyridin-2-yl)methyl]-2,4-dioxo-1,3,8-triazaspiro[4.5]dec-1-yl}pyridine-2-carboxylic acid;
1-(4-methoxypyrimidin-2-yl)-8-[(3-methylpyridin-2-yl)methyl]-3-[4-(1H-tetrazol-5-yl)phenyl]-1,3,8-triazaspiro[4.5]decane-2,4-dione;
1-(4-hydroxypyrimidin-2-yl)-8-[(3-methylpyridin-2-yl)methyl]-3-[4-(1H-tetrazol-5-yl)phenyl]-1,3,8-triazaspiro[4.5]decane-2,4-dione;
4-{1-(4-hydroxypyrimidin-2-yl)-8-[(3-methylpyridin-2-yl)methyl]-2,4-dioxo-1,3,8-triazaspiro[4.5]dec-3-yl}benzoic acid;
3-biphenyl-4-yl-8-[(3-methylpyridin-2-yl)methyl]-1-pyridin-3-yl-1,3,8-triazaspiro[4.5]decane-2,4-dione;
tert-butyl (2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)acetate;
tert-butyl (2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)acetate;
(2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)acetic acid;
3-(2-{[3-biphenyl-4-yl-1-(4-methoxypyrimidin-2-yl)-2,4-dioxo-1,3,8-triazaspiro[4.5]dec-8-yl]methyl}-1H-imidazol-1-yl)propanoic acid;
(2-{[3-biphenyl-4-yl-1-(4-hydroxypyrimidin-2-yl)-2,4-dioxo-1,3,8-triazaspiro[4.5]dec-8-yl]methyl}-1H-imidazol-1-yl)acetic acid;

3-(2-{[3-biphenyl-4-yl-1-(4-hydroxypyrimidin-2-yl)-2,4-dioxo-1,3,8-triazaspiro[4.5]dec-8-yl]methyl}-1H-imidazol-1-yl)propanoic acid;

4-{1-(4-methoxypyrimidin-2-yl)-8-[(3-methylpyridin-2-yl)methyl]-2,4-dioxo-1,3,8-triazaspiro[4.5]dec-3-yl}benzonitrile;

ethyl 4-{1-(4-methoxypyrimidin-2-yl)-8-[(3-methylpyridin-2-yl)methyl]-2,4-dioxo-1,3,8-triazaspiro[4.5]dec-3-yl}benzoate;

3-biphenyl-4-yl-8-[(3-methylpyridin-2-yl)methyl]-1-(2-thienyl)-1,3,8-triazaspiro[4.5]decane-2,4-dione;

3-biphenyl-4-yl-8-[(3-bromopyridin-2-yl)methyl]-1-(4-methoxypyrimidin-2-yl)-1,3,8-triazaspiro[4.5]decane-2,4-dione;

3-biphenyl-4-yl-1-(4-methoxypyrimidin-2-yl)-8-[(3-methylpyridin-2-yl)methyl]-1,3,8-triazaspiro[4.5]decane-2,4-dione;

1-(4-methoxypyrimidin-2-yl)-8-[(3-methylpyridin-2-yl)methyl]-3-phenyl-1,3,8-triazaspiro[4.5]decane-2,4-dione;

3-biphenyl-4-yl-8-[(3-bromopyridin-2-yl)methyl]-1-(4-hydroxypyrimidin-2-yl)-1,3,8-triazaspiro[4.5]decane-2,4-dione;

4-[8-[(3-bromopyridin-2-yl)methyl]-1-(4-hydroxypyrimidin-2-yl)-2,4-dioxo-1,3,8-triazaspiro[4.5]dec-3-yl]-N-phenylbenzamide;

3-biphenyl-4-yl-1-(4-hydroxypyrimidin-2-yl)-8-[(3-methylpyridin-2-yl)methyl]-1,3,8-triazaspiro[4.5]decane-2,4-dione;

4-[8-[(3-bromopyridin-2-yl)methyl]-1-(4-hydroxypyrimidin-2-yl)-2,4-dioxo-1,3,8-triazaspiro[4.5]dec-3-yl]-N-cyclopropylbenzamide;

3-biphenyl-4-yl-8-[(3-bromopyridin-2-yl)methyl]-1-pyrimidin-2-yl-1,3,8-triazaspiro[4.5]decane-2,4-dione;

3-biphenyl-4-yl-8-[(3-bromopyridin-2-yl)methyl]-1-(4-hydroxypyridin-2-yl)-1,3,8-triazaspiro[4.5]decane-2,4-dione;

tert-butyl 2-{[3-biphenyl-4-yl-1-(4-methoxypyrimidin-2-yl)-2,4-dioxo-1,3,8-triazaspiro[4.5]dec-8-yl]methyl}nicotinate;

2-{[3-biphenyl-4-yl-1-(4-hydroxypyrimidin-2-yl)-2,4-dioxo-1,3,8-triazaspiro[4.5]dec-8-yl]methyl}nicotinic acid;

3-biphenyl-4-yl-1-(4-methoxypyrimidin-2-yl)-8-(1H-tetrazol-5-ylmethyl)-1,3,8-triazaspiro[4.5]decane-2,4-dione;

2-{[3-biphenyl-4-yl-1-(4-methoxypyrimidin-2-yl)-2,4-dioxo-1,3,8-triazaspiro[4.5]dec-8-yl]methyl}nicotinonitrile;

3-biphenyl-4-yl-1-(4-methoxypyrimidin-2-yl)-8-{[3-(1H-tetrazol-5-yl)pyridin-2-yl]methyl}-1,3,8-triazaspiro[4.5]decane-2,4-dione;

3-biphenyl-4-yl-1-(2-hydroxypyrimidin-4-yl)-8-[(3-methylpyridin-2-yl)methyl]-1,3,8-triazaspiro[4.5]decane-2,4-dione;

3-biphenyl-4-yl-1-(3-hydroxypyridin-2-yl)-8-[(3-methylpyridin-2-yl)methyl]-1,3,8-triazaspiro[4.5]decane-2,4-dione;

4'-{1-(6-hydroxypyrimidin-4-yl)-8-[(3-methylpyridin-2-yl)methyl]-2,4-dioxo-1,3,8-triazaspiro[4.5]dec-3-yl}biphenyl-4-carboxylic acid;

3-biphenyl-4-yl-1-(5-hydroxypyrazin-2-yl)-8-[(3-methylpyridin-2-yl)methyl]-1,3,8-triazaspiro[4.5]decane-2,4-dione;

Butyl 4-{[3-biphenyl-4-yl-1-(4-hydroxypyrimidin-2-yl)-2,4-dioxo-1,3,8-triazaspiro[4.5]dec-8-yl]methyl}-1-H-imidazole-5-carboxylate;

Butyl 4-{[3-biphenyl-4-yl-1-(4-methoxypyrimidin-2-yl)-2,4-dioxo-1,3,8-triazaspiro[4.5]dec-8-yl]methyl}-1-H-imidazole-5-carboxylate;

Butyl 4-{[3-biphenyl-4-yl-1-(6-methoxypyrimidin-4-yl)-2,4-dioxo-1,3,8-triazaspiro[4.5]dec-8-yl]methyl}-1-H-imidazole-5-carboxylate;

3-biphenyl-4-yl-1-(4-methoxypyrimidin-2-yl)-8-[(5-methyl-1-H-imidazol-4-yl)methyl]-1,3,8-triazaspiro[4.5]decane-2,4-dione;

4-{([3-biphenyl-4-yl-1-(4-methoxypyrimidin-2-yl)-2,4-dioxo-1,3,8-triazaspiro[4.5]dec-8-yl]methyl}-1-H-imidazole-5-carboxylic acid;

4-[(3-biphenyl-4-yl-2,4-dioxo-1,3,8-triazaspiro[4.5]dec-8-yl)methyl]-1-H-imidazole-5-carboxylic acid;

4-{[3-biphenyl-4-yl-1-(6-hydroxypyrimidin-4-yl)-2,4-dioxo-1,3,8-triazaspiro[4.5]dec-8-yl]methyl}-1-H-imidazole-5-carboxylic acid;

3-biphenyl-4-yl-1-(6-hydroxypyrimidin-4-yl)-8-[(5-methyl-1-H-imidazol-4-yl)methyl]-1,3,8-triazaspiro[4.5]decane-2,4-dione;

2-{[3-biphenyl-4-yl-1-(6-hydroxypyrimidin-4-yl)-2,4-dioxo-1,3,8-triazaspiro[4.5]dec-8-yl]methyl}nicotinic acid;

3-biphenyl-4-yl-1-(4,6-dihydroxypyrimidin-2-yl)-8-[(3-methylpyridin-2-yl)methyl]-1,3,8-triazaspiro[4.5]decane-2,4-dione;

3-biphenyl-4-yl-1-(4-hydroxy-6-methoxypyrimidin-2-yl)-8-[(3-methylpyridin-2-yl)methyl]-1,3,8-triazaspiro[4.5]decane-2,4-dione;

3-biphenyl-4-yl-1-(4,6-dimethoxypyrimidin-2-yl)-8-[(3-methylpyridin-2-yl)methyl]-1,3,8-triazaspiro[4.5]decane-2,4-dione;

3-biphenyl-4-yl-1-(2-hydroxypyridin-4-yl)-8-[(3-methylpyridin-2-yl)methyl]-1,3,8-triazaspiro[4.5]decane-2,4-dione;

2-{3-biphenyl-4-yl-8-[(3-methylpyridin-2-yl)methyl]-2,4-dioxo-1,3,8-triazaspiro[4.5]dec-1-yl}pyrimidine-4-carboxylic acid;

6-{3-biphenyl-4-yl-8-[(3-methylpyridin-2-yl)methyl]-2,4-dioxo-1,3,8-triazaspiro[4.5]dec-1-yl}nicotinic acid;

Methyl 4'-{8-[(3-methylpyridin-2-yl)methyl]-2,4-dioxo-1-pyrimidin-2-yl-1,3,8-triazaspiro[4.5]dec-3-yl}biphenyl-4-carboxylate;

Methyl 4-[(3-biphenyl-4-yl-2,4-dioxo-1-pyrimidin-2-yl-1,3,8-triazaspiro[4.5]dec-8-yl)methyl]-1-H-imidazole-5-carboxylate;

4'-{8-[(3-methylpyridin-2-yl)methyl]-2,4-dioxo-1-pyrimidin-2-yl-1,3,8-triazaspiro[4.5]dec-3-yl}biphenyl-4-carboxylic acid;

4-[(3-biphenyl-4-yl-2,4-dioxo-1-pyrimidin-2-yl-1,3,8-triazaspiro[4.5]dec-8-yl)methyl]-1-H-imidazole-5-carboxylic acid;

5-(4-{8-[(3-carboxypyridin-2-yl)methyl]-2,4-dioxo-1-pyrimidin-2-yl-1,3,8-triazaspiro[4.5]dec-3-yl}phenyl)pyridine-2-carboxylic acid;

4'-{8-[(3-methylpyridin-2-yl)methyl]-2,4-dioxo-1-pyrimidin-2-yl-1,3,8-triazaspiro[4.5]dec-3-yl}biphenyl-3-carboxylic acid;

(4'-{8-[(3-methylpyridin-2-yl)methyl]-2,4-dioxo-1-pyrimidin-2-yl-1,3,8-triazaspiro[4.5]dec-3-yl}biphenyl-4-yl)acetic acid;

3-biphenyl-4-yl-8-[(3-methylpyridin-2-yl)methyl]-1-pyrimidin-4-yl-1,3,8-triazaspiro[4.5]decane-2,4-dione;

2-(4-{8-[(3-methylpyridin-2-yl)methyl]-2,4-dioxo-1-pyrimidin-2-yl-1,3,8-triazaspiro[4.5]dec-3-yl}phenyl)cyclopropanecarboxylic acid;

8-[(3-methylpyridin-2-yl)methyl]-1-(6-methoxypyrimidin-4-yl)-3-(4'-propionylbiphenyl-4-yl)-1,3,8-triazaspiro[4.5]decane-2,4-dione;
1-(6-hydroxypyrimidin-4-yl)-8-[(3-methylpyridin-2-yl)methyl]-3-(4'-propionylbiphenyl-4-yl)-1,3,8-triazaspiro[4.5]decane-2,4-dione;
3-biphenyl-4-yl-1-methyl-8-[(3-methylpyridin-2-yl)methyl]-1,3,8-triazaspiro[4.5]decane-2,4-dione;
tert-butyl (3-biphenyl-4-yl-2,4-dioxo-1-pyrazin-2-yl-1,3,8-triazaspiro[4.5]dec-8-yl)acetate;
(3-biphenyl-4-yl-2,4-dioxo-1-pyrazin-2-yl-1,3,8-triazaspiro[4.5]dec-8-yl)acetic acid;
(3-biphenyl-4-yl-2,4-dioxo-1-pyrimidin-5-yl-1,3,8-triazaspiro[4.5]dec-8-yl)acetic acid(3-biphenyl-4-yl-2,4-dioxo-1-pyrimidin-2-yl-1,3,8-triazaspiro[4.5]dec-8-yl) acetic acid;
[3-biphenyl-4-yl-1-(4-methoxypyrimidin-2-yl)-2,4-dioxo-1,3,8-triazaspiro[4.5]dec-8-yl]acetic acid;
2,2'-(3-biphenyl-4-yl-2,4-dioxo-1,3,8-triazaspiro[4.5]decane-1,8-diyl)diacetic acid;
[3-biphenyl-4-yl-1-(2-ethoxy-2-oxoethyl)-2,4-dioxo-1,3,8-triazaspiro[4.5]dec-8-yl]acetic acid;
3-biphenyl-4-yl-8-[(3-methylpyridin-2-yl)methyl]-1,3,8-triazaspiro[4.5]decane-2,4-dione;
(3-biphenyl-4-yl-2,4-dioxo-1,3,8-triazaspiro[4.5]dec-8-yl)acetic acid;
ethyl 3-biphenyl-4-yl-1-(4-methoxypyrimidin-2-yl)-8-[(3-methylpyridin-2-yl)methyl]-2,4-dioxo-1,3,8-triazaspiro[4.5]decane-6-carboxylate;
ethyl 3-biphenyl-4-yl-1-(4-hydroxypyrimidin-2-yl)-8-[(3-methylpyridin-2-yl)methyl]-2,4-dioxo-1,3,8-triazaspiro[4.5]decane-6-carboxylate;
3-biphenyl-4-yl-1-(4-hydroxypyrimidin-2-yl)-8-[(3-methylpyridin-2-yl)methyl]-2,4-dioxo-1,3,8-triazaspiro[4.5]decane-6-carboxylic acid;
3-biphenyl-4-yl-8-[(3-methylpyridin-2-yl)methyl]-2,4-dioxo-1,3,8-triazaspiro[4.5]decane-6-carboxylic acid;
Ethyl 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylate;
3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid;
3-biphenyl-4-yl-8-[(3-methylpyridin-2-yl)methyl]-2,4-dioxo-1-pyrimidin-2-yl-1,3,8-triazaspiro[4.5]decane-6-carboxylic acid;
Ethyl 3-biphenyl-4-yl-1-(6-methoxypyrimidin-4-yl)-8-[(3-methylpyridin-2-yl)methyl]-2,4-dioxo-1,3,8-triazaspiro[4.5]decane-6-carboxylate;
Ethyl 3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylate;
3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid;
3-biphenyl-4-yl-1-(6-hydroxypyrimidin-4-yl)-8-[(3-methylpyridin-2-yl)methyl]-2,4-dioxo-1,3,8-triazaspiro[4.5]decane-6-carboxylic acid;
ethyl [({3-biphenyl-4-yl-8-[(3-methylpyridin-2-yl)methyl]-2,4-dioxo-1,3,8-triazaspiro[4.5]dec-6-yl}carbonyl)amino]acetate;
tert-butyl [({3-biphenyl-4-yl-8-[(3-methylpyridin-2-yl)methyl]-2,4-dioxo-1,3,8-triazaspiro[4.5]dec-6-yl}carbonyl)amino]acetate;
[({3-biphenyl-4-yl-8-[(3-methylpyridin-2-yl)methyl]-2,4-dioxo-1,3,8-triazaspiro[4.5]dec-6-yl}carbonyl)amino]acetic acid;
2-[({3-biphenyl-4-yl-8-[(3-methylpyridin-2-yl)methyl]-2,4-dioxo-1,3,8-triazaspiro[4.5]dec-1-yl}carbonyl)amino]-2-methylpropanoic acid;
(2R)-2-[({3-biphenyl-4-yl-8-[(3-methylpyridin-2-yl)methyl]-2,4-dioxo-1,3,8-triazaspiro[4.5]dec-1-yl}carbonyl)amino]propanoic acid;
(2S)-2-[({3-biphenyl-4-yl-8-[(3-methylpyridin-2-yl)methyl]-2,4-dioxo-1,3,8-triazaspiro[4.5]dec-1-yl}carbonyl)amino]propanoic acid;
N-({3-biphenyl-4-yl-8-[(3-methylpyridin-2-yl)methyl]-2,4-dioxo-1,3,8-triazaspiro[4.5]dec-1-yl}carbonyl)-L-serine;
4-{3-biphenyl-4-yl-8-[(3-methylpyridin-2-yl)methyl]-2,4-dioxo-1,3,8-triazaspiro[4.5]dec-1-yl}-4-oxobutanoic acid;
4'-{1-(6-methoxypyrimidin-4-yl)-8-[(3-methylpyridin-2-yl)methyl]-2,4-dioxo-1,3,8-triazaspiro[4.5]dec-3-yl}biphenyl-4-carboxylic acid;
4'-{1-(6-methoxypyrimidin-4-yl)-8-[(3-methylpyridin-2-yl)methyl]-2,4-dioxo-1,3,8-triazaspiro[4.5]dec-3-yl}-2-methylbiphenyl-4-carboxylic acid;
4'-{1-(6-methoxypyrimidin-4-yl)-8-[(3-methylpyridin-2-yl)methyl]-2,4-dioxo-1,3,8-triazaspiro[4.5]dec-3-yl}-3-methylbiphenyl-4-carboxylic acid;
2-fluoro-4'-{1-(6-methoxypyrimidin-4-yl)-8-[(3-methylpyridin-2-yl)methyl]-2,4-dioxo-1,3,8-triazaspiro[4.5]dec-3-yl}biphenyl-4-carboxylic acid;
2-methyl-4'-{8-[(3-methylpyridin-2-yl)methyl]-2,4-dioxo-1-pyrazin-2-yl-1,3,8-triazaspiro[4.5]dec-3-yl}biphenyl-4-carboxylic acid;
2-methyl-4'-{1-(6-methylpyrazin-2-yl)-8-[(3-methylpyridin-2-yl)methyl]-2,4-dioxo-1,3,8-triazaspiro[4.5]dec-3-yl}biphenyl-4-carboxylic acid;
4'-{1-(6-methylpyrazin-2-yl)-8-[(3-methylpyridin-2-yl)methyl]-2,4-dioxo-1,3,8-triazaspiro[4.5]dec-3-yl}biphenyl-4-carboxylic acid;
2-methyl-4'-[8-[(3-methylpyridin-2-yl)methyl]-1-(6-methylpyrimidin-4-yl)-2,4-dioxo-1,3,8-triazaspiro[4.5]dec-3-yl]biphenyl-4-carboxylic acid;
4'-[8-[(3-methylpyridin-2-yl)methyl]-1-(6-methylpyrimidin-4-yl)-2,4-dioxo-1,3,8-triazaspiro[4.5]dec-3-yl]biphenyl-4-carboxylic acid;
2-methyl-4'-{8-[(3-methylpyridin-2-yl)methyl]-2,4-dioxo-1-[6-(trifluoromethyl)pyrimidin-4-yl]-1,3,8-triazaspiro[4.5]dec-3-yl}biphenyl-4-carboxylic acid;
1-(6-methoxypyrimidin-4-yl)-8-[(3-methylpyridin-2-yl)methyl]-3-[4'-(1H-pyrazol-5-yl) biphenyl-4-yl]-1,3,8-triazaspiro[4.5]decane-2,4-dione;
1-(6-hydroxypyrimidin-4-yl)-8-[(3-methylpyridin-2-yl)methyl]-3-[4'-(1H-pyrazol-5-yl) biphenyl-4-yl]-1,3,8-triazaspiro[4.5]decane-2,4-dione;
1-(6-methoxypyrimidin-4-yl)-8-[(3-methylpyridin-2-yl)methyl]-3-[4'-(5-oxopyrazolidin-3-yl)biphenyl-4-yl]-1,3,8-triazaspiro[4.5]decane-2,4-dione;
1-(6-hydroxypyrimidin-4-yl)-8-[(3-methylpyridin-2-yl)methyl]-3-[4'-(1 morpholin-4-yl) biphenyl-4-yl]-1,3,8-triazaspiro[4.5]decane-2,4-dione;
4-(6-{3-(4-bromophenyl)-8-[(3-methylpyridin-2-yl)methyl]-2,4-dioxo-1,3,8-triazaspiro[4.5]dec-1-yl}pyrimidin-4-yl)benzoic acid;
4'-{8-[(3-methylpyridin-2-yl)methyl]-2,4-dioxo-1-pyrimidin-4-yl-1,3,8-triazaspiro[4.5]dec-3-yl}biphenyl-4-carboxylic acid;
methyl 2-methyl-4'-{8-[(3-methylpyridin-2-yl)methyl]-2,4-dioxo-1-pyrimidin-4-yl-1,3,8-triazaspiro[4.5]dec-3-yl}biphenyl-4-carboxylate;

2-methyl-4'-{8-[(3-methylpyridin-2-yl)methyl]-2,4-dioxo-1-pyrimidin-4-yl-1,3,8-triazaspiro[4.5]dec-3-yl}biphenyl-4-carboxylic acid;

2-methyl-4'-[8-[(3-methylpyridin-2-yl)methyl]-1-(2-methylpyrimidin-4-yl)-2,4-dioxo-1,3,8-triazaspiro[4.5]dec-3-yl]biphenyl-4-carboxylic acid;

2-methyl-4'-{8-[(3-methylpyridin-2-yl)methyl]-2,4-dioxo-1-pyridazin-3-yl-1,3,8-triazaspiro[4.5]dec-3-yl}biphenyl-4-carboxylic acid;

4-(5-{1-(6-methoxypyrimidin-4-yl)-8-[(3-methylpyridin-2-yl)methyl]-2,4-dioxo-1,3,8-triazaspiro[4.5]dec-3-yl}-pyridin-2-yl)benzoic acid;

4-(5-{1-(4-methoxypyrimidin-2-yl)-8-[(3-methylpyridin-2-yl)methyl]-2,4-dioxo-1,3,8-triazaspiro[4.5]dec-3-yl}-pyridin-2-yl)benzoic acid;

4-(5-{8-[(4-methoxypyridin-2-yl)methyl]-1-(6-methoxypyrimidin-4-yl)-2,4-dioxo-1,3,8-triazaspiro[4.5]dec-3-yl}-pyridin-2-yl)benzoic acid;

4-(5-{8-[(4-hydroxypyridin-2-yl)methyl]-1-(6-methoxypyrimidin-4-yl)-2,4-dioxo-1,3,8-triazaspiro[4.5]dec-3-yl}-pyridin-2-yl)benzoic acid;

4-(5-{1-(6-methoxypyrimidin-4-yl)-8-[(3-methylpyridin-2-yl)methyl]-2,4-dioxo-1,3,8-triazaspiro[4.5]dec-3-yl}-pyridin-2-yl)-3-methylbenzoic acid;

4-(5-{1-(4-methoxypyrimidin-2-yl)-8-[(3-methylpyridin-2-yl)methyl]-2,4-dioxo-1,3,8-triazaspiro[4.5]dec-3-yl}-pyridin-2-yl)-3-methylbenzoic acid;

3-methyl-4-(5-{8-[(3-methylpyridin-2-yl)methyl]-2,4-dioxo-1-(2,2,2-trifluoroethyl)-1,3,8-triazaspiro[4.5]dec-3-yl}-pyridin-2-yl)benzoic acid;

3-fluoro-4-(5-{1-(6-methoxypyrimidine-4-yl)-8-[(3-methylpyridin-2-yl)methyl]-2,4-dioxo-1,3,8-triazaspiro[4.5]dec-3-yl}pyridin-2-yl)-3-benzoic acid;

or a pharmaceutically acceptable salt thereof, or a stereoisomer thereof, or a pharmaceutically acceptable salt of the stereoisomer thereof.

2. A pharmaceutical composition comprising a compound of claim 1 and pharmaceutically acceptable carrier.

3. A method of enhancing endogenous production of erythropoietin in a mammal which comprises administering to the mammal an amount of a compound of claim 1, or a pharmaceutically acceptable salt thereof, that is effective for enhancing endogenous production of erythropoietin.

4. A method for the prevention or treatment of anemia in a mammal which comprises administering to the mammal an effective amount of a compound of claim 1, or a pharmaceutically acceptable salt thereof.

* * * * *